US007163801B2

(12) United States Patent
Reed

(10) Patent No.: US 7,163,801 B2
(45) Date of Patent: Jan. 16, 2007

(54) METHODS FOR DETERMINING THE PROGNOSIS FOR CANCER PATIENTS USING TUCAN

(75) Inventor: John C. Reed, Rancho Santa Fe, CA (US)

(73) Assignee: The Burnham Institute, La Jolla, CA (US)

(*) Notice: Subject to any disclaimer, the term of this patent is extended or adjusted under 35 U.S.C. 154(b) by 494 days.

(21) Appl. No.: 10/141,618

(22) Filed: May 7, 2002

(65) Prior Publication Data

US 2003/0165887 A1 Sep. 4, 2003

Related U.S. Application Data

(63) Continuation-in-part of application No. 09/388,221, filed on Sep. 1, 1999, now Pat. No. 6,818,750.

(60) Provisional application No. 60/356,934, filed on Feb. 12, 2002, provisional application No. 60/289,233, filed on May 7, 2001.

(51) Int. Cl.
*G01N 33/50* (2006.01)
*G01N 33/483* (2006.01)
*G01N 33/53* (2006.01)

(52) U.S. Cl. ....................... 435/7.23; 435/7.1; 435/7.2; 435/7.21; 435/325

(58) Field of Classification Search ................. 435/7.1, 435/7.2, 7.21, 7.23, 325
See application file for complete search history.

(56) References Cited

U.S. PATENT DOCUMENTS 6,110,691 A 8/2000 Wang et al.

FOREIGN PATENT DOCUMENTS

| | | |
|---|---|---|
| WO | WO 96/12016 | 4/1996 |
| WO | WO 99/40102 | 8/1999 |
| WO | WO 01/16170 | 9/2000 |
| WO | WO 01/00826 | 1/2001 |
| WO | WO 01/18042 | 3/2001 |
| WO | WO 01/22920 | 4/2001 |
| WO | WO 01/30813 | 5/2001 |
| WO | WO 01/30971 | 5/2001 |
| WO | WO 01/66690 | 9/2001 |
| WO | WO 01/72822 | 10/2001 |

OTHER PUBLICATIONS

Sinicrope et al. (1999) Clin. Can. Res., vol. 5, 1973-1804.*

Liu et al. (2001) Eur. J. Canc., vol. 37, 1104-1110.*

Bertin et al., "Human CARD4 Protein Is a Novel CED=4/Apaf-1 Cell Death Family Member That Activates NF-kB," *Journal of Biological Chemistry* 274(19):12955-12958 (1999).

Chu et al., "A novel enhancer of the Apaf1 apoptosome involved in cytochrome c-dependent caspase activation and apoptosis," *J. Biol. Chem.* 276:9239-9245 (2001).

Damiano et al., "*CLAN*, a Novel Human CED-4-like Gene," *Genomics* 75:77-83 (2001).

Geddes et al., "Human CARD12 Is a Novel CED4/Apaf-1 Family Member That Induces Apoptosis," *Biochemical and Biophysical Research Communications* 284:77-82 (2001).

Hlaing et al., "Molecular cloning and characterization of DEFCAP-L and —S, two isoforms of a novel member of the mammalian Ced-4 family of apoptosis proteins," *J. Biol. Chem.* 276:9230-9238 (2001).

Hofmann and Bucher, "The CARD domain: a new apoptotic signalling motif," *TIBS* 22 (5) :155-156 (1997).

Kawasaki et al., "Inhibition of Apoptosis by Survivin Predicts Shorter Survival Rates in Colorectal Cancer," *Cancer Research* 58:5071-5074 (1998).

Kobe and Deisenhofer, "Proteins with Leucine-rich repeats," *Current Opinion in Structural Biology*, 3 (5) :409-416 (1995).

Koonin and Aravind, "The NACHT family —a new group of predicted NTPases implicated in apoptosis and MHC transcription activation," *TIBS* 25 (5) :223-224 (2000).

Ogura et al., "Nod2, a Nod1/Apag-1 Family Member That Is Restricted to Monocytes and Activates NF-kB," *Journal of Biological Chemistry* 276 (7) :4812-4818 (2001).

Pathan et al., "TUCAN, an Antiapoptotic Caspase-associated Recruitment Domain Family Protein Overexpressed in Cancer," *J. Biol. Chem.* 276:32220-32229 (2001).

Poyet et al., "Identification of Ipaf, a Human Caspaase-1-activating Protein Related to Apaf-1," *Journal of Biological Chemistry* 276:28309-28313 (2001).

Rychlewski et al., "Comparison of sequence profiles. Strategies for structural predictions using sequence information," *Protein Science* 9:232-241 (2000).

Stapleton et al., "The crystal structure of an Eph receptor SAM domain reveals a mechanism for modular dimerization," *Nature Structural Biology* 6 (1) :44-49 (1999).

Tamm et al., "Expression and prognostic significance of IAP-family gene in human cancers and myeloid leukemias," *Clin. Cancer Res.* 6 (5) :1796-803 (2000).

(Continued)

*Primary Examiner*—Anne M. Wehbé
(74) *Attorney, Agent, or Firm*—McDermottt Will & Emery LLP

(57) ABSTRACT

The invention provides methods for determining a prognosis for survival for a cancer patient. One method involves (a) measuring a level of a TUCAN in a neoplastic cell-containing sample from the cancer patient, and (b) comparing the level of TUCAN in the sample to a reference level of TUCAN, wherein a low level of TUCAN in the sample correlates with increased survival of the patient. Another method involves (a) measuring a level of TUCAN in a neoplastic cell-containing sample from the cancer patient, and (b) classifying the patient as belonging to either a first or second group of patients, wherein the first group of patients having low levels of TUCAN is classified as having an increased likelihood of survival compared to the second group of patients having high levels of TUCAN.

32 Claims, 12 Drawing Sheets

OTHER PUBLICATIONS

GenBank: Accession No. AC007728, Jun. 7, 1999.
GenBank: Accession No. AC010968, Sep. 29, 1999.
GenBank: Accession No. AC016492, Dec. 10, 1999.
GenBank: Accession No. AC025758, Mar. 16, 2000.
GenBank: Accession No. AC026732, Mar. 24, 2000.
GenBank: Accession No. AF322184.1, Apr. 15, 2002.
GenBank: Accession No. AF331519.1, Feb. 4, 2001.
GenBank: Accession No. AQ534686, May 18, 1999.
GenBank: Accession No. AY026322.1, Feb. 21, 2001.
Bouchier-Hayes et al., "CARDINAL, a novel caspase recruitment domain protein, is an inhibitor of multiple NF-kappa B activiation pathways," *J Biol Chem*. 276(47):44069-44077 (2001).
Ferreira et al., "Expression of cIAP1, cIAP2 and XIAP in relation to prognosis and response to chemotherapy in advanced non-small-cell lung cancer (NSCLC) patients," *Proceedings of the American Association for Cancer Research Annual Meeting* 42:358-359 (2001).
Huerta et al., "Downstream apoptosis effectors APAF-1 and CLARP are markedly reduced in colon cancer," *Gastroenterology*120(5)(1):A63 2001.
Saleh et al., "Immunohistochemical expression of bcl-2 and p53 oncoproteins: correlation with Ki67 proliferation index and prognostic histopathologic parameters in colorectal neoplasia," *Appl. Immunohistochem Mol Morphol*. 8(3):175-182 (2000).
Sinicrope et al., "Apoptotic and mitotic indices predict survival rates in lymph node-negative colon carcinomas," *Clin Cancer Res*. 5(7):1793-1804 (1999).
GenBank Accession No. AAB62572.

* cited by examiner

METHODS FOR DETERMINING THE PROGNOSIS FOR CANCER PATIENTS USING TUCAN

This application is a continuation-in-part of U.S. patent application Ser. No. 09/388,221, filed Sep. 1, 1999 now U.S. Pat. No. 6,818,750, and claims the benefit of U.S. Provisional Application No. 60/356,934, filed Feb. 12, 2002, and U.S. Provisional Application No. 60/289,233, filed May 7, 2001, each of which is incorporated herein by reference.

This invention was made with government support under grant numbers AG15402, CA69381 and NS36821, awarded by the National Institutes of Health. The United States Government has certain rights in this invention.

BACKGROUND OF THE INVENTION

This invention relates generally to cancer and, more specifically, to biomarkers that can be used to diagnose or prognose cancer.

Cancer remains a major public health problem that profoundly affects the more than 1 million people diagnosed each year, as well as their families and friends. As our Nation's population grows and ages, more people will get cancer. The use of screening tests to detect cancers early often leads to more effective treatment with fewer side effects. Patients whose cancers are found early also are less likely to die from these cancers than are those whose cancers are not found until symptoms appear.

One type of cancer screening test involves the detection of a biomarker, such as a tumor marker, in a fluid or tissue obtained from a patient. Tumor markers are substances produced by cancer cells that are not typically produced by normal cells. These substances generally can be detected in the body fluids or tissues of patients with cancer. Unfortunately, some tumor markers also can be detected in significant amounts in the body fluids or tissues of people who do not have cancer, making certain markers less reliable for diagnosis. Nevertheless, tumor markers remain an important tool for diagnosing cancer.

Another important use for tumor markers is for monitoring patients being treated for advanced cancer. Measuring tumor markers for this purpose can be less invasive, less time-consuming, as well as less expensive, than repeating chest x-rays, computed tomography (CT) scans, bone scans, or other complicated tests, to determine if a therapy is reducing the cancer.

A further important use for tumor markers is for determining a prognosis of survival of a cancer patient. Such prognostic methods can be used to identify surgically treated patients likely to experience cancer recurrence so that they can be offered additional therapeutic options. Biomarkers useful for prognosis of survival also can be especially effective for determining the risk of metastasis in patients who demonstrate no measurable metastasis at the time of examination or surgery. Knowledge of the likelihood of metastasis in a cancer patient can be an important factor in selecting a treatment option. For example, a cancer patient likely to experience metastasis may be advantageously treated using a modality that is particularly aggressive.

Thus, there exists a need for identification of biomarkers that can be used as diagnostic and prognostic indicators for cancer. The present invention satisfies this need and provides related advantages as well.

SUMMARY OF THE INVENTION

The invention provides methods for determining a prognosis for survival for a cancer patient. One method involves (a) measuring a level of a TUCAN in a neoplastic cell-containing sample from the cancer patient, and (b) comparing the level of TUCAN in the sample to a reference level of TUCAN, wherein a lower level of TUCAN in the sample correlates with increased survival of the patient.

Another method for determining a prognosis for survival for a cancer patient involves (a) measuring levels of TUCAN and one or more biomarkers selected from the group consisting of cIAP2, Apaf1, Bcl-2 and Smac in a neoplastic cell-containing sample from the cancer patient, and (b) comparing the level of TUCAN and the one or more selected biomarkers in the sample to a reference level of TUCAN and the one or more selected biomarkers, wherein a low level of TUCAN and a high level of any of Apaf1, Bcl-2 or Smac, or a low level of TUCAN and a low level of cIAP2, in said sample correlate with increased survival of said patient.

A further method of determining a prognosis for survival for a cancer patient involves (a) measuring a level of TUCAN in a neoplastic cell-containing sample from the cancer patient, and (b) classifying the patient as belonging to either a first or second group of patients, wherein the first group of patients having low levels of TUCAN is classified as having an increased likelihood of survival than the second group of patients having high levels of TUCAN.

The invention also provides a method for monitoring the effectiveness of a course of treatment for a patient with cancer. The method involves (a) determining a level of a TUCAN in a neoplastic cell-containing sample from the cancer patient prior to treatment, and (b) determining the level of TUCAN in a neoplastic cell-containing sample from the patient after treatment, whereby comparison of the TUCAN level prior to treatment with the TUCAN level after treatment indicates the effectiveness of the treatment.

BRIEF DESCRIPTION OF THE DRAWINGS

FIG. 1A shows a colon cancer microarray slide stained for cIAP2 (×5 magnification). Examples of normal colonic epithelium immunostaining are presented for cIAP1 (FIG. 1B; ×100), Survivin (FIG. 1D; ×150), Smac (FIG. 1E; ×150), AIF (FIG. 1G; ×150), and Tucan (FIG. 1K; ×20). Immunostaining results in regions of invasive cancer are shown for Smac (FIG. 1F; ×400), AIF (FIG. 1H; ×250), Apaf1 (FIG. 1I, FIG. 1J; ×200), TUCAN (FIG. 1L ×20.

FIG. 3A shows immunoblot analysis of the indicated in vitro translated proteins using polyclonal XIAP antiserum. FIG. 3B shows immunoblot analysis of recombinant IAP-family proteins and lysates from normal tissues lacking Survivin mRNA and protein versus tumor cell lines which express Survivin protein using anti-Survivin antiserum. FIG. 3C shows immunoblot analysis of GST-Smac recombinant protein using anti-Smac antiserum. FIG. 3D shows immunoblot analysis of Jurkat cells transfected as indicated using anti AIF antiserum. FIG. 3E shows immunoblot analysis of detergent lysates of five frozen colon cancer specimens which were identified as having sufficient amounts of both adjacent normal (N) and tumor (T) tissue for immunoblot analysis using antibodies specific for IAPs, Apaf1, and other proteins. FIG. 3F shows densitometry analysis of the immunoblots shown in FIG. 3E.

FIGS. 5A and 5B illustrate a combination of biomarkers (FIG. 5A, low cIAP2 and high Apaf1: FIG. 5B, low cIAP2 and low TUCAN) with positive impact on disease-free survival. The two combinations of markers with an adverse effect on survival are presented in FIG. 5C (low Apaf1 and high TUCAN) and FIG. 5D (low Bcl-2 and high cIAP2).

FIG. 6A shows immunoblot analysis of representative human tumor cell lines from the NCI panel of 60 human tumor cell lines using an antiserum specific for TUCAN. FIG. 6B shows immunoblot analysis using TUCAN antiserum showing the levels of endogenous TUCAN protein in some of these cancer cell lines compared with HEK293T and Jurkat cells transfected with TUCAN.

FIGS. 8A–8C show representative results from co-immunoprecipitation experiments performed using TUCAN containing either Flag or Myc epitope tags. FIG. 8A shows that TUCAN co-immunoprecipitated with pro-caspase-9 but not the CARD-containing protein Apaf1. TUCAN also did not associate non-specifically with pro-caspase-8 and-10. FIG. 8B shows that pro-caspase-9 co-immunoprecipitated with full-length TUCAN and the CARD only fragment of TUCAN (residues 345–431) but not the ΔCARD fragment of TUCAN lacking the CARD (residues 1–337). FIG. 8C shows self-association of TUCAN using HA and Myc-tagged proteins. Full-length TUCAN interacted with full-length TUCAN and the CARD-only fragment but not the ΔCARD fragment.

DETAILED DESCRIPTION OF THE INVENTION

Figure 1:
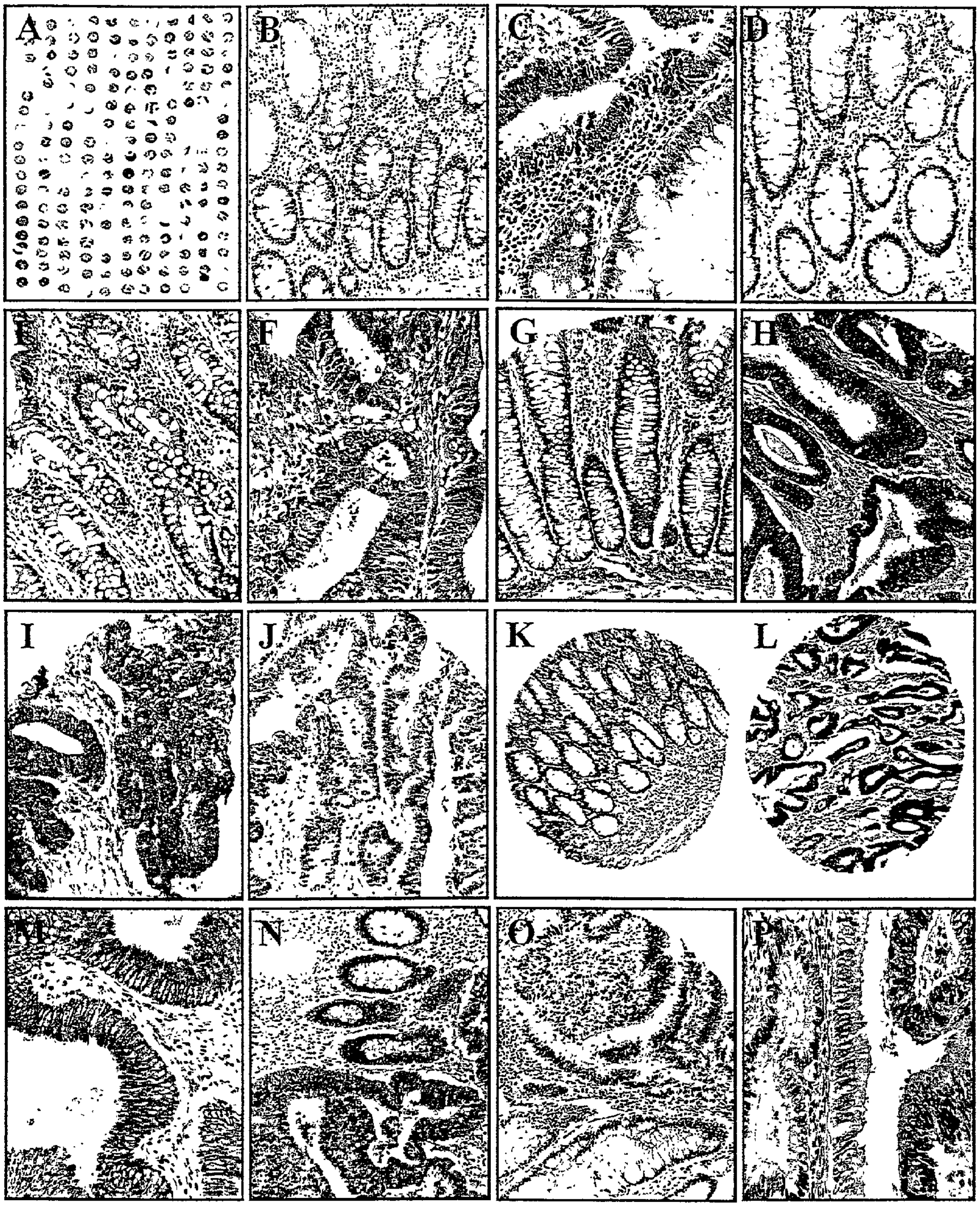
FIGS. 1A–1P show examples of immunohistochemical detection of IAP-family proteins, Apaf1 and TUCAN in normal and malignant colon tissues.
FIG. 1M ×400), and Bcl-2 (FIG. 1N; ×150). Examples of malignant and the adjacent normal colonic epithelium are presented for cIAP2 (FIG. 1C; ×40), p53 (FIG. 1O; ×150) and MIB-1 (FIG. 1P; ×400).

This invention relates to the finding that expression of the CARD domain containing protein, TUCAN (Tumor Up-regulated CARD-containing Antagonist of Caspase Nine), formerly known as CARD-X in PCT publication WO 01/16170, can be used to effectively predict clinical outcome for patients with cancer, either independently, or in combination with other biomarkers.

The prognostic methods of the invention are useful for determining if a patient is at risk for relapse. Cancer relapse is a concern relating to a variety of types of cancer. For example, of patients undergoing complete surgical removal of colon cancer, 25–40% of patients with stage II colon carcinoma and about 50% of patients with stage III colon carcinoma experience cancer recurrence. One explanation for cancer recurrence is that patients with relatively early stage disease (for example, stage II or stage III) already have small amounts of cancer spread outside the affected organ that were not removed by surgery. These cancer cells, referred to as micrometastases, cannot typically be detected with currently available tests. The prognostic methods of the invention can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods of the invention also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

As disclosed herein in Examples II and VIII, elevated levels of TUCAN were found in 49 and 64% of colon tumor specimens examined, respectively. Univariate analysis was used to determine significant correlations between longer disease-free survival (DFS) and low expression of TUCAN (p=0.0004). As shown in Example IV, 78% ($^{39}/_{50}$) of patients whose tumors contained low levels of TUCAN remained alive and disease-free during the time covered by this study, compared to only 44% ($^{21}/_{48}$) of those with high expression of this protein. Example VIII also indicates that TUCAN immunostaining was significantly higher among patients who died of colon cancer, as compared to patients who remained alive.

As shown in Example IV, at a median follow-up of 5 years, 49% of patients with high expression of TUCAN had relapse or died of colon cancer, and only 19% had recurrence and 4% died of disease in a group of patients whose tumors expressed low levels of this protein. Multivariate analysis indicated that the presence of high TUCAN increased risk of death from colon cancer 17-fold (p=000004). Therefore, a high level of TUCAN in a sample from a patient with cancer correlates with increased likelihood of tumor metastasis and reduced survival. Similarly, a low level of TUCAN in a sample from a patient with cancer correlates with decreased likelihood of tumor metastasis and increased likelihood of survival.

Also disclosed herein is the observation that the combination of low levels of cIAP2 and low levels of TUCAN identified a subgroup of early-stage colon cancer patients with very favorable outcome. Approximately one-third of patients in a cohort of 92 patients had a combination of low cIAP2 and low TUCAN ($^{33}/_{92}$ [36%]). Among these 33 patients, 32 (97%) remained alive and 30 (91%) disease-free during the time covered by this study, as opposed to 56% and 44% for other categories of patients. Similarly, in a cohort of 81 patients, 17 had a combination of high Apaf1 and low TUCAN. All (17) patients featuring high expression of Apaf1 and low TUCAN were alive and relapse-free at the end of the survey, compared to only 65% ($^{53}/_{81}$) alive and 53% ($^{43}/_{81}$) recurrence-free for those who were not characterized by this feature. Therefore, a high level of TUCAN combined with a high level of cIAP2 or a low level of Apaf1 in a sample from a patient with cancer correlates with increased likelihood of tumor metastasis and reduced likelihood of survival, whereas a low level of TUCAN combined with a low level of cIAP2 or a high level of Apaf1 in a sample from a patient with cancer correlates with reduced likelihood of tumor metastasis and increased likelihood of survival.

Based on these results, the invention provides methods for diagnosing neoplastic conditions, prognosing survival of patients suffering from cancer, and determining a stage of cancer using TUCAN as a biomarker. TUCAN can be used alone or in combination with other prognostic indicators as a specific biomarker for prognosing survival of patients suffering from cancer.

As disclosed herein, elevated levels of Apaf1, Survivin, XIAP, cIAP1, and cIAP2 were found in 38%, 54%, 74%, 61% and 35% of colon tumor specimens, respectively. Univariate analysis was used to determine significant correlations between longer disease-free survival (DFS) and low expression of cIAP2 (p=0.0002), β-catenin (p=0.04), mutant p53 protein (p=0.03), or high levels of Apaf1 (p=0.00008), Bcl-2 (p=0.005), and SMAC (p=0.03) (see FIG. 4*a*). Thus, 78% (39/50) of patients whose tumors contained low levels of TUCAN remained alive and disease-free during the time covered by this study, compared to only 44% (21/48) of those with high expression of this protein. Similarly, 74% (45/61) of low cIAP2 expressors were cancer-free at the time of last survey compared to only 36% (12/33) of those with high cIAP2 levels. At a median follow-up of 5 years, 60% of patients with high cIAP2 levels relapsed and 46% died of colon cancer, whereas in a low-cIAP2 group there were 20% relapses and 18% colon cancer-related deaths.

As further disclosed herein, high levels of Apaf1 were associated with longer survival, with 33/38 (87%) of colon cancer patients remaining disease-free compared to only 28/62 (45%) of those with low Apaf1 expression. In contrast, 43% of patients with low Apaf1 relapsed and 35% died of colon cancer, while only 14% had a cancer recurrence or died in a high-Apaf1 cohort. Low Bcl-2 levels also were associated with poor overall survival. Of 18 patients with low expression of this protein, 11 (61%) died of colon cancer, compared with 24% of patients who died in the high-Bcl-2 group (18/76). Similarly, patients whose tumors contained low Apaf1 staining had worse overall survival compared with those who overexpressed Bcl-2 (FIG. 1N). Multivariate analysis indicated that high Apaf1 and Bcl-2 expression was associated with a decreased relative risk of dying of colon cancer by 75% (p=0.004) and 82% (p=0.00006). Therefore, a decreased level of Apaf1 or Bcl-2 in a sample from a patient with colon cancer correlates positively with increased chance of tumor metastasis and reduced survival.

Also disclosed herein is the observation that the combination of low levels of cIAP2 and high levels of Apaf1 identified a subgroup of early-stage colon cancer patients with very favorable outcome. Roughly one-quarter (25/94 [27%]) of the tumors analyzed contained both low cIAP2 and high Apaf1. Among these 25 patients, all 25 remained alive and free of disease after surgery at the time of last survey (median follow-up 5 years). Thus, the median 5 yr disease-free and overall survival rate for this group of patients was 100%, compared to only 50% and 64% for other categories of patients, respectively. Therefore, an increased level of cIAP2 and decreased level of Apaf1 in a sample from a patient with colon cancer correlates with increased chance of tumor metastasis and reduced survival.

As used herein, the term "level" refers to mean the amount, accumulation or rate of a biomarker molecule, such as TUCAN. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. The term can be used to refer to an absolute amount of a molecule in a sample or to a relative amount of the molecule, including amounts determined under steady-state or non-steady-state conditions. The expression level of a molecule can be determined relative to a control molecule in a sample.

When used in reference to TUCAN mRNA or polypeptide, the term level refers to the extent, amount or rate of synthesis of the nucleic acid sequence shown as SEQ ID NO:1 or the TUCAN polypeptide shown as SEQ ID NO:2, or substantially the same nucleotide or amino acid sequences. The nucleic acid sequence and amino acid sequence of TUCAN, formerly referenced as CARD-X, are also described in PCT publication WO 01/16170, which is incorporated herein by reference. When used in reference to cIAP2 mRNA or polypeptide expression, the term level refers to the extent, amount or rate of synthesis of the nucleic acid sequence shown as SEQ ID NO:5 or the CIAP2 polypeptide shown as SEQ ID NO:6, or substantially the same nucleotide or amino acid sequences. When used in reference to β-catenin mRNA or polypeptide, the term level refers to the extent, amount or rate of synthesis of the nucleic acid sequence shown as SEQ ID NO:7 or the β-catenin polypeptide shown as SEQ ID NO:8, or substantially the same nucleotide or amino acid sequences. When used in reference to Apaf1 mRNA or polypeptide, the term level refers to the extent, amount or rate of synthesis of the nucleic acid sequence shown as SEQ ID NO:9 or the Apaf1 polypeptide shown as SEQ ID NO:10, or substantially the same nucleotide or amino acid sequences. When used in reference to Bcl-2 mRNA or polypeptide, the term level refers to the extent, amount or rate of synthesis of the nucleic acid sequence shown as SEQ ID NO:11 or the Bcl-2 polypeptide shown as SEQ ID NO:12, or substantially the same nucleotide or amino acid sequences. When used in reference to Smac mRNA or polypeptide, the term level refers to the extent, amount or rate of synthesis of the nucleic acid sequence shown as SEQ ID NO:13 or the Smac polypeptide shown as SEQ ID NO:14, or substantially the same nucleotide or amino acid sequences. A level of these and other biomarkers of cancer, including XIAP, cIAP1, Survivin, Bcl-XL, Bax, BAG1, mutant p53, p53 and MIB-1, can be a gene expression level or a polypeptide expression level.

An amino acid sequence that has substantially the same amino acid sequence as a reference amino acid sequence contains a considerable degree of sequence identity or similarity, such as at least 70%, 80%, 90%, 95%, 98%, or 100% sequence identity or similarity, to a reference amino acid sequence. Such changes, gaps and insertions can be naturally occurring mutations, or can result from processing a sample containing the polypeptide. A nucleotide sequence that is substantially the same as a reference nucleotide sequences contains a considerable degree of sequence identity or similarity, such as at least 70%, 80%, 90%, 95%, 98%, or 100% sequence identity or similarity, to the reference nucleotide sequence. Such differences can be due to genetic differences between individuals, such as mutations and polymorphisms of a gene. Differences between nucleotide and amino acid sequences can be determined using available algorithms and programs such as the Smith-Waterman algorithm and the BLAST homology search program (Altschul et al., *J. Mol. Biol.* 215:403–410 (1990)).

A gene expression level of a molecule is intended to mean the amount, accumulation or rate of synthesis of a biomarker gene. The gene expression level can be represented by, for example, the amount or transcription rate of hnRNA or mRNA encoded by a gene. A gene expression level similarly refers to an absolute or relative amount or a synthesis rate determined, for example, under steady-state or non-steady-state conditions.

A polypeptide expression level is intended to mean the amount, accumulation or rate of synthesis of a biomarker polypeptide. The polypeptide expression level can be represented by, for example, the amount or rate of synthesis of the polypeptide, a precursor form or a post-translationally modified form of the polypeptide. Various biochemical forms of a polypeptide resulting from post-synthetic modifications can be present in cell contained in a sample. Such modifications include post-translational modifications, proteolysis, and formation of macromolecular complexes. Post-translational modifications of polypeptides include, for example, phosphorylation, lipidation, prenylation, sulfation, hydroxylation, acetylation, addition of carbohydrate, addition of prosthetic groups or cofactors, formation of disulfide bonds and the like. In addition, it is understood that fragments of a polypeptide are included within the definition of a polypeptide expression level. Fragments can include, for example, amino terminal, carboxyl terminal, or internal deletions of a full length polypeptide. Accumulation or synthesis rate with or without such modifications is included with in the meaning of the term. Similarly, a polypeptide expression level also refers to an absolute amount or a synthesis rate of the polypeptide determined, for example, under steady-state or non-steady-state conditions.

As used herein, the term "reference level" refers to a control level of expression of a biomarker used to evaluate a test level of expression of a biomarker in a neoplastic cell-containing sample of a patient. For example, when the level of TUCAN in the neoplastic cells of a patient are higher than the reference level of TUCAN, the cells will be considered to have a high level of expression, or overproduction, of TUCAN. Conversely, when the level of TUCAN in the neoplastic cells of a patient are lower than the reference level, the cells will be considered to have a low level of expression, or underproduction, of TUCAN.

The reference level can be determined by a plurality of methods, provided that the resulting reference level accurately provides a level of a biomarker above which exists a first group of patients having a different probability of survival than that of a second group of patients having levels of the biomarker below the reference level. The reference level can be determined by, for example, measuring the level of expression of a biomarker in non-tumorous cancer cells from the same tissue as the tissue of the neoplastic cells to be tested. The reference level can also be a level of a biomarker of in vitro cultured cells which can be manipulated to simulate tumor cells, or can be manipulated in any other manner which yields expression levels which accurately determine the reference level.

The reference level can also be determined by comparison of the level of a biomarker, such as TUCAN, in populations of patients having the same cancer. This can be accomplished, for example, by histogram analysis, in which an entire cohort of patients are graphically presented, wherein a first axis represents the level of the biomarker, and a second axis represents the number of patients in the cohort whose neoplastic cells express the biomarker at a given level. Two or more separate groups of patients can be determined by identification of subsets populations of the cohort which have the same or similar levels of the biomarker. Determination of the reference level can then be made based on a level which best distinguishes these separate groups. A reference level also can represent the levels of two or more markers. Two or more markers can be represented, for example, by a ratio of values for levels of each biomarker.

The reference level can be a single number, equally applicable to every patient, or the reference level can vary, according to specific subpopulations of patients. For example, older men might have a different reference level than younger men for the same cancer, and women might have a different reference level than men for the same cancer. Furthermore, the reference level can be some level determined for each patient individually. For example, the reference level might be a certain ratio of a biomarker in the neoplastic cells of a patient relative to the biomarker levels in non-tumor cells within the same patient. Thus the reference level for each patient can be proscribed by a reference ratio of one or more biomarkers, such as TUCAN, wherein the reference ratio can be determined by any of the methods for determining the reference levels described herein.

As used herein, the term "neoplastic cell" refers to any cell that is transformed such that it proliferates without normal homeostatic growth control. Such cells can result in a benign or malignant lesion of proliferating cells. Such a lesion can be located in a variety of tissues and organs of the body. Table 1, below, provides a list of exemplary types of cancers from which a neoplastic cell can be derived.

As used herein, the term "cancer" is intended to mean a class of diseases characterized by the uncontrolled growth of aberrant cells, including all known cancers, and neoplastic conditions, whether characterized as malignant, benign, soft tissue or solid tumor. Specific cancers include digestive and gastrointestinal cancers, such as anal cancer, bile duct cancer, gastrointestinal carcinoid tumor, colon cancer, esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; CNS cancer; leukemia and melanoma. By exemplification, a list of known cancers is provided below in Table 1.

TABLE 1

| Types of Cancer |
|---|
| HEMATOPORETIC NEOPLASMS |
| Lymphoid Neoplasms |
| Myeloid Neoplasms |
| Histiocytoses |
| Precursor B lymphoblastic leukemia/lymphoma (ALL) |
| Precursor T lymphoblastic leukemia/lymphoma (ALL) |
| Chronic lymphocytic leukemia/small lymphocytic lymphoma (SLL) |
| Lymphoplasmacytic lymphoma |
| Mantle cell lymphoma |
| Follicular lymphoma |
| Marginal zone lymphoma |
| Hairy cell leukemia |
| Plasmacytoma/plasma cell |

TABLE 1-continued

| Types of Cancer |
| --- |
| myeloma |
| Diffuse large B-cell lymphoma |
| Burkitt lymphoma |
| T-cell chronic lymphocytic leukemia |
| Large granular lymphocytic leukemia |
| Mycosis fungoids and sezary syndrome |
| Peripheral T-cell lymphoma, unspecified |
| Angioimmunoblastic T-cell lymphoma |
| Angiocentric lymphoma (NK/T-cell lymphoma) |
| Intestinal T-cell lymphoma |
| Adult T-cell leukemia/lymphoma |
| Anaplastic large cell lymphoma |
| Hodgkin Diseases (HD) |
| Acute myclogenous leukemia (AML) |
| Myclodysplastic syndromes |
| Chronic Myclofroliferative Disorders |
| Chronic Myclogenous Leukemia (CML) |
| Polycythemia Vera |
| Essential Thrombocytosis |
| Myelofibrosis with Myeloid Metaplasia |
| Hemangioma |
| Lymphangioma |
| Glomangioma |
| Kaposi Sarcoma |
| Hemanioendothelioma |
| Angiosarcoma |
| Hemangiopericytoma |
| HEAD & NECK |
| Basal Cell Carcinoma |
| Squamous Cell Carcinoma |
| Ceruminoma |
| Osteoma |
| Nonchromaffin Paraganglioma |
| Acoustic Neurinoma |
| Adenoid Cystic Carcinoma |
| Mucoepidermoid Carcinoma |
| Malignant Mixed Tumors |
| Adenocarcinoma |
| Lymphoma |
| Fibrosarcoma |
| Osteosarcoma |
| Chondrosarcoma |
| Melanoma |
| Olfactory Neuroblastoma |
| Isolated Plasmocytoma |
| Inverted Papillomas |
| Undifferentiated Carcinoma |
| Mucoepidermoid Carcinoma |
| Acinic Cell Carcinoma |
| Malignant Mixed Tumor |
| Other Carcinomas |
| Amenoblastoma |
| Odontoma |
| THYMUS |
| Malignant Thymoma |
| Type I (Invasive thymoma) |
| Type II (Thymic carcinoma) |
| Squamous cell carcinoma |
| Lymph epithelioma |
| THE LUNG |
| Squamous Cell Carcinoma |

TABLE 1-continued

| Types of Cancer |
| --- |
| Adenocarcinoma |
| Bronchial derived |
| Acinar; papillary; solid |
| Bronchioalveolar |
| Small Cell Carcinoma |
| Oat Cell |
| Intermediate Cell |
| Large Cell Carcinoma |
| Undifferentiated; giant cell; clear cell |
| Malignant Mesothelioma |
| Sarcomotoid Type |
| Epithelial Type |
| THE GASTROINTESTINAL TRACT |
| Squamous Cell Carcinoma |
| Adenocarcinoma |
| Carcinoid |
| Malignant Melanoma |
| Adenocarcinoma |
| Gastric Carcinoma |
| Gastric Lymphoma |
| Gastric Stromal Cell Tumors |
| Lymphoma |
| Kaposi's Sarcoma |
| Intestinal Stromal Cell Tumors |
| Carcinids |
| Malignant Mesethelioma |
| Non-mucin producing adenocarcinoma |
| THE LIVER AND THE BILIARY TRACT |
| Hepatocellular Carcinoma |
| Cholangiocarcinoma |
| Hepatoblastoma |
| Angiosarcoma |
| Fibrolameller Carcinoma |
| Carcinoma of the Gallbladder |
| Adenocarcinoma |
| Squamous Cell Carcinoma |
| Papillary, poorly differentiated |
| THE PANCREAS |
| Adenocarcinoma |
| Cystadenocarcinoma |
| Insulinoma |
| Gastrinoma |
| Glucagonamoa |
| THE KIDNEY |
| Renal Cell Carcinoma |
| Nephroblastoma (Wilm's Tumor) |
| THE LOWER URINARY TRACT |
| Urothelial Tumors |
| Squamous Cell Carcinoma |
| Mixed Carcinoma |
| Adenocarcinoma |
| Small Cell Carcinoma |
| Sarcoma |
| THE MALE GENITAL TRACT |
| Squamous Cell CarcinomaSarcinoma |
| Speretocytic Sarcinoma |
| Embyonal Carcinoma |
| Choriocarcinoma |
| Teratoma |
| Leydig Cell Tumor |
| Sertoli Cell Tumor |
| Lymphoma |
| Adenocarcinoma |
| Undifferentiated Prostatic |

TABLE 1-continued

| Types of Cancer |
| --- |
| Carcinoma |
| Ductal Transitional |
| Carcinoma |
| THE FEMALE GENITAL TRACT |
| Squamous Cell Carcinoma |
| Basal Cell Carcinoma |
| Melanoma |
| Fibrosarcoma |
| Intaepithelial Carcinoma |
| Adenocarcinoma Embryonal |
| Rhabdomysarcoma |
| Large Cell Carcinoma |
| Neuroendocrine or Oat Cell |
| Carcinoma |
| Adenocarcinoma |
| Adenosquamous Carcinoma |
| Undifferentiated Carcinoma |
| Carcinoma |
| Adenoacanthoma |
| Sarcoma |
| Carcinosarcoma |
| Leiomyosarcoma |
| Endometrial Stromal Sarcoma |
| Serous Cystadenocarcinoma |
| Mucinous Cystadenocarcinoma |
| Endometrioid Tumors |
| Adenosarcoma |
| Celioblastoma (Brenner |
| Tumor) |
| Clear Cell Carcinoma |
| Unclassified Carcinoma |
| Granulosa-Theca Cell Tumor |
| Sertoli-Leydig Cell Tumor |
| Disgerminoma |
| Teratoma |
| THE BREAST |
| Phyllodes Tumor |
| Sarcoma |
| Paget's Disease |
| Carcinoma |
| Insitu Carcinoma |
| Invasive Carcinoma |
| THE ENDOCRINE SYSTEM |
| Adenoma |
| Carcinoma |
| Meningnoma |
| Cramiopharlingioma |
| Papillary Carcinoma |
| Follicular Carcinoma |
| Medullary Carcinoma |
| Anoplastic Carcinoma |
| Adenoma |
| Carcinoma |
| Pheochromocytoma |
| Neuroblastome |
| Paraganglioma |
| Pineal |
| Pineoblastoma |
| Pineocytoma |
| THE SKIN |
| Melanoma |
| Squamous cell carcinoma |
| Basal cell carcinoma |
| Merkel cell carcinoma |
| Extramamary Paget's Disease |
| Paget's Disease of the |
| nipple |
| Kaposi's Sarcoma |
| Cutaneous T-cell lymphoma |
| BONES, JOINTS, AND SOFT TISSUE TUMORS |
| Multiple Myeloma |
| Malignant Lymphoma |

TABLE 1-continued

| Types of Cancer |
| --- |
| Chondrosacrcoma |
| Mesenchymal Chondrosarcoma |
| Osteosarcoma |
| Ewing Tumor (Ewing Sarcoma) |
| Malignant Giant Cell Tumor |
| Adamantinoma |
| Malignant Fibrous |
| Histiocytoma |
| Desmoplastc Fibroma |
| Fibrosarcoma |
| Chordoma |
| Hemangioendothelioma |
| Memangispericytoma |
| Liposarcoma |
| Malignant Fibrous |
| Histiocytoma |
| Rhabdomysarcoms |
| Leiomyosarcoma |
| Angiosarcoma |
| NERVOUS SYSTEM |
| Schwannoma |
| Neurofibroma |
| Malignant Periferal Nerve |
| Sheath Tumor |
| Astrocytoma |
| Fibrillary Astrocytoma |
| Glioblastoma Multiforme |
| Brain Stem Glioma |
| Pilocytic Astrocytoma |
| Pleomorphic |
| Xanthorstrocytoma |
| Oligodendroglioma |
| Ependymoma |
| Gangliocytoma |
| Cerebral Neuroblastoma |
| Central Neurocytoma |
| Dysembryoplastic |
| Neuroepithelial Tumor |
| Medulloblastoma |
| Malignant Meningioma |
| Primary Brain Lymphoma |
| Primary Brain Germ Cell |
| Tumor |
| THE EYE |
| Carcinoma |
| Squamous Cell Carcinoma |
| Mucoepidermoid Carcinoma |
| Melanoma |
| Retinoblastoma |
| Glioma |
| Meningioma |
| THE HEART |
| Myxoma |
| Fibroma |
| Lipoma |
| Papillary Fibroelastoma |
| Rhasdoyoma |
| Angiosarcoma |
| Other Sarcoma |
| HISTIOCYTOSES |
| Langerhans Cell |
| Histiocytosis |

As used herein, the term "specifically reactive" when used in reference to an antibody refers to the discriminatory binding of the antibody to the indicated target polypeptide. For such binding to be discriminating, the antibody will not substantially cross react with other polypeptides. Specific reactivity can include binding properties such as binding specificity, binding affinity and binding avidity. For example, an antibody can bind a target polypeptide with a binding affinity (Kd) of about $10^{-4}$ M or more, $10^{-6}$ M or more, $10^{-7}$ M or more, $10^{-8}$ M or more, $10^{-9}$ M or more, or $10^{-10}$ M or more. Several methods for detecting or measuring antibody binding are known in the art and disclosed herein.

As used herein, the term "sample" is intended to mean any biological fluid, cell, tissue, organ or portion thereof, that includes or potentially includes a neoplastic cell, such as a cell from the colon, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation.

As used herein, the term "disease-free survival" refers to the lack of tumor recurrence and/or spread and the fate of a patient after diagnosis, for example, a patient who is alive without tumor recurrence. The phrase "overall survival" refers to the fate of the patient after diagnosis, regardless of whether the patient has a recurrence of the tumor.

As used herein, the term "risk of recurrence" refers to the probability of tumor recurrence or spread in a patient subsequent to diagnosis of cancer, wherein the probability is determined according to the process of the invention.

Tumor recurrence refers to further growth of neoplastic or cancerous cells after diagnosis of cancer. Particularly, recurrence can occur when further cancerous cell growth occurs in the cancerous tissue. Tumor spread refers to dissemination of cancer cells into local or distant tissues and organs, for example during tumor metastasis. Tumor recurrence, in particular, metastasis, is a significant cause of mortality among patients who have undergone surgical treatment for cancer. Therefore, tumor recurrence or spread is correlated with disease-free and overall patient survival.

The invention relates to the use of TUCAN as a biomarker for prognosing survival and monitoring the effectiveness of a treatment for a cancer patient. TUCAN is a CARD domain-containing protein that has a role in regulating apoptosis. Apoptosis is a physiologic process that ensures homeostasis is maintained between cell production and cell turnover in essentially all self-renewing tissues. In addition to maintaining tissue homeostasis, apoptosis also occurs in response to a variety of external stimuli, including growth factor deprivation, alterations in calcium levels, free-radicals, cytotoxic lymphokines, infection by some viruses, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral infections, induction of apoptosis can figure prominently in the pathophysiology of the disease process, because immune-based eradication of viral infections depends on elimination of virus-producing host cells by immune cell attack resulting in apoptosis.

The principal effectors of apoptosis are a family of intracellular proteases known as Caspases, representing an abbreviation for Cysteine Aspartyl Proteases. Caspases are found as inactive zymogens in essentially all animal cells. During apoptosis, the caspases are activated by proteolytic processing at specific aspartic acid residues, resulting in the production of subunits that assemble into an active protease typically consisting of a heterotetramer containing two large and two small subunits (Thornberry and Lazebnik, *Science* 281:1312–1316 (1998)). The phenomenon of apoptosis is produced directly or indirectly by the activation of caspases in cells, resulting in the proteolytic cleavage of specific substrate proteins.

TUCAN contains at least two protein domains, one of which is a CARD (Caspase-Associated Recruitment Domain). CARDs are protein interaction motifs found in the N-terminal prodomains of several caspases and in apoptosis-regulatory proteins that either activate or suppress activation of CARD-containing pro-caspases. In mammals, eight CARD-carrying caspases have been identified, including pro-caspases-1, 2, 4, 5, 9, 11, 12 and 13. To date, multiple non-caspase CARD-containing proteins have been discovered and functionally characterized, including Apaf1, Nod1 (CARD4), NAC (DEPCAP), Raidd (CRADD), Cardiak (Rip2, RICK), BcllO (CIPER), ARC (Nop30), Asc, CARD9, CARD10, CARD11, CARD14, cIAP1, cIAP2, and CLAN. The CARD domains of many of these proteins are capable of binding the CARD-containing prodomains of specific CARD-carrying caspases, either facilitating or inhibiting protease activation.

The CARD domain of TUCAN selectively binds to its own CARD and to pro-Caspase-9 (see Example IX). In addition, the binding of TUCAN to pro-caspase-9 has been shown to interfere with the ability of pro-caspase-9 to interact with Apaf1. By inhibiting the interaction between pro-caspase-9 and Apaf1, TUCAN inhibits apoptosis signaling in the mitochondrial/cytochrome c pathway. Consistent with this observation is that finding that over-expression of TUCAN reduces apoptosis induced by stimuli that are known to activate the mitochondrial pathway for caspase-activation, including Bax, DNA-damaging drugs, and staurosporine. In contrast, apoptosis induced via alternative pathways, including GraB and Fas (TNF-family death receptor), is not inhibited by TUCAN. Further, over-expression of TUCAN in cells by stable or transient transfection inhibits apoptosis and caspase activation induced by Apaf1/caspase-9-dependent stimuli, including Bax, VP16, and Staurosporine, but not by Apaf1/caspase-9-independent stimuli, Fas and Granzyme B. These cellular functions of TUCAN indicate that it has an important role in inhibiting mitochondrial signaling pathway-induced apoptosis.

TUCAN also contains an N-terminal domain that shares amino-acid similarity with a segment of the NAC protein, a CARD-carrying regulator of the Apaf1 apoptosome Chu et al. *J Biol Chem* 276:9239–9245 (2001) and Hlaing et al. *J Biol Chem* 276:9230–9238 (2001)). The TUCAN N-terminal domain contains several candidate phosphorylation sites, including PKC (S/T-x-R/K) sites at amino-acids 72, 286, 313, and 416, Casein kinase II (S/T-x-D/E) sites at 289, 376, 398, 414, and 416 and MAP kinase/CDK (S/T-P) sites at 187 and 289. The observed multiple forms of TUCAN identified by their different mobilities in SDS-PAGE experiments (see FIG. 6B, for example) could be differently phosphorylated forms of TUCAN. TUCAN also contains a candidate caspase cleavage site (DEED) at residues 243–246.

These and other molecular characteristics and cellular functions of TUCAN are described, for example, in Pathan et al. *J. Biol. Chem.* 276:32220–32229 (2001), the entirety of which is incorporated herein by reference.

As disclosed herein in Example VII, relatively high levels of TUCAN are found in several human cancer cell lines. Moreover, as disclosed in Examples II and VIII, compared to normal colonic mucosa, TUCAN immunostaining was pathologically elevated in roughly two-thirds of early-stage colon cancers, indicating abnormal over-expression of this anti-apoptotic protein in association with malignant transformation. Studies of cells derived from pro-caspase-9 knock-out mice have indicated that pro-caspase-9 functions as a tumor suppressor in a p53-dependent pathway (Soengas et al. Science 284:156–159 (1999)). In view of the role of TUCAN in regulating pro-caspase-9, over-expression of TUCAN can be functionally equivalent to loss of pro-caspase-9, indicating that elevated levels of TUCAN can promote tumor pathogenesis or progression. As shown herein in Examples IV and VIII, colon cancer patients whose tumors contained higher levels of TUCAN indeed were more likely to die from their disease, based on retrospective analysis using archival specimens.

Therefore, the invention provides a method for determining a prognosis for survival for a cancer patient using TUCAN. The method involves (a) measuring a level of a TUCAN in a neoplastic cell-containing sample from the cancer patient, and (b) comparing the level of TUCAN in the sample to a reference level of TUCAN, wherein low levels of TUCAN in the sample correlate with increased survival of the patient.

A level of TUCAN in a neoplastic cell-containing sample that exceeds a determined basal level, or reference level, of TUCAN can be a significant factor in tumor recurrence or spread. When tumor cell determined reference levels are exceeded, the level of TUCAN is characterized as high or overproduced. High or overproduced TUCAN can be indicative of increased risk of tumor recurrence or spread. Low or underproduced TUCAN can be indicative of decreased risk or tumor recurrence or spread.

The methods of the invention for prognosing survival for a cancer patient involve obtaining a sample from a patient and measuring the level of one or more biomarkers, such as TUCAN. The level of the biomarker, such as TUCAN, is used to determine the prognosis for disease-free or overall survival of a cancer patient based on the correlations provided herein. Such prognosis is possible because the likelihood of tumor recurrence or spread correlates with the level of TUCAN in a tumor cell. For example, as shown in Examples VI and VIII, it has been found that when the levels of TUCAN expression are low, the likelihood of cancer recurrence is low. The level of TUCAN in a neoplastic-cell containing sample from a patient can be used as the sole factor in assessing disease status or can be used in addition to other predictive methods.

TUCAN can be used to prognose survival or monitor the effectiveness of a course of treatment for patients suffering from a variety of types of cancer. As described in Example VII, TUCAN is present in multiple different cancer cell types, including leukemia, melanoma and breast, ovarian, lung, CNS, prostate and renal cancers. Also as described above, a cellular function of TUCAN is suppression of mitochondrial signaling pathway-induced apoptosis. Mitochondrial signaling pathway-induced apoptosis is an apoptotic mechanism that can occur in any cell type, and that can become dysregulated or suppressed in any type cell, resulting in transformation of a cell such that it proliferates without normal homeostatic growth control. Therefore, a level of TUCAN can be correlated with tumor recurrence or survival of a patient having any type of cancer. Using the guidance provided herein and other well-known methods, those skilled in the art will be able to determine if a level of TUCAN in a particular tumor cell type correlates with patient survival. Having determined a correlation between a reference level of TUCAN and survival of a cancer patient, those skilled in the art can practice the methods for determining the prognosis for survival for a cancer patient and the method for monitoring the effectiveness of a course of treatment for a patient with cancer described herein.

In the methods of the invention, a sample can be, for example, a cell or tissue obtained using a biopsy procedure or can be a fluid sample containing cells, such as blood, serum, semen, urine, or stool. Those skilled in the art will be able to determine an appropriate sample, which will depend on cancer type, and an appropriate method for obtaining a biopsy sample, if necessary. When possible, it can be preferable to obtain a sample from a patient using the least invasive collection means. For example, obtaining a fluid sample from a patient, such as blood, saliva, serum, semen, urine or stool, is less invasive than collecting a tissue sample.

In one embodiment, a level of TUCAN can be determined by measuring the amount of a TUCAN using a selective binding agent, such as an antibody specifically reactive with a TUCAN polypeptide. Other selective binding agents include polypeptides that bind to a TUCAN polypeptide, such as a TUCAN polypeptide that contains the TUCAN CARD domain (amino acids 345–431 (SEQ ID NO:3)), and a caspase 9 polypeptide, the amino acid sequence of which (SEQ ID NO:4) is referenced as P55211 in the Prosite database, or modifications thereof that bind to a TUCAN polypeptide. Selective binding of TUCAN to pro-caspase and to itself is described in Example IX.

Essentially all modes of affinity binding assays are applicable for use in determining a level of TUCAN, or another biomarker polypeptide, such as cIAP2, Apaf1, Smac, β-catenin, Bcl-2 or p53, in a sample. Such methods are rapid, efficient and sensitive. Moreover, affinity binding methods are simple and can be modified to be performed under a variety of clinical settings and conditions to suit a variety of particular needs. Affinity binding assays that are known and can be used in the methods of the invention include both soluble and solid phase formats. A specific example of a soluble phase affinity binding assay is immunoprecipitation using a biomarker selective antibody or other binding agent. Solid phase formats are advantageous for the methods of the invention since they are rapid and can be performed more easily on multiple different samples simultaneously without losing sensitivity or accuracy. Moreover, solid phase affinity binding assays are further amenable to high throughput screening and automation.

Specific examples of solid phase affinity binding assays include immunohistochemical binding assays, immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody binding molecules that is selective for the analyte or ligand of interest, essentially any binding agent can be alternatively substituted for the selectively binding antibody. Such binding agents include, for example, macromolecules such as polypeptides, peptides, nucleic acid molecules, lipids and sugars as well as small molecule compounds. Methods are known in the art for identifying such molecules which bind selectively to a particular analyte or ligand and include, for example, surface display libraries and combinatorial libraries. Thus, for a molecule other than an antibody to be used in an affinity binding assay, all that is necessary is for the binding agent to exhibit selective binding activity for a biomarker.

The various modes of affinity binding assays, such as immunoaffinity binding assays, include, for example, immunohistochemistry methods, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

An antibody useful in the methods of the invention includes a polyclonal and monoclonal antibody, as well as an antigen binding fragment of such antibodies. Methods of preparing polyclonal or monoclonal antibodies are well known to those skilled in the art and are described in Example I and in Harlow and Lane, *Antibodies: A Laboratory Manual*, Cold Spring Harbor Laboratory Press (1988).

An antibody useful in the methods of the invention also includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275–1281 (1989)). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, supra, 1988); Hilyard et al., *Protein Engineering: A practical approach* (IRL Press 1992); Borrabeck, *Antibody Engineering,* 2d ed. (Oxford University Press 1995)).

Formats employing affinity binding can be used in conjunction with a variety of detection labels and systems known in the art to quantitate amounts of biomarkers in the analyzed sample. Detection systems include the detection of bound biomarker by both direct and indirect means. Direct detection methods include labeling of the biomarker-specifically reactive antibody or binding agent. Indirect detection systems include, for example, the use of labeled secondary antibodies and binding agents.

Secondary antibodies, labels and detection systems are well known in the art and can be obtained commercially or by techniques well known in the art. The detectable labels and systems employed with the biomarker-selective binding agent should not impair binding of the agent to the biomarker. Moreover, multiple antibody and label systems can be employed for detecting the bound biomarker-specifically reactive antibody to enhance the sensitivity of the binding assay if desired.

Detectable labels can be essentially any label that can be quantitated or measured by analytical methods. Such labels include, for example, enzymes, radioisotopes, fluorochromes as well as chemi- and bioluminescent compounds. Specific examples of enzyme labels include horseradish peroxidase (HRP), alkaline phosphatase (AP), β-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. A particularly useful fluorochrome is fluorescein or rhodamine.

Chemiluminescent as well as bioluminescent detection labels are convenient for sensitive, non-radioactive detection of a biomarker and can be obtained commercially from various sources such as Amersham Lifesciences, Inc. (Arlington Heights, Ill.).

Alternatively, radioisotopes can be used as detectable labels in the methods of the invention. Iodine-125 is a specific example of a radioisotope useful as a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The prognostic formats of the present invention can be forward, reverse or simultaneous as described in U.S. Pat. No. 4,376,110 and No. 4,778,751. Separation steps for the various assay formats described herein, including the removal of unbound secondary antibody, can be performed by methods known in the art (Harlow and Lane, supra). For example, washing with a suitable buffer can be followed by filtration, aspiration, vacuum or magnetic separation as well as by centrifugation.

A binding agent selective for a biomarker also can be utilized in imaging methods that are targeted at biomarker-expressing neoplastic cells. These imaging techniques will have utility in identification of residual neoplastic cells at the primary site following standard treatments including, for example, surgical resection of an organ of the gastrointestinal system, such as the colon, and radiation therapy. In addition, imaging techniques that detect neoplastic cells have utility in detecting secondary sites of metastasis. The biomarker specific binding agent can be radiolabeled with, for example, $^{111}$indium and infused intravenously as described by Kahn et al., *Journal of Urology* 152:1952–1955 (1994). The binding agent selective for a biomarker can be, for example, a monoclonal antibody specifically reactive with TUCAN or another biomarker, such as cIAP2, Apaf1, Smac, β-catenin, Bcl-2 or p53. Imaging can be accomplished by, for example, radioimmunoscintigraphy as described by Kahn et al., supra.

The level of TUCAN, or another biomarker, such as cIAP2, Apaf1, Smac, β-catenin, Bcl-2 or p53, also can be determined by measuring the amount of a biomarker mRNA or DNA using a binding agent selective for the biomarker, such as a nucleic acid probe. The methods used to detect mRNA levels include detection of hybridization or amplification of mRNA encoding the biomarker. This detection can be carried out by analysis of mRNA either in vitro or in situ using one of the methods known to one of ordinary skill in the art as exemplified in the Current Protocols in Molecular Biology (John Wiley & Sons, 1999); in U.S. Pat. No. 5,882,864; and the like. A TUCAN mRNA, or other biomarker mRNA, detected will be any RNA transcript of a TUCAN gene, or fragment thereof, or cIAP2, Bcl-2, p53, β-catenin, survivin or Apaf1 gene, or fragment thereof.

There are numerous methods well known in the art for detecting nucleic acid molecules by specific or selective hybridization with a complementary probe. Briefly, for detection by hybridization, a TUCAN nucleic acid probe complementary to a TUCAN gene, having a detectable label is added to a neoplastic cell-containing sample obtained from the individual having, or suspected of having cancer under conditions which allow annealing of the probe to TUCAN RNA. Methods for detecting TUCAN RNA in a sample can include the use of, for example, RT-PCR. Conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled. Following annealing, the sample is washed and the signal is measured and compared with a suitable control or standard value. The magnitude of the hybridization signal is directly proportional to the mRNA level of TUCAN. A level of TUCAN mRNA in a neoplastic cell-containing sample is compared to a suitable reference level for TUCAN mRNA. The levels of other biomarker mRNA, such as cIAP2, Apaf1, Smac, β-catenin, Bcl-2 or p53, can be similarly determined and compared to a suitable reference level for the particular biomarker.

Other examples of methods include PCR and other amplification methods such as RT-PCR, 5' or 3' RACE, RNase protection, RNA blot, dot blot or other membrane-based technologies, dip stick, pin, ELISA or two-dimensional arrays immobilized onto a solid support. These methods can be performed using either qualitative or quantitative measurements, all of which are well known to those skilled in the art.

PCR or RT-PCR can be used with isolated RNA or crude cell lysate preparations. PCR is advantageous when there is limiting amounts of starting material. A further description of PCR methods can be found in, for example, Dieffenbach, C. W., and Dveksler, G. S., *PCR Primer: A Laboratory Manual*, Cold Spring Harbor Press, Plainview, N.Y. (1995). Multisample formats such as microarrays offer the advantage of analyzing numerous, different samples in a single assay. In contrast, solid-phase dip stick-based methods offer the advantage of being able to rapidly analyze a patient's fluid sample for an immediate result.

Nucleic acid probes useful for measuring the expression level of a biomarker, such as cIAP2, TUCAN, Apaf1, β-catenin, Bcl-2, or Smac by hybridization include, for example, probes prepared using the nucleotide sequences provided herein. Nucleic acid molecules corresponding to the entire cDNA sequences and fragments thereof, including oligonucleotides corresponding to cIAP2, TUCAN, Apaf1, β-catenin, Bcl-2, or Smac nucleotide sequences and which are capable of specifically or selectively hybridizing to cIAP2, TUCAN, Apaf1, β-catenin, Bcl-2, or Smac RNA, are useful for hybridization methods.

A reference level is a level a biomarker, such as cIAP2, TUCAN, Apaf1, Smac, β-catenin, of Bcl-2, used to evaluate the level of the biomarker in cancerous cells of a patient. Specifically, when the level of a biomarker in the cancerous cells of a patient are higher than the reference level, the cells will be considered to have a high level of, or overproduction, of the biomarker. Conversely, when the level of biomarker in the cancerous cells of a patient are lower than the reference level, the cells will be considered to have a low level of, or underproduction, of the biomarker.

A high level of a biomarker, such as cIAP2, TUCAN, Apaf1, Smac, β-catenin, Bcl-2 or p53, or overproduction of a biomarker gene is related to a level of the biomarker above a determined basal level. Thus, a reference or basal level of a biomarker, such as cIAP2, TUCAN, Apaf1, Smac, β-catenin, Bcl-2 or p53, in a cancer cell is identified as a "cutoff" value, above which there is a significant correlation between the presence of the biomarker and increased or decreased tumor recurrence or spread. Those of skill in the art will recognize that some "cutoff" values are not sharp in that clinical correlations are still significant over a range of values on either side of the cutoff; however, it is possible to select an optimal cutoff value (for example varying H-scores, and the like) of a level of a biomarker for a cancer cell type. It is understood that improvements in optimal cutoff values could be determined, depending on the sophistication of statistical methods used and on the number and source of samples used to determine reference or basal values.

Such overproduction is not typically calculated in terms of absolute biomarker levels, but is determined using relative measurements. These relative measurements are illustrated for quantitation purposes with an internal standard; however, it will be appreciated that other standards or methods of determination can be used, such as comparison with external standards, biomarker polypeptide measurements, biomarker mRNA measurements, absolute values of protein, mRNA or DNA levels, and the like.

A reference level can also be determined by comparison of biomarker levels in populations of patients having cancer, such as patients having cancer of the same stage. This can be accomplished by histogram analysis, in which the entire cohort of patients tested are graphically presented, wherein a first axis represents the level of a biomarker, and a second axis represents the number of patients in the cohort whose tumor cells contain the biomarker at a given level. Two or more separate groups of patients can be determined by identification of subsets populations of the cohort which have the same or similar levels of the biomarker. Determination of the reference level can then be made based on a biomarker level that best distinguishes these separate groups.

Verification that the reference level distinguishes the likelihood of tumor recurrence or spread in cancer patients expressing below-reference biomarker levels versus cancer patients expressing above-reference biomarker levels can be carried out using single variable or multi-variable analysis. These methods determine the likelihood of a correlation between one or more variables and a given outcome. In the specific case, the methods will determine the likelihood of a correlation between a biomarker levels (or biomarker level coupled with another variable) and disease-free or overall survival of cancer patients. Any one of a plurality of methods well known to those of ordinary skill in the art for carrying out these analyses can be used. Examples of single variable analysis is the Kaplan-Meir method or the log-rank test. An example of multi-variable analysis is the Cox proportional-hazards regression model (see, for example, Example VI).

Population-based determination of reference levels, for example, by histogram analysis can be carried out using a cohort of patients sufficient in size in order to determine two or more separate groups of patients having different biomarker levels. Typically, such a cohort comprises at least 25 patients, such as at least 50 patients, including at least 75 patients, and at least 100 patients. Similarly, verification of determined reference levels can also comprise at least 25 patients, such as at least 50 patients, including at least 75 patients, and at least 100 patients.

The reference level can be a single number, equally applicable to every patient, or the reference level can vary according to specific subpopulations of patients. For example, men might have a different reference level than women for the same cancer. Furthermore, the reference level can be a level determined for each patient individually. For example, the reference level might be a certain ratio of a biomarker level in the tumor cells of a patient relative to the biomarker level in non-tumor cells within the same patient. Thus the reference level for each patient can be proscribed by a reference ratio of biomarker levels, wherein the reference ratio can be determined by any of the methods for determining the reference levels described above.

Further, while a reference level can separate two groups of patients, it is within the scope of the invention that numerous reference values might exist which separate a plurality of populations. For example, two reference values can separate a first group of patients with high levels of a biomarker from a second group of patients with intermediate levels the biomarker, and from a third group of patients with low levels of the biomarker. The number of different reference levels can be sufficient to proscribe a curve, such as a continuous line, which describes the likelihood of disease-free or overall survival in a patient as a function of the biomarker level in that patient. Such a curve will constitute a "continuous" biomarker level, where the likelihood of disease free or overall survival in a patient is proportional to the biomarker level in that patient. Two or more biomarker levels also can be represented by such a curve.

The reference level can also represent the level of a biomarker protein, such as cIAP2, TUCAN, Apaf1, Smac, β-catenin, Bcl-2 or p53, in one or more compartments of the cell. Typically, the reference level will represent the level of biomarker protein in (a) the whole cell, (b) the nucleus, or (c) the cytosol. This level will be useful when cell compartmentalization of the protein correlates with the risk of tumor recurrence or spread of a certain cancer. Similarly, the reference level can be a ratio of levels of biomarker protein in the different compartments (for example, the ratio of nuclear biomarker protein to whole cell biomarker protein, or the ratio of nuclear to cytosolic biomarker protein).

The reference level of a biomarker, such as cIAP2, TUCAN, Apaf1, or Smac, can further be used in conjunction with another variable found to be a statistically significant indicator of the likelihood of disease-free or overall survival for cancer. Such indicators include the presence or levels of known cancer markers (for example, colon cancer markers include sialosyl-TnCEA, CA19-9, and LASA), or can be clinical or pathological indicators (for example, age, tumor size, tumor histology, clinical stage, family history and the like). For example, clinical stage of the cancer is also a statistically significant indicator of disease-free or overall survival, wherein the reference level of a biomarker can vary according to the clinical stage of the cancer. For example, the level of a biomarker, such as a low level of TUCAN, in conjunction with clinical stage II of a cancer for a given patient, together are indicators for increased likelihood of disease free or overall survival. Hence, the reference level of a biomarker can vary as a function of another statistically significant indicator of disease-free or overall survival for cancer.

The levels of biomarkers, such as cIAP2, Apaf1, TUCAN, Bcl-2 and Smac, in a cancer cell can correlate with each other and with other molecules because these molecules participate in common dysregulated molecular pathways that contribute to the hyperproliferative state of a cancer cell. Therefore a combination of TUCAN with one or more additional biomarkers can be used in the methods of the invention for determining a prognosis for survival for a cancer patient. A second or additional biomarker can be, for example, Apaf1, cIAP1, cIAP2, survivin, AIF, Bcl-2, Bcl-XL, Bax, Bid, BAG1, p53, mutant p53, β-catenin, MIB-1 or another well-known tumor marker, such as the exemplary commercially available tumor markers described below. Furthermore, the use of a combination of TUCAN with one or more biomarkers can provide increased prognostic significance or confidence in a prognostic determination.

Therefore, the invention provides a method for determining a prognosis for survival for a cancer patient that involves the use of two or more biomarkers. The method is practiced by (a) measuring the levels of TUCAN and one or more biomarkers selected from the group consisting of cIAP2, Apaf1, Bcl-2 and Smac in a neoplastic cell-containing sample from the cancer patient, and (b) comparing the level of TUCAN and the one or more selected biomarkers in the sample to a reference level of TUCAN and the biomarkers, wherein a low level of TUCAN and a high level of any of Apaf1, Bcl-2 or Smac, or a low level of TUCAN and a low level of cIAP2, in said sample correlate with increased survival of said patient.

The methods of the invention can be practiced, for example, by selecting a combination of TUCAN and one or more biomarkers for which increased or decreased expression correlates with improved survival, such as any of cIAP2, Apaf1, Bcl-2, Smac, or another known or standard biomarker for cancer. The selected biomarker can be a general diagnostic or prognostic marker useful for multiple types of cancer, such as CA 125, CEA or LDH, or can be a cancer-specific diagnostic or prognostic marker, such as a colon cancer marker (for example, sialosyl-TnCEA, CA19-9, or LASA), breast cancer marker (for example, CA 15-2. Her-2/neu and CA 27.29), ovarian cancer marker (for example, CA72-4), lung cancer (for example, neuron-specific enolase (NSE) and tissue polypeptide antigen (TPA)), prostate cancer (for example, PSA, prostate-specific membrane antigen and prostatic acid phosphatase), melanoma (for example, S-100 and TA-90), as well as other biomarkers specific for other types of cancer. Those skilled in the art will be able to select useful diagnostic or prognostic markers for detection in combination with TUCAN. Similarly, three or more, four or more or five or more or a multitude of biomarkers can be used together for determining a prognosis for survival for a cancer patient.

The use of two or more biomarkers can provide increased confidence in prognostic outcome. For example, as disclosed herein, combinations of low cIAP and low TUCAN, and high Apaf1 and low TUCAN were correlated with increased disease-free survival (see Example V). In particular, among 33 patients examined for levels of cIAP and TUCAN in a neoplastic cell-containing sample, 97% of patients having low cIAP and low TUCAN remained alive (91% disease-fee), as opposed to 56% alive and 44% disease-free for other categories of patients. In addition, among 17 patients examined for levels of Apaf1 and TUCAN in a neoplastic cell-containing sample, 100% of patients having high Apaf1 and low TUCAN remained alive and disease-free, as opposed to 65% alive and 53% disease-free for other categories of patients. Those skilled in the art will recognize that such correlations can be observed using other combinations of biomarkers using methods described herein.

Combinations of biomarkers useful in the prognostic methods of the invention include, for example, cIAP2 and TUCAN, Apaf1 and TUCAN, and a multiplicity of other combination of TUCAN with biomarkers such as cIAP2, Apaf1, Bcl-2 and Smac and other molecules, including AIF, Bcl-2, Bcl-XL, Bax, Bid, BAG1, p53, mutant p53, β-catenin, MIB-1 and a variety of other general and tumor-specific biomarkers, such as commercially available diagnostic markers described herein above. Such combinations can be useful indicators of the metastatic state of a cancer cell because elevated levels of these biomarkers was observed in a portion of all cancer specimens evaluated (see Example II). Further, elevated levels of various biomarkers correlated with another colon cancer marker, Ki-67, and positive correlations between the expression of biomarkers was observed, for example, between cIAP2 and TUCAN ($p=0.003$) in patient populations.

The invention also provides a method for monitoring the effectiveness of a course of treatment for a patient with cancer. The method involves (a) determining the level of a TUCAN in a neoplastic cell-containing sample from the cancer patient, and (b) determining the level of TUCAN in a neoplastic cell-containing sample from the patient after treatment, whereby comparison of the TUCAN level prior to treatment with the biomarker level after treatment indicates the effectiveness of the treatment.

As used in the context of a course of treatment, “effectiveness” refers to the ability of the course of treatment to decrease the risk of tumor recurrence or spread and therefore to increase the likelihood of disease-free or overall survival of the patient. This method will have particular utility when the level a biomarker, such as cIAP, TUCAN, Apaf1 or Smac, in the tumor cells of a patient is abnormal compared to the level of cIAP, TUCAN, Apaf1 and Smac in the non-tumor cells of the patient. Comparison of biomarker levels in a neoplastic cell-containing sample from a patient before and after treatment will thereby serve to indicate whether a biomarker level is returning to that of non-tumor cells, implying a more effective course of treatment, or whether a biomarker level is remaining abnormal or increasing in abnormality, implying a less effective course of treatment. For example, an increase in the level of Apaf1, Bcl-2 or Smac in a patient sample after treatment indicates that treatment is effective because high levels of Apaf1 or Smac correlate with a lower incidence of colon cancer recurrence. Further, a low in the level of β-catenin, cIAP2 or TUCAN in a patient sample after treatment indicates that treatment is effective because low levels of β-catenin, cIAP2 or TUCAN correlate with a lower incidence of colon cancer recurrence.

Patients having cancer can be classified according to whether a high level of a particular biomarker, or a low level of the biomarker, is measured in a neoplastic cell-containing sample obtained from the patient. Determination of the prognosis for the patient can be made by determining whether the group to which the patient has been assigned correlates with a higher or lower likelihood of disease-free or overall survival with respect to the group to which the patient was not assigned.

Therefore, the invention also provides a method of determining a prognosis for survival for a cancer patient that involves patient classification. The method is practiced by (a) measuring a level of TUCAN in a neoplastic cell-containing sample from the cancer patient, and (b) classifying the patient as belonging to either a first or second group of patients, wherein the first group of patients having low levels of TUCAN is classified as having an increased likelihood of survival compared to the second group of patients having high levels of TUCAN.

A high level of TUCAN, or overproduction of TUCAN, correlates with patients having an increased risk of tumor recurrence or spread. Thus, patients belonging to a first group having high levels of TUCAN are classified as having an increased risk of tumor recurrence or spread compared to a second group of patients having low levels TUCAN. Patients belonging to a first group having low levels of TUCAN are classified as having increased likelihood of survival compared to a second group of patients having high levels of TUCAN.

The method of determining a prognosis for survival for a cancer patient can be practiced using one or more additional biomarkers. A variety of biomarkers, including known cancer markers and the prognostic biomarkers disclosed herein, can be used in combination with TUCAN to determine a prognosis for survival for a cancer patient. In one embodiment, the method involves (a) determining a level of cIAP2 the neoplastic cell-containing sample from the cancer patient, and (b) classifying the patient as belonging to either a first or second group of patient, wherein the first group of patients having low levels of TUCAN and low levels of cIAP2 is classified as having increased likelihood of survival compared to the second group of patients having high levels of TUCAN and high levels of cIAP2.

In another embodiment, the method involves (a) determining a level of a biomarker selected from the group consisting of Apaf1, Smac and Bcl-2 in the neoplastic cell-containing sample from the cancer patient, and (b) classifying the patient as belonging to either a first or second group of patient, wherein the first group of patients having low levels of TUCAN and high levels of any of Apaf1, Smac or Bcl-2 is classified as having increased likelihood of survival compared to the second group of patients having high levels of TUCAN and low levels of any of Apaf1, Smac or Bcl-2.

After the levels of one or more biomarker in patient sample have been determined and compared to a reference level, the patient is then classified into a group having a certain likelihood of disease free or overall survival. Then the likelihood of disease-free or overall survival for the patient is assessed based on the likelihood of disease-free or overall survival for patients in that group.

For example, a neoplastic cell containing sample from a cancer patient can be determined to have high levels of Apaf1, Bcl-2 or Smac relative to a reference level. This patient would then be classified into a group of patients having high levels of Apaf1, Bcl-2 or Smac. Because it has been discovered that there is an increased likelihood of disease-free or overall survival for the group of patients expressing high levels of Apaf1, Bcl-2 or Smac in cancer cells (relative to those expressing low levels of Apaf1, Bcl-2 or Smac in cancer cells), the specific cancer patient would be considered to have an increased likelihood of disease free or overall survival.

Conversely, a neoplastic cell containing sample from a cancer patient can be determined to have high levels of cIAP2, β-catenin or TUCAN relative to a reference level. This patient would then be classified into a group of patients having high levels of cIAP2, β-catenin or TUCAN. Because it has been discovered that there is a decreased likelihood of disease-free or overall survival for the group of patients expressing high levels of cIAP2, β-catenin or TUCAN in cancer cells (relative to those expressing low levels of cIAP2, β-catenin or TUCAN in cancer cells), the specific cancer patient would be considered to have an decreased likelihood of disease free or overall survival.

The methods of the invention are applicable to determining the susceptibility of an individual for developing cancer. The methods are applicable to a variety of cancers, including gastrointestinal, lung, colon, prostate, breast, ovarian, skin, blood and kidney cancers. In particular, colon cancers develop from premalignant precursor lesions known as adenomatous colon polyps. Multiple epidemiological studies have demonstrated that once one member of a family has developed an adenomatous colon polyp, his or her siblings are at markedly elevated risk for developing both colon adenomas and colon cancers. Those skilled in the art understand that the method of the invention can be practiced as described herein for neoplastic conditions, including colon neoplastic conditions, such as adenomatous colon polyps, for example, by collecting an appropriate biopsy sample.

The methods of the invention for determining a prognosis for survival for a cancer patient are applicable to patients at any stage of tumor progression, and further can be used to determine a stage of tumor progress. A stage of a tumor refers to the degree of progression of a tumor. Various stages of tumor development are well known to those of skill in the art, as exemplified in Markman, "Basic Cancer Medicine," Saunders, (ed. Zorab, R.) (1997). For example, cancers can be staged into three general stages—localized, regional spread, and distant spread. Cancers also can be staged using the TNM system, which considers the extent of direct spread within affected and nearby tissues, the extent of spread to nearby lymph nodes, and the extent of spread to distant organs. Based on these features, spread of cancers can be summarized by assigning Roman numerals from 0 through IV. Those skilled in the art can select an appropriate staging system for a particular type of cancer.

In particular, colon cancer can be staged using the Dukes, Astler-Coller and AJCC/TNM systems, which describe the spread of the cancer in relation to the layers of the wall of the colon or rectum, organs next to the colon and rectum, and other organs farther away. Dukes stage A is equivalent to AJCC/TNM stage I and Astler-Coller stage A, Bl; Duke's stage B is equivalent to AJCC/TNM stage II and Astler-Coller stage B2, B3. Dukes stage C is equivalent to AJCC/TNM stage III and Astler-Coller stage C1, C2, C3. AJCC/TNM stages of colorectal cancer are as follow: Stage 0: the cancer has not grown beyond the inner layer (mucosa) of the colon or rectum. This stage is also known as carcinoma in situ or intramucosal carcinoma; Stage I: the cancer has grown through the mucosa into the submucosa, or can also have grown into the muscularis propria, but it has not spread outside the wall itself into nearby tissue such as lymph nodes; Stage II: the cancer has grown through the wall of the colon or rectum, into the outermost layers and may have invaded other nearby tissues, but has not yet spread to the nearby lymph nodes; Stage III: the cancer can be of any size, but has spread to 3 or fewer nearby lymph nodes, or has spread to 4 or more nodes but it has not spread to other parts of the body; Stage IV: the cancer has spread to distant organs such as the liver, lung, peritoneum or ovary.

Early stages of tumor development shall be understood to refer to stages in tumor development in which the tumor has detectably spread no further than the lymph nodes local to the organ of the primary tumor. Typically, early stages will be considered to be stages I and II.

The predictive value of the method of the invention will be particularly effective in the case of patients in the early stages of cancer. This is because the method of the invention is advantageously effective in determining the risk of metastasis in patients who demonstrate no measurable metastasis at the time of examination. One of ordinary skill in the art would appreciate that the prognostic indicators of survival for cancer patients suffering from stage I cancer may be different from those for cancer patients suffering from stage IV cancer. For example, prognosis for stage I cancer patients may be oriented toward the likelihood of continued growth and/or metastasis of the cancer, whereas prognosis for stage IV cancer patients may be oriented toward the likely effectiveness of therapeutic methods for treating the cancer.

A stage of cancer progression can be correlated with a level of one or more biomarkers, such as a level of TUCAN, Apaf1 or an IAP, such as cIAP2 or Smac. Therefore, a determination of a level of a biomarker in a sample from a cancer patient can be used to determine a stage of the tumor from which the sample was derived by comparing the sample with a reference level of the biomarker indicative of a particular stage of cancer.

The methods of the invention are applicable for use with a variety of different types of samples isolated or obtained from an individual having, or suspected of having a cancer or neoplastic condition. For example, samples applicable for use in one or more prognostic formats of the invention, include tissue and cell samples. A tissue or cell sample can be obtained, for example, from a fluid sample obtained from the patient, by biopsy or surgery. For example, in the case of solid tumors which have not metastasized, a tissue sample from the surgically removed tumor can be obtained and prepared for testing by conventional techniques. In addition, a sample can be removed from a patient, for example, using well-known biopsy procedures. For example, in the case of colon cancer, to obtain a sample of very small, raised polyps, a colonoscope can be fitted with a snare to remove a polyp without damage to the wall of the colon (polypectomy); or to obtain small, flatter polyps, a biopsy forceps can be attached to a colonoscope to collect a small sample of tissue.

As described below, and depending on the format of the method, the tissue can be used whole or subjected to various methods known in the art to disassociate the sample into smaller pieces, cell aggregates or individual cells. Additionally, when combined with amplification methods such as polymerase chain reaction (PCR), a single cell sample is sufficient for use in prognostic assays of the invention which employ hybridization detection methods. Similarly, when measuring biomarker polypeptide levels, amplification of the signal with enzymatic coupling or photometric enhancement can be employed using only a few or a small number of cells.

Whole tissue obtained from a biopsy or surgery is one example of a neoplastic cell-containing sample. Tumor tissue cell samples can be assayed employing any of the formats described below. For example, the tumor tissue sample can be mounted and hybridized in situ with biomarker nucleic acid probes. Similar histological formats employing protein detection methods and in situ activity assays also can be used to detect a biomarker polypeptide in whole tissue tumor cell samples. Protein detection methods include, for example, staining with a biomarker specific antibody, as described herein, in Example II. Such histological methods as well as others well known to those skilled in the art are applicable for use in the prognostic methods of the invention using whole tissue as the source of a neoplastic cell-containing sample. Methods for preparing and mounting the samples are similarly well known in the art.

Individual cells and cell aggregates from an individual having, or suspected of having a neoplastic condition or cancer is another example of a neoplastic cell-containing sample that can be analyzed for increased or decreased expression of biomarker RNA or polypeptide. The cells can be grown in culture and analyzed using procedures such as those described above. Whole cell samples expressing cell surface markers associated with biomarker expression can be rapidly tested using fluorescent or magnetic activated cell sorting (FACS or MACS) with labeled binding agents selective for the surface marker or using binding agents selective for specific cell populations, for example, and then determining a level of a biomarker within this population. A level of a biomarker can be determined using, for example, binding specifically reacting agents for a biomarker or by hybridization to a biomarker specific probe. Other methods for measuring the level of a biomarker in whole cell samples are known in the art and are similarly applicable in any of the prognostic formats described below.

The tissue or whole cell tumor cell sample obtained from an individual also can be analyzed for increased or decreased biomarker levels by lysing the cell and measuring the level of a biomarker in the lysate, a fractionated portion thereof or a purified component thereof using any of formats described herein. For example, if a hybridization format is used, biomarker RNA can be amplified directly from the lysate using PCR, or other amplification procedures well known in the art such as RT-PCR, 5' or 3' RACE to directly measure the level of a biomarker nucleic acid molecules. RNA also can be isolated and probed directly such as by solution hybridization or indirectly by hybridization to immobilized RNA. Similarly, when determining a level of a biomarker using polypeptide detection formats, lysates can be assayed directly, or they can be further fractionated to enrich for a biomarker. For example, an immunochemical method, such as immunoblot analysis (see Example III) can be performed using a neoplastic cell-containing sample. Numerous other methods applicable for use with whole tumor cell samples are well known to those skilled in the art and can accordingly be used in the methods of the invention.

The tumor tissue or cell sample can be obtained directly from the individual or, alternatively, it can be obtained from other sources for testing. Similarly, a cell sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the prognostic methods of the invention is that they do not require histological analysis of the sample. As such, the sample can be initially disaggregated, lysed, fractionated or purified and the active component stored for later diagnosis.

The prognostic methods of the invention are applicable for use with a variety of different types of samples other than tumor cell samples. For example, a biomarker polypeptide or fragment thereof that is released into the extracellular space, including circulatory fluids as well as other bodily fluids, can be used in prognostic methods to detect a secreted polypeptide or fragment related to a biomarker polypeptide. In such a case, the methods of the invention are applicable with fluid samples collected from an individual having, or suspected of having a neoplastic condition or cancer.

Fluid samples, which can be measured for biomarker levels, include, for example, blood, serum, lymph, urine and stool. Other bodily fluids are known to those skilled in the art and are similarly applicable for use as a sample in the prognostic methods of the invention. One advantage of analyzing fluid samples is that they are readily obtainable, in sufficient quantity, without invasive procedures as required by biopsy and surgery. Analysis of fluid samples such as blood, serum and urine will generally be in the prognostic formats described herein which measure biomarker polypeptide levels. As the biomarker related polypeptide is circulating in a soluble form, the methods will be similar to those which measure expression levels from cell lysates, fractionated portions thereof or purified components.

Neoplastic conditions and cancer can be diagnosed, predicted or prognosed by measuring a level of a biomarker in a neoplastic cell-containing sample, circulating fluid or other bodily fluid obtained from the individual. As described herein, levels of a biomarker can be measured by a variety methods known in the art.

One skilled in the art can readily determine an appropriate assay system given the teachings and guidance provided herein and choose a method based on measuring RNA or polypeptide. Considerations such as the sample type, availability and amount will also influence selection of a particular prognostic format. For example, if the sample is a tumor cell sample and there is only a small amount available, then prognostic formats which measure the amount of biomarker RNA by, for example, PCR amplification, or which measure biomarker polypeptide by, for example, FACS analysis can be appropriate choices for determining the level of a biomarker. Alternatively, if the sample is a blood sample and the user is analyzing numerous different samples simultaneous, such as in a clinical setting, then a multisample format, such as an Enzyme Linked Immunoabsorbant Assay (ELISA), which measures the amount of a biomarker polypeptide can be an appropriate choice for determining the level of a biomarker. Additionally, biomarker nucleic acid molecules released into bodily fluids from the neoplastic or pathological cells can also be analyzed by, for example, PCR or RT-PCR. Those skilled in the art will know, or can determine which format is amenable for a particular application and which methods or modifications known within the art are compatible with a particular type of format.

Nucleic acid probes can be produced recombinantly or chemically synthesized using methods well known in the art. Additionally, hybridization probes can be labeled with a variety of detectable labels including, for example, radioisotopes, fluorescent tags, reporter enzymes, biotin and other ligands. Such detectable labels can additionally be coupled with, for example, calorimetric or photometric indicator substrate for spectrophotometric detection. Methods for labeling and detecting such probes are well known in the art and can be found described in, for example, Sambrook et al., *Molecular Cloning: A Laboratory Manual,* 2nd ed., Cold Spring Harbor Press, Plainview, N.Y. (1989), and Ausubel et al., *Current Protocols in Molecular Biology* (Supplement 47), John Wiley & Sons, New York (1999).

Nucleic acid probes useful for detecting a biomarker in a sample can be hybridized under various stringency conditions readily determined by one skilled in the art. Depending on the particular assay, one skilled in the art can readily vary the stringency conditions to optimize detection of a particular biomarker in a particular sample type.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, at least 75% identity, at least 85% identity; or at least 90% identity. Moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual,* 2nd ed., Cold Spring Harbor Press, Plainview, N.Y. (1989); and Ausubel et al., supra, 1999). Nucleic acid molecules encoding polypeptides hybridize under moderately stringent or high stringency conditions to substantially the entire sequence, or substantial portions, for example, typically at least 15–30 nucleotides of the nucleic acid sequences of cIAP2, TUCAN, Apaf1, Bcl-2, Smac, β-catenin or another biomarker.

The invention relates to the discovery that high or low amounts of particular biomarkers, including cIAP2, TUCAN, Apaf1, Bcl-2, β-catenin and Smac are predictive of survival of patients having cancer. The over-expression or under-expression of these biomarkers can contribute to the genetic malfunction of cancer cells that leads to uncontrolled proliferation. Therefore, modulation of the level of a biomarker in a cancer cell to a level consistent with a normal cell can be used to return a cancer cell to a more normal proliferation state. In the case of over-expressed biomarker genes, such as cIAP2, TUCAN and β-catenin a variety of strategies can be employed to reduce gene expression. For example, inhibition of transcription or translation of cIAP2, TUCAN and β-catenin, or reduction in the amount of active cIAP2, TUCAN and β-catenin polypeptide, can be used to reduce the levels of these biomarkers to a level representative of a normal cell. In the case of under-expressed biomarker genes, such as Apaf1, Bcl-2 and Smac, a variety of strategies can be employed to increase gene expression. For example, introduction of Apaf1, Bcl-2 and Smac from an exogenous nucleic acid molecule, promotion of transcription or translation of Apaf1, Bcl-2 or Smac, or promotion in the amount of active Apaf1, Bcl-2 or Smac polypeptide, can be used to increase the levels of these biomarkers to a level representative of a normal cell.

Therefore, the invention additionally provides a method for treating or reducing the progression of a neoplastic condition such as cancer by reducing neoplastic cell proliferation. In one embodiment, the method involves administering a nucleic acid encoding Apaf1, Bcl-2 or Smac into a neoplastic cell and expressing the Apaf1, Bcl-2 or Smac polypeptide in an amount effective to reduce neoplastic cell proliferation. In another embodiment, the method of reducing neoplastic cell proliferation involves contacting a neoplastic cell with an effective amount of an agent that, under sufficient conditions, increases the amount of Apaf1, Bcl-2 or Smac in the cell.

Such an agent can increase the amount of a biomarker directly or indirectly, for example, by increasing the amount of a biomarker polypeptide in a cell, such as by stimulating increased mRNA expression. Apaf1, Bcl-2 or Smac mRNA expression can be increased, for example, by inducing or derepressing transcription of Apaf1, Bcl-2 or Smac genes and by regulating the expression of a cellular protein that acts as a transcription factor to regulate gene expression. An agent can act to increase the amount of Apaf1, Bcl-2 or Smac by increasing the stability of a Apaf1, Bcl-2 or Smac mRNA or polypeptide, for example, by decreasing a cellular degradation activity, such as a protease activity. Molecules that mediate the regulation of Apaf1, Bcl-2 or Smac expression, such as receptors and corresponding signal transduction molecules, can also be targets of agents that increase the amount of Apaf1, Bcl-2 or Smac in a cell. For example, a signal transduction pathway that stimulates the expression of Apaf1, Bcl-2 or Smac can be modulated to increase the level of Apaf1, Bcl-2 or Smac expression, for example, by increasing the rate of Apaf1, Bcl-2 or Smac synthesis or the length of time that gene expression remains active.

Conversely, a decrease in the amount of a biomarker in a cell can be affected by inducing changes in biomarker transcription, translation or protein stability opposite to those described above. As such, in a further embodiment, the method of reducing neoplastic cell proliferation involves contacting a neoplastic cell with an effective amount of an agent that, under sufficient conditions, decreases the amount of cIAP2, b-catenin or TUCAN in the cell.

The amount of a biomarker in a cell, such as cIAP2, TUCAN, β-catenin, Bcl-2, Apaf1 or Smac, can be modulated, for example, by increasing expression of the biomarker from an exogenous nucleic acid molecule, by introducing a biomarker polypeptide or functional analog thereof into a cell, by introducing inhibitor of a biomarker polypeptide into a cell, and by modulating the expression or activity of a gene or protein product that regulates the level of a biomarker in a cell. The amount of a biomarker in a cell also can be modulated using an antisense molecule to block transcription or translation of the biomarker mRNA. Specifically, cells can be transformed with sequences complementary to cIAP2, β-catenin or TUCAN nucleic acid molecules. Such methods are well known in the art, and sense or antisense oligonucleotides or larger fragments, can be designed from various locations along the coding or control regions of sequences encoding biomarkers. Thus, antisense molecules can be used to modulate biomarker activity, or to achieve regulation of gene function.

Ribozymes, enzymatic RNA molecules, can also be used to catalyze the specific cleavage of a biomarker mRNA, such as cIAP2, β-catenin or TUCAN. The mechanism of ribozyme action involves sequence-specific hybridization of the ribozyme molecule to complementary target biomarker RNA, followed by endonucleolytic cleavage. Specific ribozyme cleavage sites within any potential RNA target are identified by scanning the biomarker RNA for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes of the invention can be prepared by any method known in the art for the synthesis of nucleic acid molecules.

RNA interference (RNAi) can also be used to modulate the amount of a biomarker mRNA, such as cIAP2, β-catenin or TUCAN. RNAi is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., *Nature* 411:494–498 (2001); Bass, *Nature* 411:428–429 (2001); Zamore, *Nat. Struct. Biol.* 8:746–750 (2001)). dsRNAs of about 25–30 nucleotides have also been used successfully for RNAi (Karabinos et al., *Proc. Natl. Acad. Sci.* 98:7863–7868 (2001). dsRNA can be synthesized in vitro and introduced into a cell by methods known in the art.

A variety of methods are known in the art for introducing a nucleic acid molecule into a cell, including a cancer cell. Such methods include microinjection, electroporation, lipofection, calcium-phosphate mediated transfection, DEAE-Dextran-mediated transfection, polybrene- or polylysine-mediated transfection, and conjugation to an antibody, gramacidinS, artificial viral envelopes or other intracellular carriers such as TAT. For example, cells can be transformed by microinjection as described in Cibelli et al., *Nat. Biotech.* 16:642–646 (1998) or Lamb and Gearhart, *Cur. Opin. Gen. Dev.* 5:342–348 (1995); by lipofection as described in Choi (U.S. Pat. No. 6,069,010) or Lamb and Gearhart, *Cur. Opin. Gen. Dev.* 5:342–348 (1995); by electroporation as described in *Current Protocols in Molecular Biology*, John Wiley and Sons, pp 9.16.4–9.16.11 (2000) or Cibelli et al., *Nat. Biotech.* 16:642–646 (1998); or by fusion with yeast spheroplasts Lamb and Gearhart, *Cur. Opin. Gen. Dev.* 5:342–348 (1995).

A nucleic acid encoding a biomarker polypeptide, such as Apaf1, Bcl-2 or Smac, or other molecule useful for reducing proliferation of a cancer cell, can be delivered into a mammalian cell, either in vivo or in vitro using suitable vectors well-known in the art. Suitable vectors for delivering a nucleic acid encoding a biomarker polypeptide to a mammalian cell, include viral vectors and non-viral vectors such as plasmid vectors. Such vectors are useful for providing therapeutic amounts of a biomarker polypeptide, such as Apaf1, Bcl-2 or Smac, as well as for delivering antisense nucleic acid molecules and ribozymes.

Viral based systems provide the advantage of being able to introduce relatively high levels of the heterologous nucleic acid into a variety of cells. Suitable viral vectors for introducing a nucleic acid encoding a biomarker polypeptide, such as Bcl-2, Smac or Apaf1, into a mammalian cell are well known in the art. These viral vectors include, for example, Herpes simplex virus vectors (Geller et al., *Science,* 241:1667–1669 (1988)); vaccinia virus vectors (Piccini et al., *Meth. Enzymology,* 153:545–563 (1987)); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78–84)); Moloney murine leukemia virus vectors (Danos et al., *Proc. Natl. Acad. Sci. USA,* 85:6460–6464 (1988); Blaese et al., *Science,* 270:475–479 (1995); Onodera et al., *J. Virol.,* 72:1769–1774 (1998)); adenovirus vectors (Berkner, *Biotechniques,* 6:616–626 (1988); Cotten et al., *Proc. Natl. Acad. Sci. USA,* 89:6094–6098 (1992); Graham et al., *Meth. Mol. Biol.,* 7:109–127 (1991); Li et al., *Human Gene Therapy,* 4:403–409 (1993); Zabner et al., *Nature Genetics,* 6:75–83 (1994)); adeno-associated virus vectors (Goldman et al., *Human Gene Therapy,* 10:2261–2268 (1997); Greelish et al., *Nature Med.,* 5:439–443 (1999); Wang et al., *Proc. Natl. Acad. Sci. USA,* 96:3906–3910 (1999); Snyder et al., *Nature Med.,* 5:64–70 (1999); Herzog et al., *Nature Med.,* 5:56–63 (1999)); retrovirus vectors (Donahue et al., *Nature Med.,* 4:181–186 (1998); Shackleford et al., *Proc. Natl. Acad. Sci. USA,* 85:9655–9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., *Nature Genetics,* 17:314–317 (1997)). It is understood that both permanent and transient expression can be useful in a method of the invention.

An Apaf1, Bcl-2 or Smac polypeptide-encoding recombinant nucleic acid can be directed into a particular tissue or organ system, for example, by vector targeting or tissue-restricted gene expression. Therefore, a vector useful for therapeutic administration of a nucleic acid encoding an Apaf1, Bcl-2 or Smac polypeptide can contain a regulatory element that provides tissue specific expression of the polypeptide. For example, a nucleic acid sequence encoding a Apaf1, Bcl-2 or Smac polypeptide can be operatively linked to a cell specific promoter.

Any of a variety of inducible promoters or enhancers can also be included in a nucleic acid or vector of the invention to allow control of expression of a Apaf1, Bcl-2 or Smac polypeptide, or another molecule useful for modulating cell proliferation, such as an antisense nucleic acid molecule or ribozyme, by added stimuli or molecules. Such inducible systems, include, for example, tetracycline inducible system (Gossen & Bizard, *Proc. Natl. Acad. Sci. USA,* 89:5547–5551 (1992); Gossen et al., Science, 268:1766–1769 (1995); Clontech, Palo Alto, Calif.); metalothionein promoter induced by heavy metals; insect steroid hormone responsive to ecdysone or related steroids such as muristerone (No et al., *Proc. Natl. Acad. Sci. USA,* 93:3346–3351 (1996); Yao et al., *Nature,* 366:476–479 (1993); Invitrogen, Carlsbad, Calif.); mouse mammary tumor virus (MMTV) induced by steroids such as glucocorticoid and estrogen (Lee et al., *Nature,* 294:228–232 (1981); and heat shock promoters inducible by temperature changes.

An inducible system particularly useful for therapeutic administration utilizes an inducible promoter that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., *Proc. Natl. Acad. Sci. USA,* 96:355–360 (1999). The GENE SWITCH inducible expression system (U.S. Pat. Nos. 5,935,934 and 5,874,534) is an example of such a system. Other inducible systems use the drug rapamycin to induce reconstitution of a transcriptional activator containing rapamycin binding domains of FKBP12 and FRAP in an adeno-associated virus vector (Ye et al., *Science,* 283:88–91 (1999)), use tetracycline to control transcription (Baron *Nucleic Acids Res.* 25:2723–2729 (1997)) and use synthetic dimerizers to regulate gene expression (Pollock et al., *Methods Enzymol.* 306:263–281 (1999)). Such a regulatable inducible system is advantageous because the level of expression of the therapeutic product can be controlled by the amount of drug administered to the individual or, if desired, expression of the therapeutic product can be terminated by stopping administration of the drug.

It is understood that modifications which do not substantially affect the activity of the various embodiments of this invention are also included within the definition of the invention provided herein. Accordingly, the following examples are intended to illustrate but not limit the present invention.

EXAMPLE I

Generation of Antibodies for Immunodetection of IAPs and Apaf1

This example shows preparation and characterization of antibodies useful for detecting IAPs and Apaf1.

Figure 3:
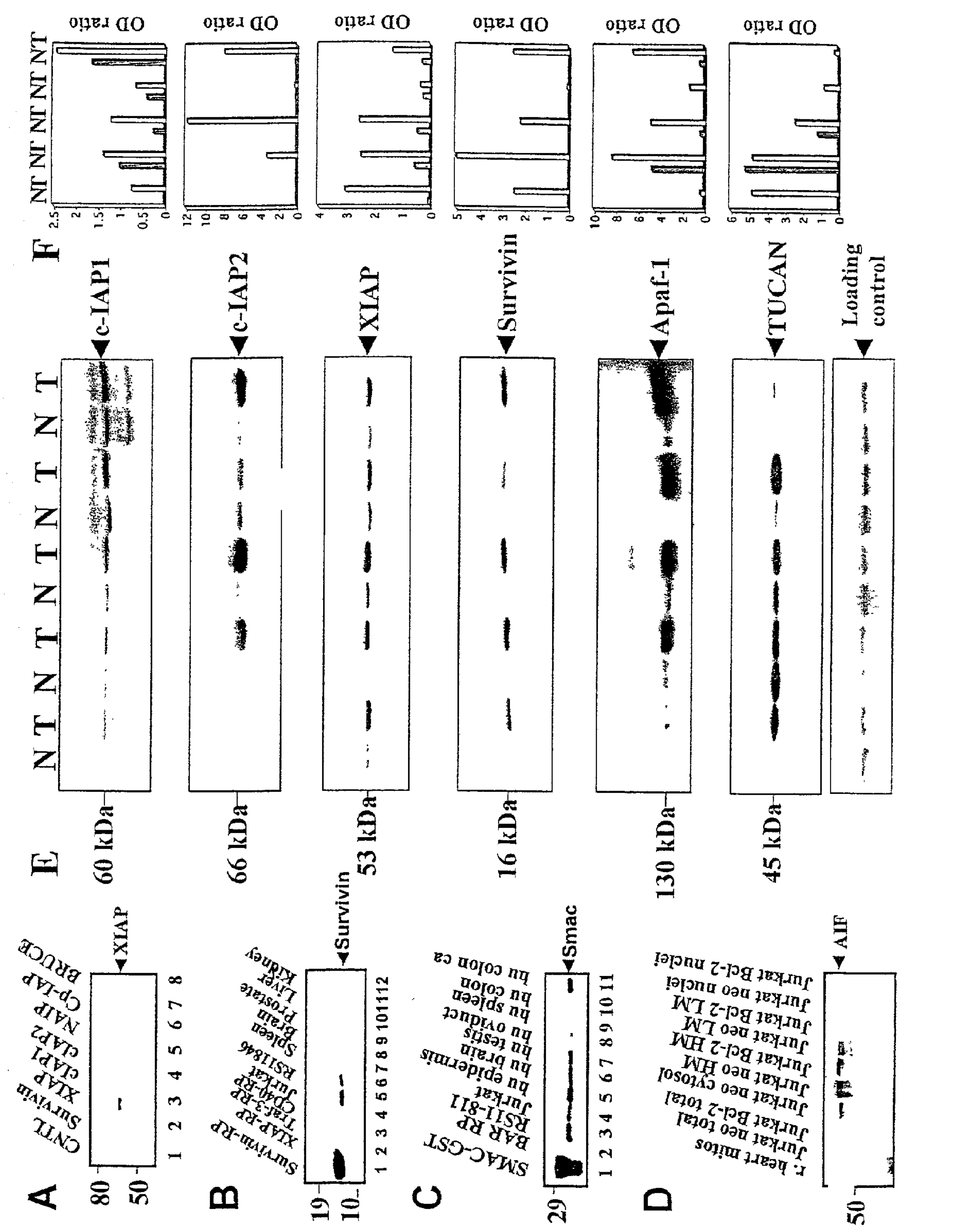
FIGS. 3A–3F show the specificity of antibodies and expression of IAPs, Apaf1 and TUCAN protein in colon carcinoma by immunoblotting.

Antisera were raised against recombinant proteins and synthetic peptides for immunodetection of Survivin, XIAP, Apaf1, AIF and Smac. Prior to employing these antibodies for analysis of cancers, the specificity of these antibodies for their intended protein targets was confirmed by SDS-PAGE/immunoblot analysis. Examples of data are provided in FIG. 3. FIG. 3A shows in vitro translated Survivin, XIAP, cIAP1, cIAP2, NAIP, BRUCE, and baculovirus Cp-IAP proteins were subjected to SDS-PAGE/immunoblot analysis, using polyclonal XIAP antiserum (AR-27A). Incubation with XIAP antiserum detected only XIAP in vitro translated protein. Detergent lysates were prepared from various normal human tissues, normalized for total protein content (50 ug), and subjected to SDS-PAGE/immunoblot assay using antisera specific for Survivin (B), Apaf1 (C), SMAC (D) or AIF (E); molecular weight markers are indicated in kilo-Daltons (F). In addition, lysates from 5 matched pairs of colon carcinoma (T) and normal colonic mucosa (N) specimens were analyzed for total protein content (100 mg per lane) and subjected to SDS-PAGE/immunoblot analysis, using the antisera specific for c-IAP1, c-IAP2, XIAP, Survivin, Apaf-1, and TUCAN (G). Antibody detection was accomplished by an ECL method. Immunoblot data were quantified by scanning densitometry using Pro-Image software system.

The anti-XIAP antiserum reacted specifically with the expected ~57 kDa XIAP protein, but not with other IAP-family members including Survivin, cIAP1, cIAP2, NAIP, BRUCE, and baculovirus Cp-IAP—which were all produced by in vitro transcription and translation from cDNAs (FIG. 3A). Similarly, monospecificity of the anti-Survivin antiserum was demonstrated by SDS-PAGE/immunoblot analysis of recombinant IAP-family proteins and lysates from normal tissues which lack Survivin mRNA and protein versus tumor cell lines which express Survivin protein (FIG. 3B). The anti-Smac antiserum displayed specific reactivity against GST-Smac recombinant protein (FIG. 3C). The antibody detected abundant amounts of Smac protein in RS11 and Jurkat cells, and several human tissues, such as epidermis, brain and testis. Barely detectable Smac levels in normal colon contrasted with relatively high amount of this protein in a colon cancer lysate.

Polyclonal antisera for Survivin, Apaf1, XIAP and Smac were generated in rabbits using recombinant protein immunogens. Survivin (full-length protein) and Apaf1 (residues 264–282) were produced as GST-fusion proteins from pGEX vectors using Escherichia coli BL21 (DE3) as the host strain. The protein purification method has been described previously. An additional anti-Apaf-1 serum was generated in rabbits using a synthetic peptide as the immunogen. A peptide (NH2-CGPKYVVPVESSLGKEKGLE-amide (SEQ ID NO:15)) corresponding to residues 264–282 of human (hu) Apaf-1, was synthesized with an N-terminal cysteine appended to permit conjugation to maleimide-activated carrier proteins KLH and OVA (Pierce, Inc.). This peptide conjugate was used to generate a polyclonal antiserum (AR-23) in rabbits. Affinity-purified His 6-tagged—XIAP BIR2 recombinant protein was produced using published methods and was used as an immunogen to produce XIAP-specific antiserum (AR-27A). An anti-AIF serum was produced in rabbits using a synthetic peptide corresponding to residues 151–170 of human AIF. New Zealand white female rabbits were injected subcutaneously with a mixture of 0.25 ml KLH-peptide (1 mg/ml), 0.25 ml OVA-peptide (1 mg/ml), or recombinant protein (0.1–0.25 μg protein per immunization) and 0.5 ml Freund's complete adjuvant (dose divided over 10 injections sites) and then boosted 3 times at weekly intervals, followed by another 3–20 boostings at monthly intervals with 0.25 mg each of KLH-peptide, OVA-peptide, or recombinant protein immunogens in Freund's incomplete adjuvant, collecting blood at 1–3 weeks after each boosting to obtain immune serum. The generation of Bcl-2, Bcl-XL, Bax, and TUCAN-specific antisera has been described. Anti-c-IAP1 and c-IAP2 antibodies were obtained from Santa Cruz Biotechnology Inc., CA and R&D Systems, Inc., β-Catenin antiserum from BD Transduction Laboratories, and p53 clone DO-7, MIB-1, and BAG1 clone KS-6C8 from DAKO.

EXAMPLE II

Immunohistochemical Analysis of IAPs and Other Biomarkers in Normal Colonic Mucosa and Colon Cancer This example shows immunohistochemical analysis of IAPs and other biomarkers in a tissue microarray representing tissue samples obtained from 102 individuals.

A tissue microarray was constructed using primary tumor specimens derived from a relatively homogenous cohort of 102 patients presenting with stage II disease (Dukes' B stage) to a single institution, and who were treated by surgical resection with curative intent. Colon carcinoma specimens were obtained from Department of Pathology, Yonsei University, College of Medicine, Seoul, Korea. Samples were taken from primary tumors derived from patients who presented between 1986 and 1996 with Dukes' B stage [stage II disease, as defined by American Joint Committee on Cancer and Union Internationale Contre le Cancer (AJCC/UICC) criteria]. Patients with Dukes' stage B2 (T3NOMO) constituted 91% of the cohort, whereas 9% suffered from a Dukes'B3 (T4NOMO) cancer. All patients were treated by surgical resection of the involved segment of colon. No postoperative adjuvant chemotherapy was performed initially in all cases. However, chemotherapy was administered for some patients after relapse. Clinical data represent a median follow up of 60 months.

To construct colon cancer microarrays, 2–5 cylinders of 1 mm diameter tissue were taken from representative areas of archival paraffin blocks containing 8% formalin-fixed tumor and arrayed into a new recipient paraffin block with a custom-built precision instrument (Beecher Instruments, Silver Spring, Md.). Serial sections (4 μm) were applied to 3-aminopropyl-triethoxysilane (APES)-coated slides (Sigma).

Microarrays were immunostained using antisera specific for the IAP family members Survivin, XIAP, cIAP1, and cIAP2 (FIG. 1A), and other markers such as Apaf1, Smac, AIF, Bcl-2, Bcl-XL, Bax, BAG1, β-Catenin, MIB-1 and p53. Dewaxed tissue sections were immunostained using a diaminobenzidine (DAB)-based detection method as described in detail, employing the Envision-Plus-Horse Radish Peroxidase (HRP) system (DAKO) using an automated immunostainer (Dako Universal Staining System). Antisera specific for Survivin, XIAP, Apaf1, TUCAN, AIF, Smac, Bax, and Bid were applied at 1:3000 to 10000 (v/v), for Bcl-2 and Bcl-XL at 1:2000 (v/v). The dilutions of c-IAP1, c-IAP2 and β-Catenin antibodies were 1:600 (v/v), BAG1 and MIB-1 1:100, and p53 1:50. For all tissues examined, the immunostaining procedure was performed in parallel using preimmune serum to verify specificity of the results. Initial confirmations of antibody specificity also included experiments in which antiserum was preabsorbed with 5–10 μg/ml of either synthetic peptide immunogen or recombinant protein immunogen. The scoring of tumor immunostaining was based on the percentage of immunopositive cells (0–100) multiplied by staining intensity score (0/1/2/3), yielding scores of 0–300. All immunostaining results were quantified according the approximate percentage of immunopositive cells (0–100%) and immunointensity on a 0–3 scale, and then an immunoscore was calculated from the product of the percentage immunopositivity and immunointensity (0–300).

Tissue sections were immunostained using various antisera, as described above, followed by detection using a HRPase-based method with diaminobenzidine calorimetric substrate (brown). Nuclei were counterstained with hematoxylin (blue). Representative data are shown in FIG. 1. FIG. 1A shows a colon cancer microarray slide stained for cIAP2 (×5 magnification). Examples of normal colonic epithelium immunostaining are presented for cIAP1 (B; ×100), Survivin (D; ×150), Smac (E; ×150), AIF (G; ×150), and Tucan (K; ×20). Immunostaining results in regions of invasive cancer are shown for Smac (F; ×400), AIF (H; ×250), Apaf1 (I, J; ×200), TUCAN (L×20; M×400), and Bcl-2 (N; ×150). Examples of malignant and the adjacent normal colonic epithelium are presented for cIAP2 (C; ×40), p53 (O; ×150) and MIB-1 (P; ×400).

Several of the 102 tumor specimens on the array (~65%) contained adjacent normal colonic mucosa (59–70), depending on the particular slide), permitting side-by-side comparisons of immunostaining results for normal versus malignant epithelium. In addition, 4 specimens of normal colon derived from individuals who were not diagnosed with colon cancer were stained separately. Immunoreactivity for the cIAP1 and cIAP2 proteins was detected in 62/62 (100%) and 34/65 (52%) of normal colonic mucosa specimens examined, respectively. The intensity of cIAP1 staining in non-malignant epithelium progressively increased from the base of the crypts to the luminal surface (FIG. 1B). In contrast, low cIAP2 immunoreactivity was more evenly distributed along the crypt-villus axis, though a slight increase in immunointensity in the upper regions of the villi was sometimes evident. XIAP was also expressed in non-malignant colonic epithelium (63/63 [100%]) and was distributed in a gradient similar to cIAP1, with XIAP immunoreactivity highest in the upper portions of the villi. Low intensity Survivin immunostaining was present in 60/62 (97%) of specimens containing normal colonic epithelium. Survivin immunoreactivity was predominantly nuclear in the crypt epithelial cells, and became progressively stronger in intensity and predominantly cytoplasmic towards the luminal surface along the crypt-villus axis (FIG. 1D). Immunohistochemical analysis of Apaf1 in normal colonic mucosa revealed the presence of immunoreactivity in 58/60 (97%) of specimens. Apaf1 immunoreactivity was present predominantly in perinuclear and cytosolic locations in normal colonic epithelial cells, with the intensity slightly increasing as the cells migrated from the crypt bases to the upper regions of the villi. Along with Apaf1, the intracellular concentration of Smac protein increased towards the luminal surface in 58/62 (94%) of normal colonic mucosa specimens (FIG. 1E). A relatively high mostly granular cytosolic expression of AIF was uniformly distributed along the colonic crypts in 100% of specimens (60/60) (FIG. 1G). The specificity of these immunostaining results was confirmed by control stainings performed using either preimmune serum or immune antisera which had been preabsorbed with the relevant immunogens.

Figure 2A:
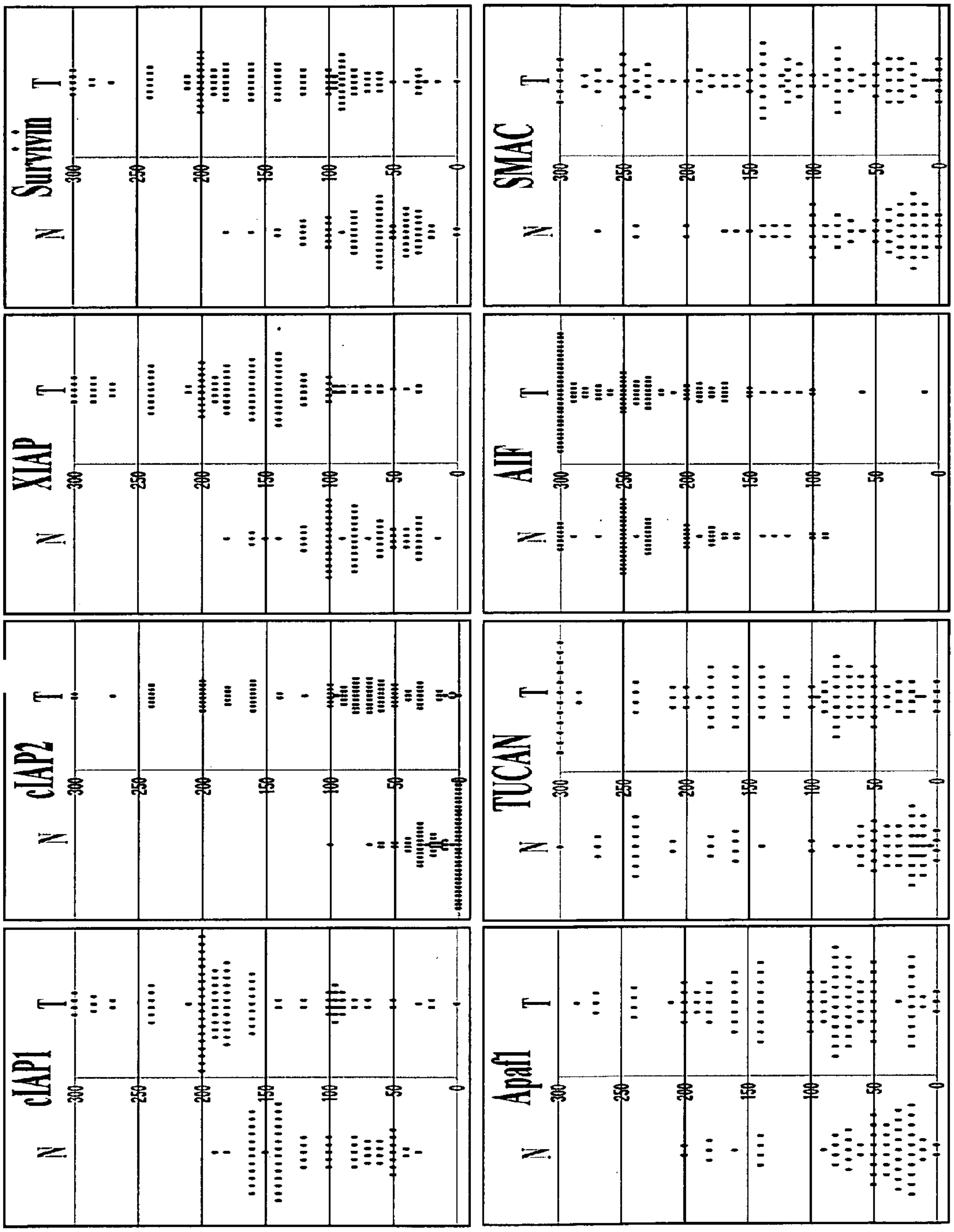
FIGS. 2A and 2B show comparisons of immunoscores for normal and malignant colon tissues.
Figure 2B:
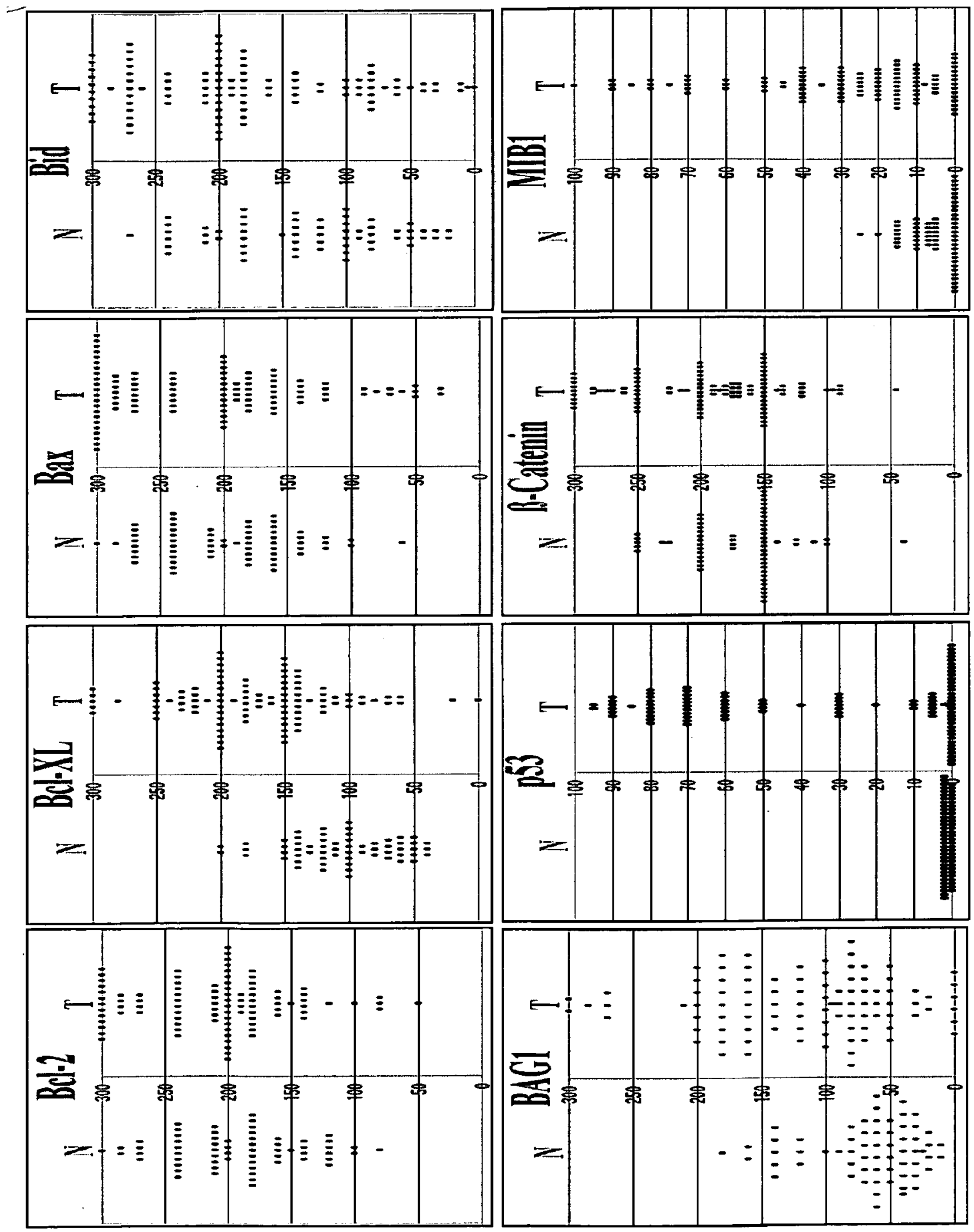

Immunohistochemical analysis of tumor tissues on the microarray revealed several examples of cancer-specific alterations in the expression of these apoptosis-regulatory proteins. FIG. 1 shows some examples of the immunostaining results for tumor specimens. The mean intensity of immunostaining was significantly higher in the invasive cancer compared to normal colonic epithelium for all investigated proteins (FIG. 1C, E–F, K–M, O, P) with the exception of Bcl-2, Bax, and AIF (FIG. 1G, H). Moreover, while immunostaining results varied widely among specimens examined, the immunoscores for a portion of the cancer specimens clustered into groups displaying clear elevations in immunoreactivity when compared to normal specimens (FIG. 2). For example, while all normal colonic specimens had cIAP1 immunoscores of $<200$, 35 of 94 (37%) invasive cancer specimens had immunoscores of$=200$ ($p<0.0001$), thus suggesting that a subgroup of colon cancers develops pathological elevations in the levels of this anti-apoptotic protein. Similarly, cIAP2 immunoscores were $<100$ for normal colonic epithelium, in contrast to invasive cancers where 25 of 94 (27%) had immunoscores of $>100$ ($p<0.0001$). Likewise, all normal colonic epithelium samples possessed immunoscores of $<190$ for XIAP, while 34 of 97 invasive cancers (35%) had XIAP immunoscores of $>190$ ($p<0.0001$). Survivin immunoscores for non-malignant epithelium were $<190$, compared to invasive cancers where scores $>190$ were found for 33 of 100 (33%) of specimens ($p<0.0001$). For Apaf1, two clusters of immunoscores emerged for both normal and malignant epithelium. Most normal colonic specimens (50/60; 83%) had immunoscores $<100$. In tumors, a group of specimens with similarly low immunoscores ($<100$) was observed (64/102; 63%) (FIG. 1J) but an additional group of cancers (38/102; 37%) was identified in which immunoscores clustered above 100, ranging from 140–280 (FIG. 1I). These results show that for all biomarkers examined, evidence of tumor-associated upregulation of expression was observed in a portion of the cancer specimens evaluated.

Elevated levels of cIAP2, Survivin, and β-Catenin correlated with high Ki-67 labeling index ($p=0.006$, $p=0.005$, and $p=<0.0001$, respectively). Statistical analysis revealed a significant correlation between the levels of Survivin and those of XIAP and cIAP1 ($p=0.01$), or cIAP2 ($p=0.008$). Elevated levels of survivin were associated with high expression of Bcl-2. A positive correlation between the expression of cIAP2 and TUCAN ($p=0.003$) agrees with an observed positive impact that a combination of low levels of these proteins has on survival in our cohort of colon carcinoma patients. However, an inverse correlation between TUCAN and Bcl-2 or AIF, did not reach a statistical significance. No significant association between cIAP2 and Apaf1 or Bcl-2 was found. Bcl-2, which has implications of a good prognostic marker in our cohort, correlates significantly with some pro-apoptotic proteins, such as Apaf1 ($p<0.0001$), AIF ($p=0.002$) and Smac ($p=0.008$), but also with an anti-apoptotic BAG1 protein which was found to predict long-term survival in early-stage breast cancer (#7874). An increased nuclear concentration of p53, which in 80% is related to p53 point missense mutation correlated with increased expression of Bcl-XL ($p<0.0001$).

EXAMPLE III

Immunoblot Analysis of IAPs and Apaf1 in Colon Carcinoma

This example shows immunoblot analysis of IAPs, Apaf1 and other apoptosis-regulators in five frozen colon cancer specimens.

To corroborate the immunohistochemistry data, five frozen colon cancer specimens were identified that had sufficient amounts of both adjacent normal (N) and tumor (T) tissue for immunoblot analysis using antibodies specific for IAPs, Apaf1, and other proteins. Detergent-lysates of these tissues specimens were prepared and normalized for total protein content prior SDS-PAGE/immunoblot analysis (FIG. 3E). Densitometry analysis was also performed to quantify band intensities, and the results from the loading control blot were used to normalize all data (FIG. 3F).

Colon cancer specimens (n=10) with high ratios of cancer cells relative to stroma (>70%) were selected for immunoblotting analysis. The protein lysates were prepared without additional microdissection or fractionation. The tumor lysates and the samples of the normal mucosa from the same patients were prepared using modified RIPA buffer (50 mM Tris [pH 7.4], 150 mM NaCl, 0.25% Na-deoxycholate, 1% NP40, 1 mM EDTA, 1 mM Na3VO4, 1 mM NaF, 1 mM PMSF) containing complete protease inhibitor cocktail (SIGMA), Pan-Caspase inhibitor z-Asp-2.6-dichlorobenzoyloxy-methylketone and ZVAD-fmk, normalized for total protein content (100 ug) and resolved by SDS-PAGE (12% and 15% gels). Protein quantification was performed using the Bio-Rad Protein Assay Kit (Bio-Rad). Proteins were transferred (overnight 150 mA, 4° C.) to PVDF membranes (Amersham Pharmacia). After blocking with 5% skim milk in TBST (50 mM Tris [pH 7.6], 150 mM NaCl, 0.05% Tween 20) at room temperature for 2 hours, blots were incubated overnight with antisera specific for particular IAP family members, Apaf1, and TUCAN, using 1:1,000–1:10,000 (v/v) dilutions at 4° C. After incubation with HRPase-conjugated secondary goat anti-rabbit (either Bio-Rad or Santa Cruz) antibody at room temperature for 1 hr, immunodetection was accomplished by an enhanced chemoluminescence (ECL) method (Amersham), with exposure to x-ray film (Kodak/XAR). Densitometry was performed to quantify the intensity of bands, using Image-pro Plus software.

Higher levels of cIAP2, XIAP, Survivin, and Apaf1 were detected in every specimen evaluated, compared to case-matched normal tissue. Levels of cIAP1 protein, as well as the anti-apoptotic protein TUCAN, were elevated in some tumor specimens compared to normal, but not others. A nonspecific band obtained during preblocking procedure with a secondary ECL antibody (Biorad), served as a loading control.

The immunoblotting results confirmed the immunohistochemistry observations described in Example II (FIG. 1E, F). Higher levels of cIAP2, XIAP, Survivin, and Apaf1 were detected in every specimen evaluated as compared to case-matched normal tissue. Levels of cIAP1 and TUCAN were elevated in some tumor specimens compared to normal, but not others.

EXAMPLE IV

Correlation of Protein Expression with Clinical Outcome

To analyze the relation of biomarkers with patient survival, the comparisons of the immunoscores obtained for normal colonic epithelium and colon cancers shown in FIG. 3 were used to set logical cut-offs for dichotomization of data.

Clinical data were available for all patient specimens included on the tissue microarray with respect to relapse and overall survival, with a median follow-up of 5 years. Patients were categorized as: (i) Alive without disease (A); (ii) Alive with recurrent disease (R); or (iii) Dead (D). As shown in Table 2, no significant differences in the immunoscores for cIAP1, XIAP, or Survivin were observed when comparing the A, R, and D groups of patients. cIAP2 immunostaining was significantly higher in colon cancer patients who had either died of disease (D) or who had relapsed after surgery (R) ($p<0.0001$). In contrast, immunoscores for Apaf1 were significantly lower in the groups of patients who had relapsed (R) or died (D), compared to patients who were alive without disease ($p<0.0001$) (Table 2). An unpaired t-test method was used for comparisons of XIAP, Survivin, cIAP1, cIAP2, and Apaf1 immunoscores in the A, R, and D groups of patients. P-values refer to a comparison of group A with the combined groups R and D.

TABLE 2

Summary of immunostaining results for colon cancer patients

| | XIAP | | Survivin | | cIAP1 | | cIAP2 | | Apaf1 | |
|---|---|---|---|---|---|---|---|---|---|---|
| Patient Status | Mean ± SE | Median | Mean ± SE | Median | Mean ± SE | Median | Mean ± SE | Median | Mean ± SE | Median |
| A | 168 ± 9 | 160 | 152 ± 10 | 160 | 166 ± 9 | 190 | 81 ± 9 | 70 | 132 ± 8 | 140 |
| R | 176 ± 22 | 170 | 125 ± 25 | 95 | 169 ± 23 | 180 | 162 ± 22 | 160 | 46 ± 20 | 50 |

TABLE 2-continued

Summary of immunostaining results for colon cancer patients

| Patient Status | XIAP Mean ± SE | Median | Survivin Mean ± SE | Median | cIAP1 Mean ± SE | Median | cIAP2 Mean ± SE | Median | Apaf1 Mean ± SE | Median |
|---|---|---|---|---|---|---|---|---|---|---|
| D | 177 ± 13 | 180 | 135 ± 13 | 120 | 174 ± 13 | 180 | 146 ± 13 | 130 | 77 ± 12 | 70 |
| p-values A vs R + D | 0.5 | | 0.2 | | 0.7 | | <.0001 | | <.0001 | |

To analyze the relation of biomarkers to patient survival by another method, immunostaining data for these proteins were dichotomized into high-versus low-expression groups. For this purpose, the comparisons of the immunoscores obtained for normal colonic epithelium and colon cancers shown in FIG. 2 were used to set logical cut-offs for dichotomization of data. Immunoscores for normal and malignant colon epithelium were depicted in a graphic form in FIG. 2. Based on comparisons with normal colonic epithelium, cutoffs for dichotomizing immunostaining data were selected. The range of immunoscore for 95% of normal specimens defined a group of tumors with low immunoscore for cIAP1, cIAP2, XIAP, Survivin, Bcl-XL, and BAG1. Bimodal distribution of proteins helped to identify cut-offs for Bax, Apaf1 and TUCAN. The application of median immunoscores as cut-offs for Bcl-2, Bid, AIF, Smac, and β-catenin, increased accuracy in the subcategorisation of tumors into low and high expressors. The histograms for p53 and MIB-1 present the immunopercentage, classifying cases >0% as high p53 expressors and=20% as those expressing high levels of MIB.

Based on this method, high levels of Apaf1, TUCAN, Survivin, XIAP, cIAP1, and cIAP2 were found in 38%, 49%, 54%, 74%, 61% and 35% tumor specimens, respectively. In univariate analysis, significant correlations were observed in this cohort between longer disease-free survival (DFS) and low expression of cIAP2 (p=0.0002), TUCAN (p=0.0004), β-Catenin (p=0.04), mutant p53 protein (p=0.03), or high levels of Apaf1 (p=0.00008), Bcl-2 (p=0.005), and SMAC (p=0.03) (FIG. 4a). Thus, 78% ($^{39}/_{50}$) of patients whose tumors contained low levels of TUCAN remained alive and disease-free during the time covered by this study, compared to only 44% ($^{21}/_{48}$) of those with high expression of this protein. Similarly, 74% ($^{45}/_{61}$) of low cIAP2 expressors enjoyed colon cancer-free life at the time of last survey compared to only 36% ($^{12}/_{33}$) of those with high cIAP2 levels. In contrast, high levels of Apaf1 were associated with longer survival in this cohort of colon cancer patients, with $^{33}/_{38}$ (87%) of patients remaining disease-free compared to only $^{28}/_{62}$ (45%) of those with low Apaf1 expression.

The most significant improvement of overall survival was noticed in a group of patients whose colon carcinoma specimens contained low levels of TUCAN (p<0.0001) (FIG. 4b). Among 50 patients expressing low TUCAN, only 4% ($^{2}/_{50}$) died, as opposed to 54% ($^{26}/_{48}$) of those presenting high levels of this protein. Significant correlations were also observed between longer overall survival and low cIAP2 (p=0.01) or low mutant p53 protein (p=0.03). Low Bcl-2 levels were associated with poor overall survival. Of 18 patients with low expression of this protein, 11 (61%) died of colon cancer, compared with 24% of patients who died in the high-Bcl-2 group ($^{18}/_{76}$). Similarly, patients whose tumors contained low Apaf1 staining had worse overall survival compared with those who overexpressed Bcl-2 (FIG. 1N).

Elevated levels of Bcl-2 conferred a significant advantage for both overall (p=0.0008) and disease-free survival (p=0.005). Of 76 patients whose tumors revealed high Bcl-2, 58 (76%) remained alive and 50 (66%) relapse-free, compared to 39% and 33% of those with low Bcl-2 levels. Independent of its anti-apoptotic function, Bcl-2 can delay entry into the cell cycle and promote exit of cells from the cycle. Thus, a positive effect of Bcl-2 on clinical outcome may be linked to its cell cycle-inhibitory role.

Figure 4:
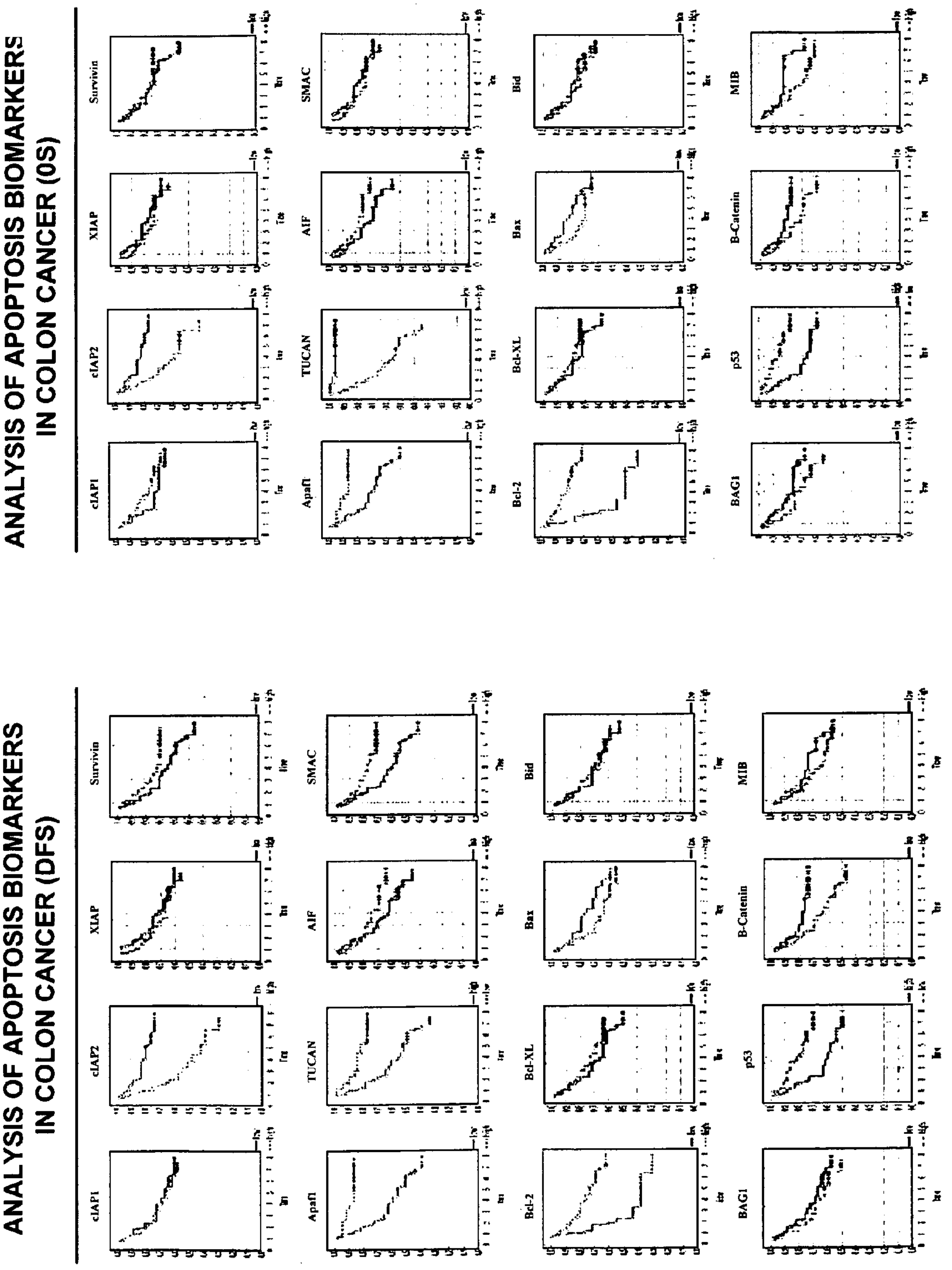
FIG. 4 shows correlations of biomarker immunostaining data with disease-free (left panels, labeled "DFS") and overall survival (right panels, labeled "OS") for colon carcinoma patients.

FIG. 4 shows correlations of biomarkers immunostaining data with disease-free (A) survival and overall survival (B) for colon carcinoma patients. All biomarkers data and outcome measures were entered into a database using STATISTICA software system (StatSoft). The log rank test was used to for correlation of immunoscore data with the patient survival. The Kaplan-Meier curves illustrate correlations of the investigated biomarkers with survival for this cohort of patients.

In summary, at a median follow-up of 5 years, 60% of patients with high cIAP2 levels relapsed and 46% died of colon cancer, whereas in a low-cIAP2 group there were 20% relapses and 18% colon cancer-related deaths. At the same time point, 49% of patients with high expression of TUCAN had relapse or died of colon cancer, and only 19% had recurrence and 4% died of disease in a group of patients whose tumors expressed low levels of this protein. In contrast, 43% of patients with low Apaf1 relapsed and 35% died of colon cancer, while only 14% had a cancer recurrence or died in a high-Apaf1 cohort. Thus, these findings indicate that higher levels of the anti-apoptotic protein cIAP2 and lower levels of the pro-apoptotic protein Apaf1 are associated with adverse outcome in patients with early-stage colon cancer. No significant differences were noted in the age, or gender of the patients in the high-versus low-expression groups for cIAP2, Apaf1, or TUCAN.

EXAMPLE V

Combined Analysis of cIAP2 and Apaf1 Expression Data

This example shows combined analysis of cIAP2 and Apaf1 expression data.

Since certain proteins had significant prognostic value, it was determined whether combining two biomarkers could identify a subgroup of patients with distinct survival characteristics. Patients with two favorable variables (low cIAP2 and high Apaf1) were compared with all other patients in this cohort.

Figure 5:
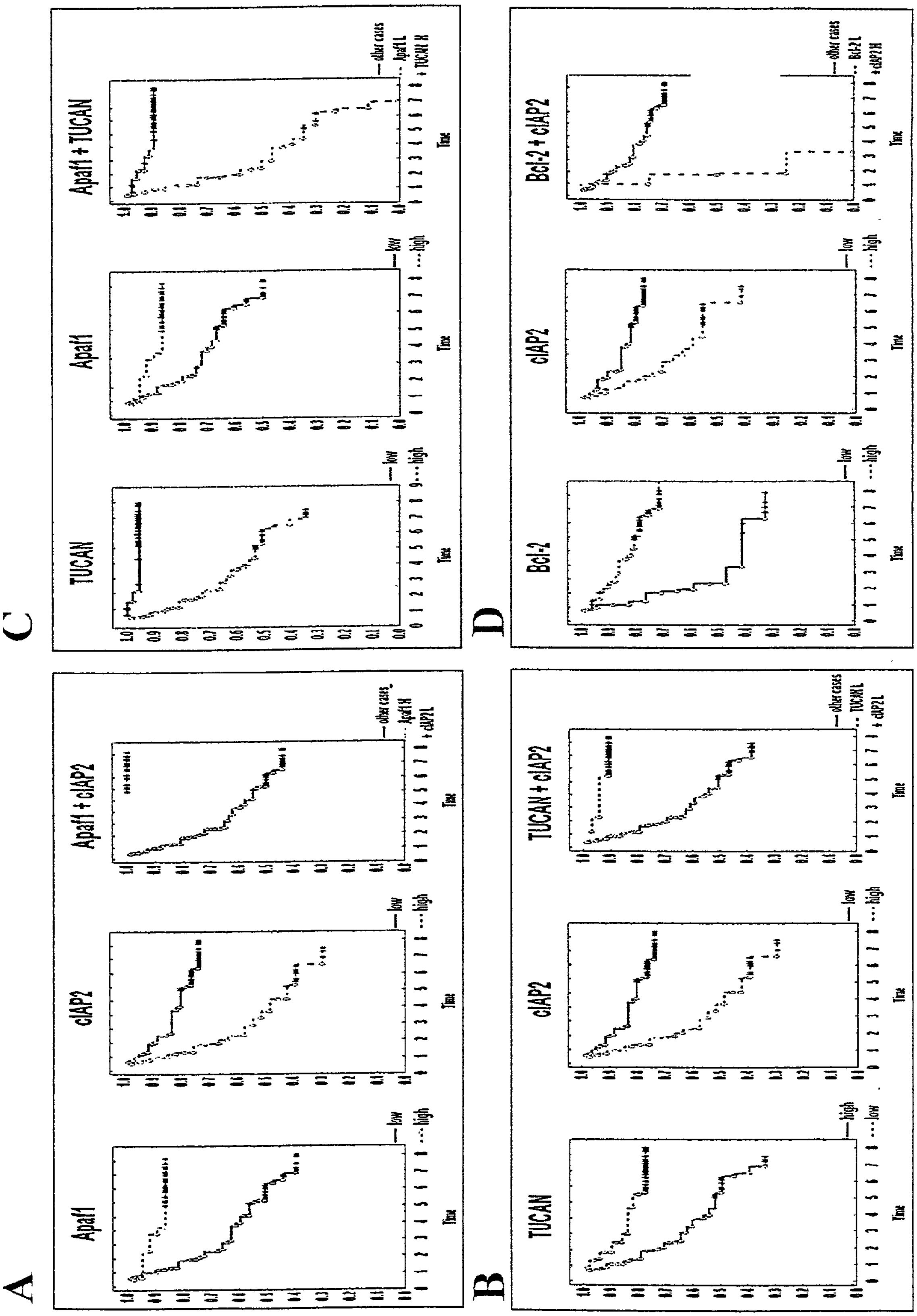
FIGS. 5A–5D show correlations of biomarkers and their combinations with disease-free (FIGS. 5A and 5B) and overall (FIGS. 5C and 5D) survival for colon carcinoma patients.

FIG. 5 shows correlations of biomarkers and their combinations with disease-free (A, B) survival and overall survival (C, D) for colon carcinoma patients. Using the Kaplan-Meier curves, panels A and B illustrate a combination of biomarkers [low cIAP2 and high Apaf1 (A); low cIAP2 and low TUCAN (B)] with positive impact on disease-free survival. The two combinations of markers with an adverse effect on survival are presented in panel C (low Apaf1 and high TUCAN), and panel D (low Bcl-2 and high cIAP2).

Of the 94 patient samples successfully analyzed for cIAP2 and Apaf1, 25 (27%) had both a low cIAP2 and a high Apaf1 immunoscore. All (100%) of these patients with the combination of low cIAP2 and high Apaf1 were alive and disease-free at 5 years after diagnosis, compared to 52% disease-free or 64% alive of others (p=0.00007 for OS; p<0.0001 for DFS) (FIG. 5A; DFS). At the same time point, among patients with a combination of low cIAP2 and low TUCAN 97% were alive and 94% disease-free, compared to 59% alive and 50% disease-free of others (p=0.00001) (FIG. 5B; DFS). Thus, the combinations of cIAP2 and Apaf1 or cIAP2 and TUCAN immunostaining data identify a subgroup of colon cancer patients with distinct survival characteristics. However, when patients with two adverse biomarkers (low Apaf1 and high TUCAN) were compared with other patients, 34% of patients with this combination of proteins and 90% of others were alive at 5 years after diagnosis (p<0.0001) (FIG. 4C). The discrepancy was even larger at the end of the survey, with 0% and 90% of those who remained alive, respectively. When combination data were examined for another pair of adverse biomarkers (cIAP2 high and Bcl-2 low), none of the patients was alive in this group 5 years after surgery, but 75% of others survived (p=004) (FIG. 4D). These results are in agreement with an outcome of the LERS data analysis.

EXAMPLE VI

Multivariate Analysis Identifies cIAP2, Apaf1, TUCAN and Bcl-2 as Independent Prognostic Indicators of Survival in Early-stage Colon Cancer This example shows that multivariate analysis confirms that cIAP2, Apaf1, TUCAN and Bcl-2 are independent prognostic indicators of survival in early-stage colon cancer.

Multivariate Cox proportional hazards models were fitted to assess whether elevated levels of biomarkers were associated with disease-free survival (DFS) and overall survival (OS). The variables were not stratified into T3NOM0 and T4NOMO subgroups due to a small number of patients involved in this study. In addition, the data mining system LERS (Learning from Examples based on Rough Sets) was employed to perform a multivariate analysis of immunohistochemical staining data.

In this project, the algorithms LEM2 was determined to be the most applicable to the data and therefore was employed for multivariate analysis. The presence of high cIAP2 and high TUCAN increased risk of death from colon cancer within this cohort of patients 2.7-fold (p=0.01) and 17-fold ((p=000004), respectively. High Apaf1 and Bcl-2 expression was associated with a decreased relative risk of dying of colon cancer by 75% (p=0.004) and 82% (p=0.00006).

When an association of protein levels with disease-free survival was assessed by multivariate analysis, cIAP2 and TUCAN maintained prognostic significance (p=0.000005, p=0.0005), with high levels of these proteins increasing risk of recurrence 6-fold and 3.4-fold, respectively. Also Apaf1 and Bcl-2 retained their significant prognostic role (p=0.006, p=0.0004), decreasing the hazard rate of colon cancer recurrence by approximately 75%. Additionally, high levels of Smac decreased the risk of recurrence by 63%. No role of Smac was evident for overall survival of patients in this cohort. Taken together, these findings indicate that immunostaining data for cIAP2, Apaf1, TUCAN, Bcl-2 and their combination can have prognostic significance for patients with early-stage colon cancer. Table 3 A–B shows multivariate analysis of DFS (A) and OS (B) in stage II colon carcinoma patients using backward stepwise Cox proportional hazards regression analysis to assess whether elevated levels of biomarkers were associated with disease-free survival or overall survival.

TABLE 3

Multivariate analysis of DFS (A) and OS (B) in stage II colon carcinoma patients

| BIOMARKER | coeffifcient | HR (95% CI) | p |
|---|---|---|---|
| | | A. DFS | |
| cIAP2 | 1.79 | 5.96 (2.78–12.8) | 0.000005 |
| Apaf1 | −1.27 | 0.28 (0.11–0.68) | 0.006 |
| TUCAN | 1.23 | 3.43 (1.6–6.55) | 0.0005 |
| Bcl-2 | −1.37 | 0.25 (0.13–0.60) | 0.007 |
| Smac | −1.00 | 0.37 (0.19–0.81) | 0.007 |
| | | B. OS | |
| cIAP2 | 0.98 | 2.66 (1.04–5.42) | 0.01 |
| Apaf1 | −1.36 | 0.26 (0.10–0.65) | 0.004 |
| TUCAN | 2.84 | 17.19 (5.12–57.48) | 0.000004 |
| Bcl-2 | −1.69 | 0.18 (0.08–0.43) | 0.00006 |

EXAMPLE VII

Expression of TUCAN in Multiple Cancer Cell Lines

This example shows that TUCAN is expressed in several tumor cell lines.

Figure 6A:
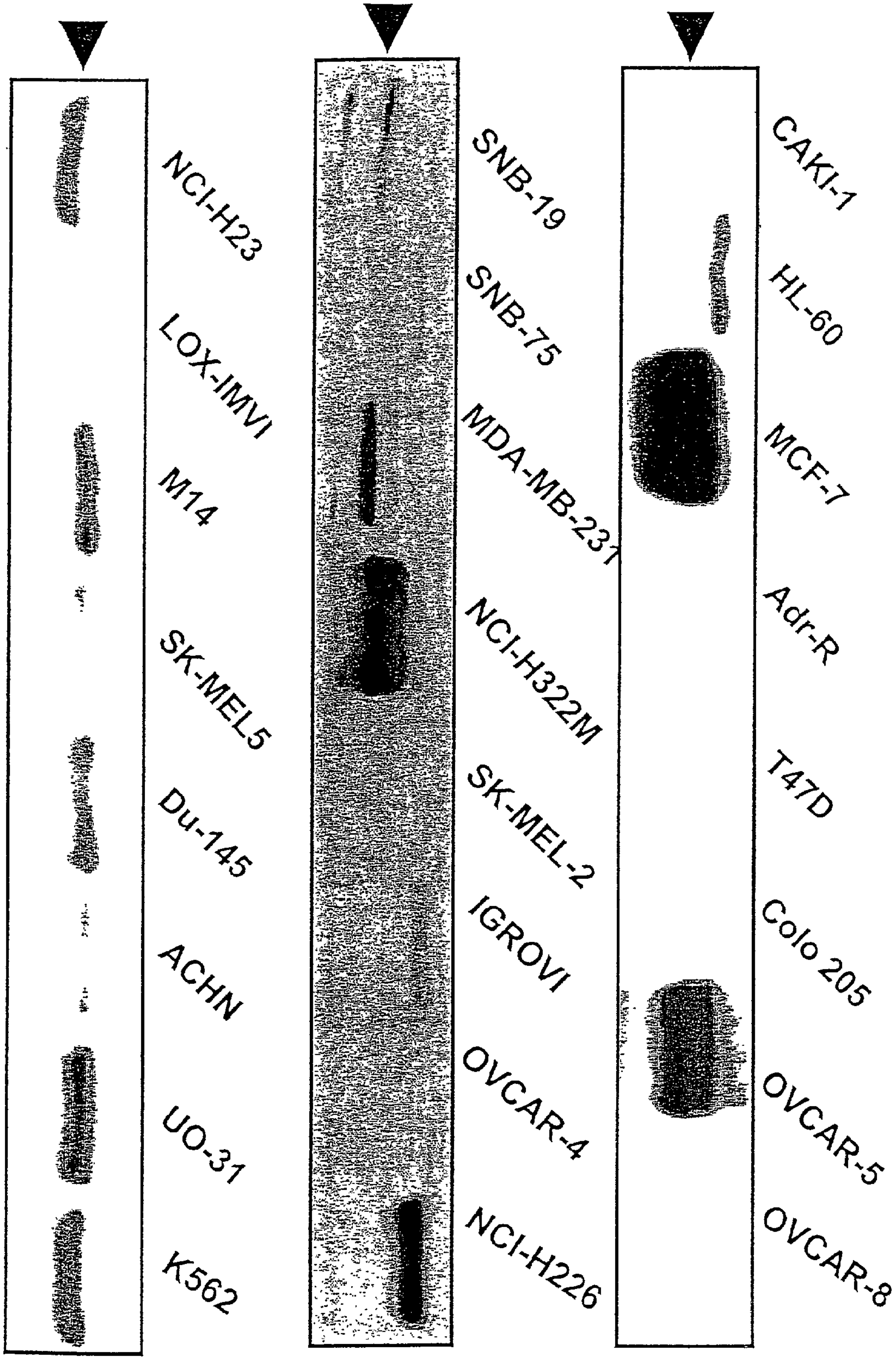
FIGS. 6A and 6B show expression of TUCAN inseveral tumor cell lines.

To determine the expression of TUCAN in cancers, the NCI panel of 60 human tumor cell lines (Weinstein, et al. Science 17:343–349 (1997)) was analyzed by immunoblotting using an antiserum specific for TUCAN (FIG. 6A). Cell lines included in the panel are shown in Table 4, below:

TABLE 4

NCI panel of 60 human tumor cell lines

| Cell Line Name | Cell Type |
|---|---|
| CCRF-CEM | Leukemia |
| HL-60 (TB) | Leukemia |
| K-562 | Leukemia |
| MOLT-4 | Leukemia |
| RPMI-8226 | Leukemia |
| SR | Leukemia |
| A549/ATCC | Non-Small Cell Lung |
| EKVX | Non-Small Cell Lung |
| HOP-62 | Non-Small Cell Lung |
| HOP-92 | Non-Small Cell Lung |

TABLE 4-continued

| NCI panel of 60 human tumor cell lines | |
|---|---|
| Cell Line Name | Cell Type |
| NCI-H226 | Non-Small Cell Lung |
| NCI-H23 | Non-Small Cell Lung |
| NCI-H322M | Non-Small Cell Lung |
| NCI-H460 | Non-Small Cell Lung |
| NCI-H522 | Non-Small Cell Lung |
| COLO 205 | Colon |
| HCC-2998 | Colon |
| HCT-116 | Colon |
| HCT-15 | Colon |
| HT29 | Colon |
| KM12 | Colon |
| SW-620 | Colon |
| SF-268 | CNS |
| SF-295 | CNS |
| SF-539 | CNS |
| SNB-19 | CNS |
| SNB-75 | CNS |
| U251 | CNS |
| LOX IMVI | Melanoma |
| MALME-3M | Melanoma |
| M14 | Melanoma |
| SK-MEL-2 | Melanoma |
| SK-MEL-28 | Melanoma |
| SK-MEL-5 | Melanoma |
| UACC-257 | Melanoma |
| UACC-62 | Melanoma |
| IGR-OV1 | Ovarian |
| OVCAR-3 | Ovarian |
| OVCAR-4 | Ovarian |
| OVCAR-5 | Ovarian |
| OVCAR-8 | Ovarian |
| SK-OV-3 | Ovarian |
| 786-0 | Renal |
| A498 | Renal |
| ACHN | Renal |
| CAKI-1 | Renal |
| RXF 393 | Renal |
| SN12C | Renal |
| TK-10 | Renal |
| UO-31 | Renal |
| PC-3 | Prostate |
| DU-145 | Prostate |
| MCF7 | Breast |
| NCI/ADR-RES | Breast |
| MDA-MB-231/ATCC | Breast |
| HS 578T | Breast |
| MDA-MB-435 | Breast |
| MDA-N | Breast |
| BT-549 | Breast |
| T-47D | Breast |

Lysates were normalized for total protein content prior to analysis. Relative levels of TUCAN protein varied widely among the tumor lines tested, with some cell lines containing especially abundant levels of this protein (for example, MCF7 breast cancer cells, OVCAR5 ovarian cancer cells, and NC1-H322M lung cancer cells). TUCAN protein also was present in HL-60 leukemia cells, SNB-19 CNS cancer cells, MDA-MB-231 breast cancer cells, IGROV1 ovarian cancer cells, NC1-H226 non-small cell lung cancer cells, NC1-H23 non small cell lung cancer cells, M14 melanoma cells, Du-145 prostate cancer cells, UO-31 renal cancer cells, and K562 leukemia cells. In some of these tumor lines, TUCAN migrated in SDS-PAGE as a broad band or as an apparent doublet, indicating that multiple forms of TUCAN protein can be present in cancer cells (FIG. 6A).

Figure 6B:
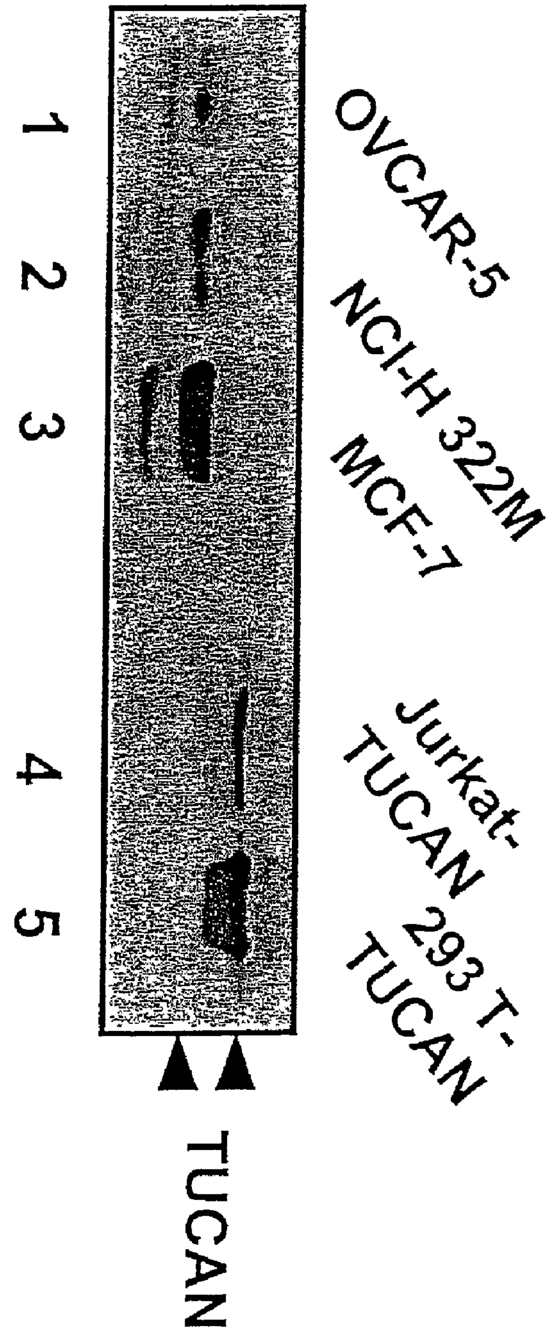

The levels of endogenous TUCAN protein in some of these cancer cell lines were compared with the transfected HEK293T and Jurkat cells. The levels of plasmid-derived TUCAN produced in transiently transfected HEK293T cells were comparable to the endogenous levels of TUCAN found in MCF7 breast cancer cells (FIG. 6B). Levels of plasmid-derived TUCAN produced in the stably transfected Jurkat cells were comparable in amount to endogenous TUCAN measured in OVCAR5 ovarian and NC1-H322M lung cancer cell lines.

In summary, TUCAN is expressed in a variety of tumor cell lines, including cancer cells obtained from human breast, ovarian, lung, CNS, leukemia, kidney, prostate, skin and colon tumors.

EXAMPLE VIII

Elevated TUCAN Expression in Colon Cancers Correlates with Reduced Patient Survival This example shows that TUCAN expression is elevated in colon cancers and that TUCAN elevation correlates with reduced colon cancer patient survival.

Figure 7:
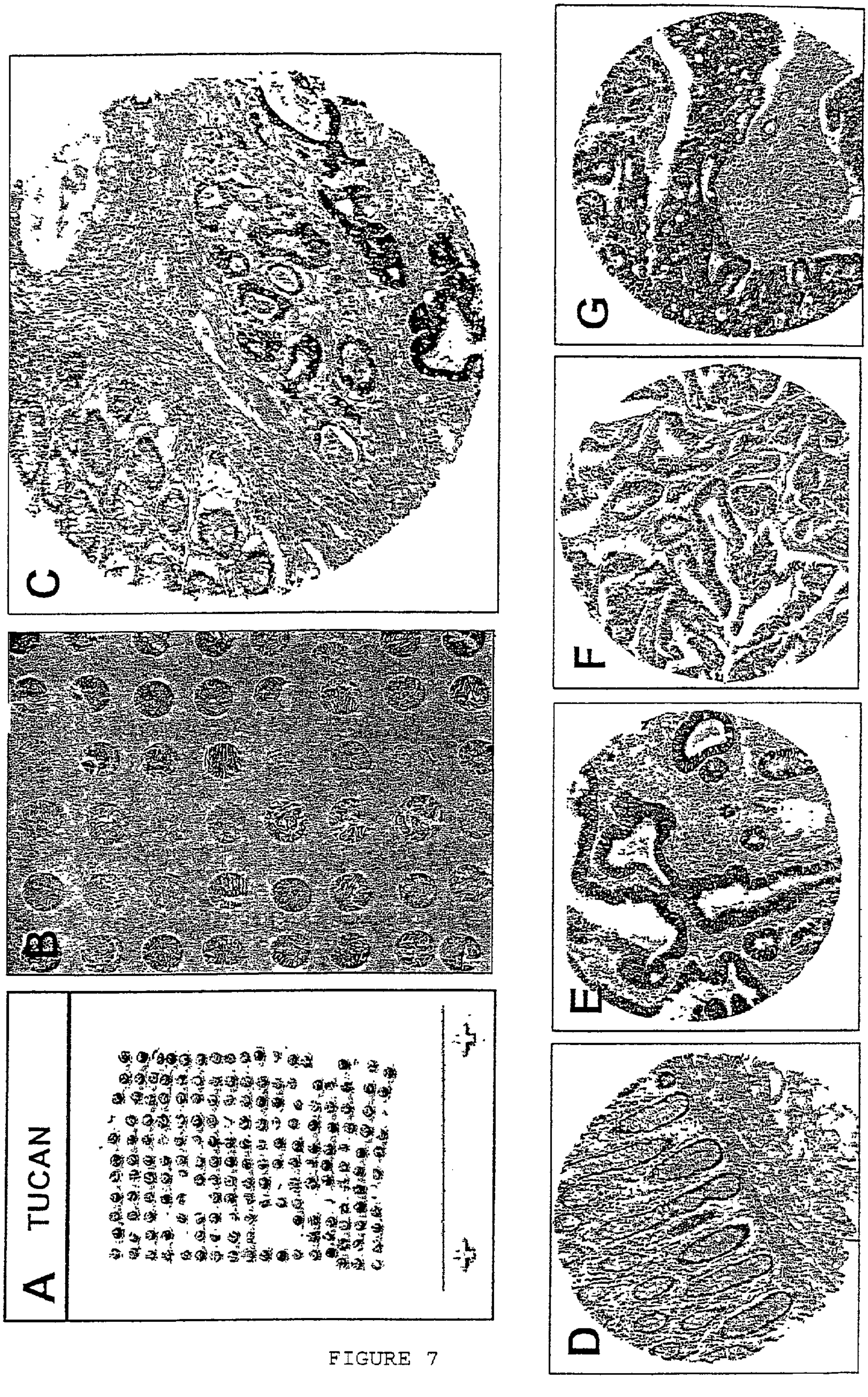
FIGS. 7A–7G show immunohistochemical analysis of TUCAN expression in colorectal cancer.

Using anti-TUCAN antibodies, the expression of TUCAN protein was analyzed by immunohistochemical methods in a collection of 102 archival paraffin-embedded colon cancer specimens derived from patients with uniform clinical stage (Duke's B; Stage II) and treatment (surgery without adjuvant chemotherapy). A tissue microarray was constructed so that all 102 tumor specimens could be analyzed on a single glass slide, thus minimizing differences in immuno-intensity due to technical artifacts (FIG. 7).

Normal human tissues for immunohistochemistry analysis were obtained from biopsy and autopsy specimens, fixed in Bouin's solution (Sigma), and embedded in paraffin. Colon carcinoma specimens were obtained from Department of Pathology, Yonsei University, College of Medicine, Seoul, Korea. Tissue samples included 102 primary tumors derived from patients who presented between 1986 and 1996 with stage II disease (Duke's B-stage), as defined by American Joint Committee on Cancer and Union Internationale Contre le Cancer (AJCC/UICC) criteria. All patients were treated by surgical resection of the involved segment of colon. No postoperative adjuvant chemotherapy was performed initially in all cases. However, chemotherapy was administered for some patients after relapse. Clinical data represent a median follow up of 60 months.

To construct colon cancer microarrays, 2–5 cylinders of 1 mm diameter tissue were taken from representative areas of archival paraffin blocks containing 8% formalin-fixed tumor and arrayed into a new recipient paraffin block with a custom-built precision instrument (Beecher Instruments, Silver Spring, Md.). Serial sections (4 um) were applied to 3-aminopropyltri-ethoxysilane (APES)-coated slides (Sigma), as described in Rentrop et al. *Histochem J.* 18:271–276 (1986).

For immunohistochemistry, dewaxed tissue sections were immunostained using a diaminobenzidine (DAB) based detection method, employing the Envision-Plus-Horse Radish Peroxidase (HRP) system (DAKO) using an automated immunostainer (Dako Universal Staining System) (Krajewski et al. *Proc. Natl. Acad. Sci. USA* 96:5752–5757 (1999)). Anti-TUCAN antibody was applied at 1:5000 (v/v). Incubation with antiserum preabsorbed with 5 ug/ml of either synthetic peptide (BUR215) or recombinant GST-CARD/TUCAN protein (BUR206) immunogen was used to verify specificity of the results. The scoring of tumor immunostaining was based on the percentage of immunopositive cells (0–100) multiplied by staining intensity score (0/1/2/3), yielding scores of 0–300.

Data were analyzed using the JMP Statistics software package (SAS Institute). An unpaired t-test method and Pearson ChiSquare test were used for correlation of TUCAN immunostaining data with the patient survival.

Of the 102 tumor specimens arrayed, 66 contained adjacent normal colonic epithelium in the same section, permitting comparisons of the intensity of TUCAN immunostaining in tumor versus normal cells. TUCAN immuno-intensity was stronger in the invasive cancer cells compared to normal colonic epithelial cells in 42 of 66 (64%) of these specimens, indicating that roughly two-thirds of colon cancers have up-regulated levels of TUCAN protein. TUCAN immunoreactivity was present diffusely through the cytosol of these cells (FIG. 7). Control staining performed with either preimmune serum or with anti-TUCAN antiserum that had been preabsorbed with TUCAN immunogen confirmed that these results were specific for anti-TUCAN.

Figure 8A:
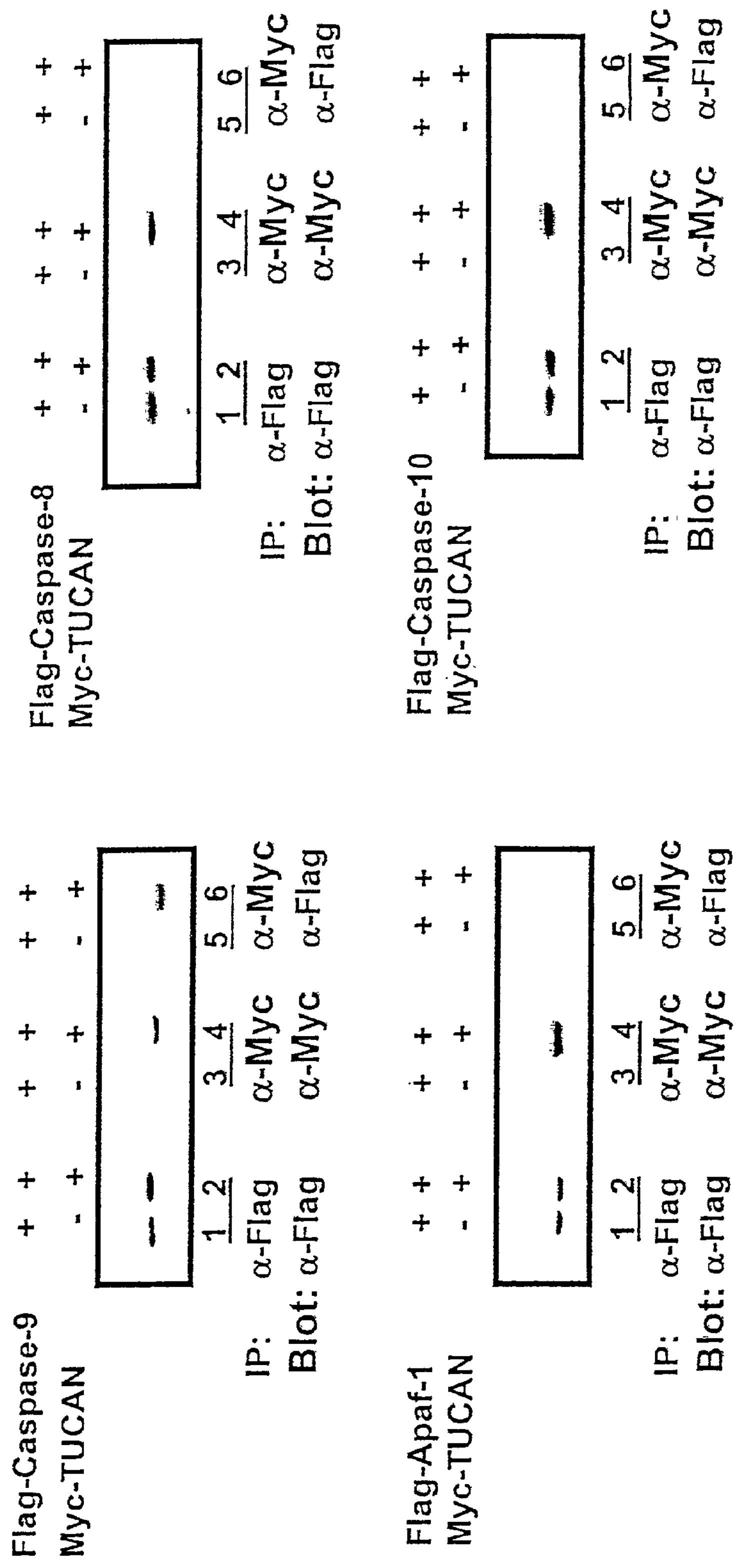
FIGS. 8A–8C show that TUCAN binds selectively to pro-caspase-9 and to itself.

Tumor immunostaining results were scored with respect to immuno-intensity (ranked on a scale of 0–3), percentage immunopositivity (0–100%), and immunoscore (which is the product of immuno-intensity and immuno-percentage), and these data were correlated with patient survival information. TUCAN immunostaining was significantly higher among patients who died of their cancer (n=31), compared to patients who remained alive without disease (n=61) or alive with recurrent disease (n=10). A summary of TUCAN immunostaining results is shown below in Table 5.

were expressed by transient transfection in HEK293T cells together with epitope-tagged pro-caspase-9 or other proteins. An inactive mutant of pro-caspase-9 in which the catalytic cysteine was substitute with alanine (Cys287/Ala) was employed for these experiments to avoid induction of apoptosis (Cardone et al. *Science* 282:1318–1321 (1998)). Cell lysates were prepared from transfected cells and immunoprecipitations were performed using anti-Flag or anti-Myc antibodies, followed by SDS-PAGE/immunoblot analysis. Representative results are presented in FIG. 8A, which shows that TUCAN co-immunoprecipitated with pro-Caspase-9 but not the CARD-containing protein Apaf1. TUCAN also did not co-immunoprecipitate with the CARD-containing proteins pro-Caspase-1, pro-Caspase-2, Nodl, CED4, NAC, Cardiak, Raidd, Bcl10, CLAN, CARD9, cIAP1 and cIAP2. Moreover, TUCAN did not associate non-specifically with caspases, as co-immunoprecipitation experiments did not reveal interactions with the DED-containing caspases, pro-caspase-8 and-10 (FIG. 8A).

Figure 8B:
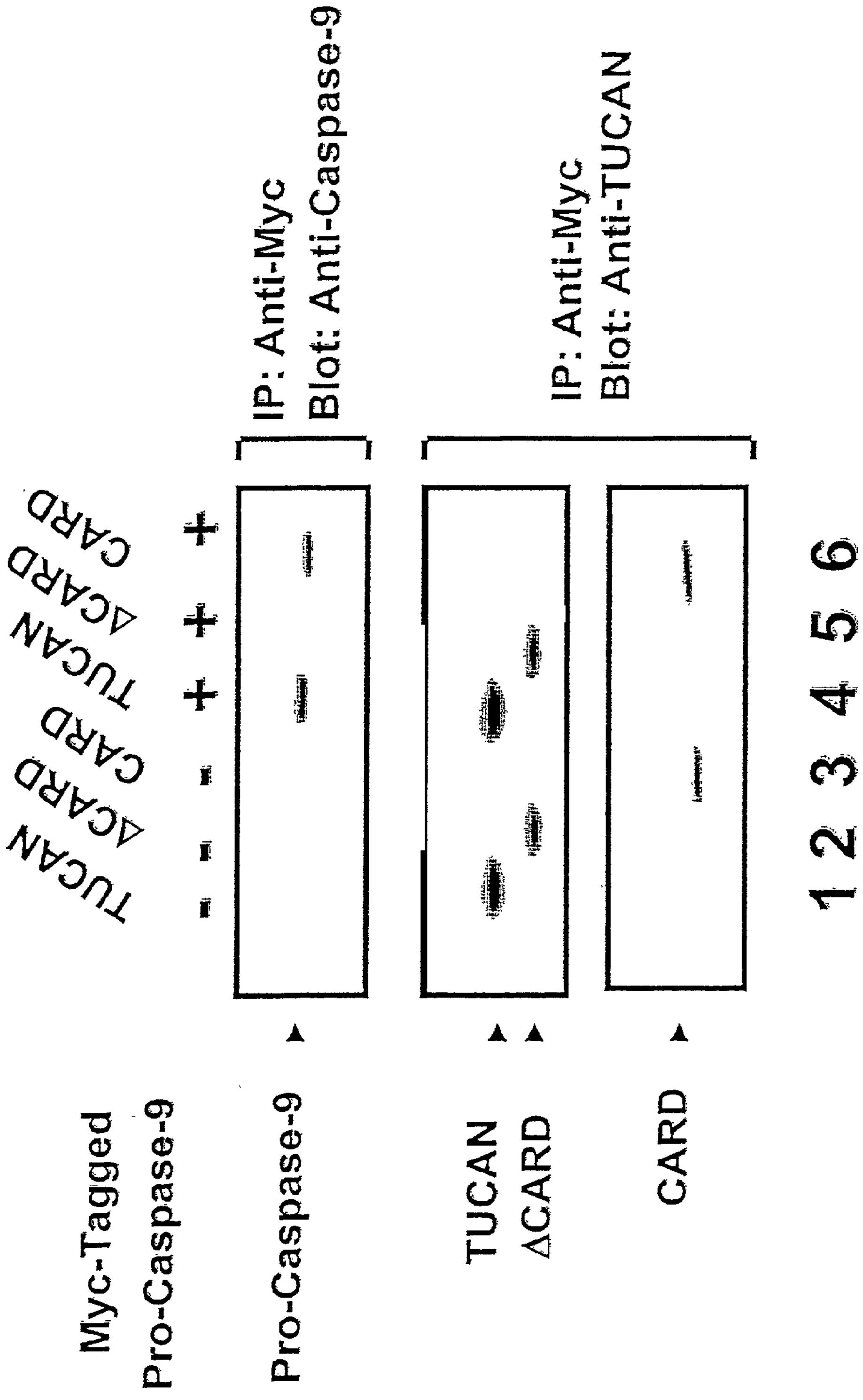

To determine the role of the CARD domain within TUCAN for interactions with pro-Caspase-9, fragments of TUCAN were expressed. The TUCAN fragments contained essentially only the CARD (residues 345–431) or lacked the CARD (residues 1–337) (ΔCARD). Pro-Caspase-9 co-immunoprecipitated with full-length TUCAN and the CARD only fragment but not the ΔCARD fragment of TUCAN (FIG. 8B). Thus, the CARD domain of TUCAN is necessary

TABLE 5

Summary of TUCAN Immunostaining Results

| Patient Status | n | % Immunopositivity Mean ± SE | % Immunopositivity Median | Immunointensity Mean ± SE | Immunointensity Median | Immunoscore Mean ± SE | Immunoscore Median |
|---|---|---|---|---|---|---|---|
| Alive without disease | 61 | 58 ± 3 | 60 | 1.4 ± 0.1 | 1 | 92 ± 9 | 80 |
| Alive with disease | 10 | 54 ± 7 | 55 | 1.3 ± 0.2 | 1 | 73 ± 21 | 65 |
| Dead from disease | 31 | 90 ± 4 | 95 | 2.5 ± 0.1 | 3 | 224 ± 12 | 240 |
| p-values | 102 | p < .0001 | | p < .0001 | | p < .0001 | |

In summary, TUCAN expression is abnormally elevated in a substantial proportion of early-stage colon cancers. Furthermore, elevated TUCAN expression correlates with reduced patient survival.

EXAMPLE IX

TUCAN Binds Selectively to Pro-Caspase-9 and to Itself

This example shows that TUCAN binds selectively to Pro-Caspase-9 and to itself. Since CARDS are known for their ability to bind each other, TUCAN was tested for interactions with the CARD-containing proteins pro-Caspase-1, pro-Caspase-2, pro-Caspase-9, Apaf1, Nod1 (CARD4), CED4, NAC (DEFCAP), Cardiak (RIP2), Raidd (CRADD), Bcl10 (CIPER; huE10), cIAP1, cIAP2, CLAN, CARD9, and itself. Among these, TUCAN associated only with pro-Caspase-9 and itself.

Figure 8C:
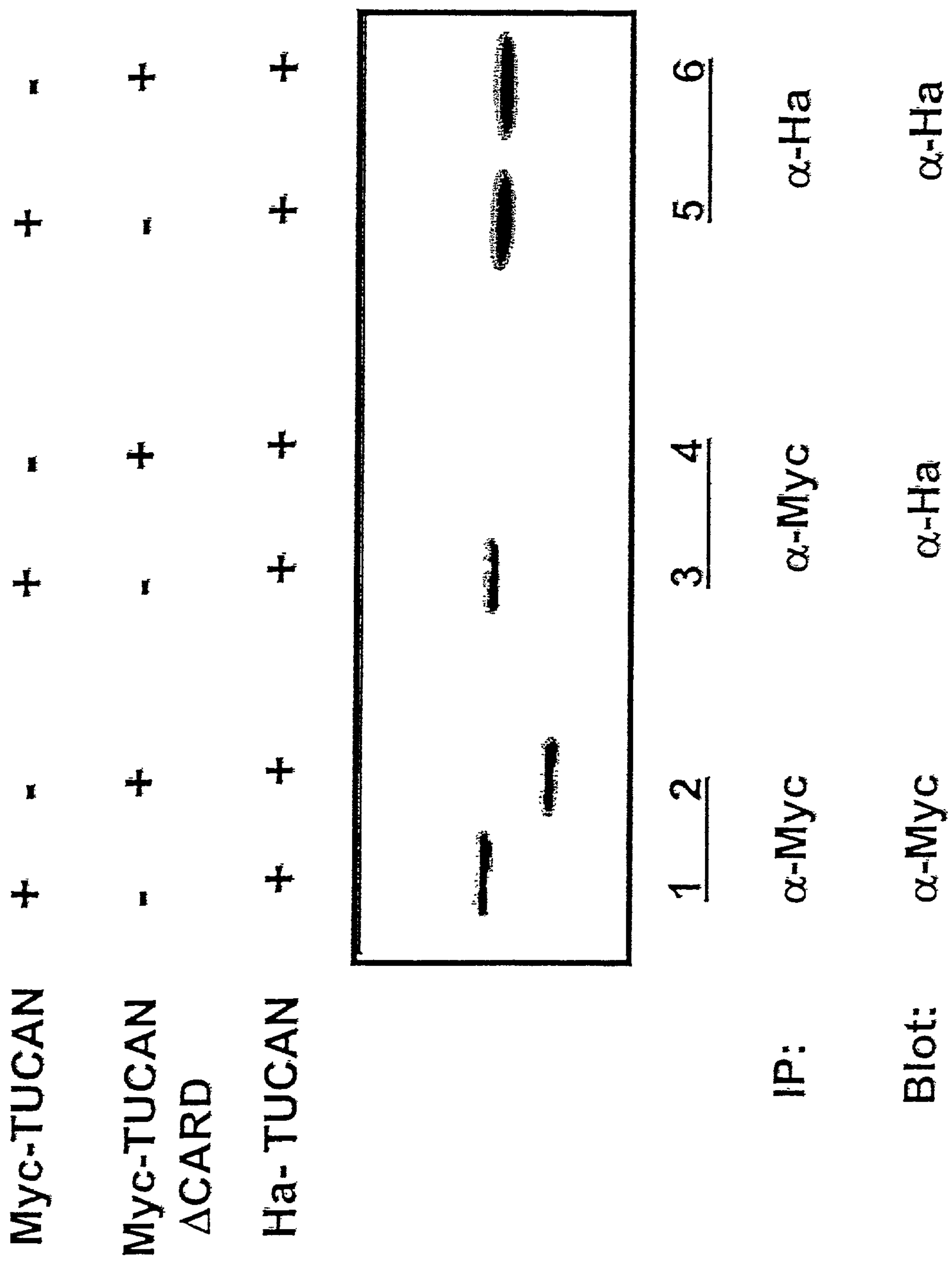

FIG. 8 shows representative results from co-immunoprecipitation experiments performed using TUCAN containing either Flag or Myc epitope tags. The TUCAN polypeptides and sufficient for association with pro-Caspase-9. Self-association of TUCAN was also confirmed by co-immunoprecipitation experiments, using HA and Myc-tagged proteins and contrasting the full-length, CARD-only, and ΔCARD proteins. Full-length TUCAN interacted with full-length TUCAN and the CARD-only fragment but not the ΔCARD fragment (FIG. 8C). Thus, the CARD domain of TUCAN is necessary and sufficient for self-association.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method for determining the prognosis for survival for a colon cancer patient having stage II colon carcinoma, comprising:

(a) measuring a level of TUCAN polypeptide in a colon cancer cell-containing sample from said colon cancer patient, and (b) comparing the level of TUCAN polypeptide in said sample to a reference level of TUCAN polypeptide from normal colon tissue, wherein a lower level of TUCAN polypeptide relative to said reference level correlates with increased survival of said patient.

2. The method of claim 1, wherein said survival is overall survival.

3. The method of claim 1, wherein said survival is disease-free survival.

4. The method of claim 1, wherein said sample is colon tumor tissue.

5. The method of claim 1, wherein said sample is a fluid selected from the group consisting of blood, serum, urine, semen and stool.

6. The method of claim 1, wherein a level of said TUCAN polypeptide is measured using an antibody specifically reactive with TUCAN.

7. The method of claim 1, wherein said level of TUCAN polypeptide is used to determine if said patient is at risk for relapse.

8. The method of claim 1, wherein said level of TUCAN polypeptide is used to determine a proper course of treatment for said patient.

9. A method of determining a prognosis for survival for a colon cancer patient having stage II colon carcinoma, comprising:

(a) measuring levels of TUCAN polypeptide and one or more biomarker polypeptides selected from the group consisting of cIAP2, Apaf1, Bcl-2 and Smac in a colon cancer cell-containing sample from said colon cancer patient, and (b) comparing the level of TUCAN polypeptide and the one or more selected biomarker polypeptides in said sample to a reference level of TUCAN polypeptide and said one or more selected biomarker polypeptides from normal colon tissue, wherein a lower level of TUCAN polypeptide and a higher level of any of Apaf1, Bcl-2, or Smac, or a lower level of TUCAN polypeptide and a lower level of cIAP2 in said sample relative to said reference level correlate with increased survival of said patient.

10. The method of claim 9, wherein said survival is overall survival.

11. The method of claim 9, wherein said survival is disease-free survival.

12. The method of claim 9, wherein cIAP2 is a selected biomarker.

13. The method of claim 9, wherein Apaf1 is a selected biomarker.

14. The method of claim 9, wherein Bcl-2 is a selected biomarker.

15. The method of claim 9 wherein Smac is a selected biomarker.

16. The method of claim 9, wherein said sample is colon tumor tissue.

17. The method of claim 9, wherein said sample is a fluid selected from the group consisting of blood, serum, semen, urine, and stool.

18. The method of claim 9, wherein a level of TUCAN or a biomarker polypeptide is measured using an antibody specifically reactive with TUCAN or the biomarker polypeptide.

19. The method of claim 9, wherein the levels of TUCAN polypeptide and one or more biomarker polypeptide are used to determine if said patient is at risk for relapse.

20. The method of claim 9, wherein the levels of TUCAN polypeptide and one or more biomarker polypeptide are used to determine a proper course of treatment for said patient.

21. The method of claim 9, further comprising selecting two or more biomarkers from the group consisting of cIAP2, Apaf1, Bcl-2 and Smac.

22. A method of determining a prognosis for survival for a colon cancer patient having stage II colon carcinoma, comprising:

(a) measuring a level of TUCAN polypeptide in a colon cancer cell-containing sample from said colon cancer patient;

(b) comparing the level of TUCAN polypeptide in said sample to a reference level of TUCAN polypeptide from normal colon tissue; and (c) classifying said patient as belonging to either a first or second group of patients, wherein said first group of patients having lower levels of TUCAN polypeptide relative to said reference level is classified as having an increased likelihood of survival compared to said second group of patients having higher levels of TUCAN polypeptide relative to said reference level.

23. The method of claim 22, wherein said survival is overall survival.

24. The method of claim 22, wherein said survival is disease-free survival.

25. The method of claim 22, wherein said sample is colon tumor tissue.

26. The method of claim 22, wherein said sample is a fluid selected from the group consisting of blood, serum, urine, semen and stool.

27. The method of claim 22, wherein a level of a TUCAN polypeptide is measured using an antibody specifically reactive with TUCAN polypeptide.

28. The method of claim 22, further comprising:

(a) determining a level of cIAP2 polypeptide in said colon cancer cell-containing sample from said colon cancer patient, (b) comparing the level of cIAP2 in said sample to a reference level of cIAP2 from normal colon tissue; and (c) classifying said patient as belonging to either a first or second group of patients, wherein said first group of patients having lower levels of TUCAN polypeptide and lower levels of cIAP2 polypeptide relative to said reference levels is classified as having increased likelihood of survival compared to said second group of patients having higher levels of TUCAN polypeptide and higher levels of cIAP2 polypeptide relative to said reference levels.

29. The method of claim 22, further comprising:

(a) determining a level of a biomarker polypeptide selected from the group consisting of Apaf1, Smac and Bcl-2 in said colon cancer cell-containing sample from said colon cancer patient, (b) comparing the level of said biomarker polypeptide in said sample to a reference level of said biomarker polypeptide from normal colon tissue; and (c) classifying said patient as belonging to either a first or second group of patients, wherein said first group of patients having lower levels of TUCAN polypeptide and higher levels of any of Apaf1, Smac or Bcl-2 polypeptide relative to said reference levels is classified as having increased likelihood of survival compared to said second group of patients having higher levels of TUCAN polypeptide and lower levels of Apaf1, Smac, or Bcl-2 polypeptide relative to said reference levels.

30. The method of claim 29, wherein Apaf1 is a selected biomarker.

31. The method of claim 29, wherein Bcl-2 is a selected biomarker.

32. The method of claim 29, wherein Smac is a selected biomarker.

* * * * *

SEQUENCE LISTING

<160> NUMBER OF SEQ ID NOS: 15

<210> SEQ ID NO 1
<211> LENGTH: 1487
<212> TYPE: DNA
<213> ORGANISM: Homo sapiens
<220> FEATURE:
<221> NAME/KEY: CDS
<222> LOCATION: (1)...(1293)

<400> SEQUENCE: 1 atg atg aga cag agg cag agc cat tat tgt tcc gtg ctg ttc ctg agt 48
Met Met Arg Gln Arg Gln Ser His Tyr Cys Ser Val Leu Phe Leu Ser
1 5 10 15 gtc aac tat ctg ggg ggg aca ttc cca gga gac att tgc tca gaa gag 96
Val Asn Tyr Leu Gly Gly Thr Phe Pro Gly Asp Ile Cys Ser Glu Glu
20 25 30 aat caa ata gtt tcc tct tat gct tct aaa gtc tgt ttt gag atc gaa 144
Asn Gln Ile Val Ser Ser Tyr Ala Ser Lys Val Cys Phe Glu Ile Glu
35 40 45 gaa gat tat aaa aat cgt cag ttt ctg ggg cct gaa gga aat gtg gat 192
Glu Asp Tyr Lys Asn Arg Gln Phe Leu Gly Pro Glu Gly Asn Val Asp
50 55 60 gtt gag ttg att gat aag agc aca aac aga tac agc gtt tgg ttc ccc 240
Val Glu Leu Ile Asp Lys Ser Thr Asn Arg Tyr Ser Val Trp Phe Pro
65 70 75 80 act gct ggc tgg tat ctg tgg tca gcc aca ggc ctc ggc ttc ctg gta 288
Thr Ala Gly Trp Tyr Leu Trp Ser Ala Thr Gly Leu Gly Phe Leu Val
85 90 95 agg gat gag gtc aca gtg acg att gcg ttt ggt tcc tgg agt cag cac 336
Arg Asp Glu Val Thr Val Thr Ile Ala Phe Gly Ser Trp Ser Gln His
100 105 110 ctg gcc ctg gac ctg cag cac cat gaa cag tgg ctg gtg ggc ggc ccc 384
Leu Ala Leu Asp Leu Gln His His Glu Gln Trp Leu Val Gly Gly Pro
115 120 125 ttg ttt gat gtc act gca gag cca gag gag gct gtc gcc gaa atc cac 432
Leu Phe Asp Val Thr Ala Glu Pro Glu Glu Ala Val Ala Glu Ile His
130 135 140 ctc ccc cac ttc atc tcc ctc caa ggt gag gtg gac gtc tcc tgg ttt 480
Leu Pro His Phe Ile Ser Leu Gln Gly Glu Val Asp Val Ser Trp Phe
145 150 155 160 ctc gtt gcc cat ttt aag aat gaa ggg atg gtc ctg gag cat cca gcc 528
Leu Val Ala His Phe Lys Asn Glu Gly Met Val Leu Glu His Pro Ala
165 170 175 cgg gtg gag cct ttc tat gct gtc ctg gaa agc ccc agc ttc tct ctg 576
Arg Val Glu Pro Phe Tyr Ala Val Leu Glu Ser Pro Ser Phe Ser Leu
180 185 190 atg ggc atc ctg ctg cgg atc gcc agt ggg act cgc ctc tcc atc ccc 624
Met Gly Ile Leu Leu Arg Ile Ala Ser Gly Thr Arg Leu Ser Ile Pro
195 200 205 atc act tcc aac aca ttg atc tat tat cac ccc cac ccc gaa gat att 672
Ile Thr Ser Asn Thr Leu Ile Tyr Tyr His Pro His Pro Glu Asp Ile
210 215 220 aag ttc cac ttg tac ctt gtc ccc agc gac gcc ttg cta aca aag gcg 720
Lys Phe His Leu Tyr Leu Val Pro Ser Asp Ala Leu Leu Thr Lys Ala
225 230 235 240 ata gat gat gag gaa gat cgc ttc cat ggt gtg cgc ctg cag act tcg 768
Ile Asp Asp Glu Glu Asp Arg Phe His Gly Val Arg Leu Gln Thr Ser
245 250 255

-continued

```
ccc cca atg gaa ccc ctg aac ttt ggt tcc agt tat att gtg tct aat      816
Pro Pro Met Glu Pro Leu Asn Phe Gly Ser Ser Tyr Ile Val Ser Asn
            260                 265                 270

tct gct aac ctg aaa gta atg ccc aag gag ttg aaa ttg tcc tac agg      864
Ser Ala Asn Leu Lys Val Met Pro Lys Glu Leu Lys Leu Ser Tyr Arg
        275                 280                 285

agc cct gga gaa att cag cac ttc tca aaa ttc tat gct ggg cag atg      912
Ser Pro Gly Glu Ile Gln His Phe Ser Lys Phe Tyr Ala Gly Gln Met
    290                 295                 300

aag gaa ccc att caa ctt gag att act gaa aaa aga cat ggg act ttg      960
Lys Glu Pro Ile Gln Leu Glu Ile Thr Glu Lys Arg His Gly Thr Leu
305                 310                 315                 320

gtg tgg gat act gag gtg aag cca gtg gat ctc cag ctt gta gct gca     1008
Val Trp Asp Thr Glu Val Lys Pro Val Asp Leu Gln Leu Val Ala Ala
                325                 330                 335

tca gcc cct cct cct ttc tca ggt gca gcc ttt gtg aag gag aac cac     1056
Ser Ala Pro Pro Pro Phe Ser Gly Ala Ala Phe Val Lys Glu Asn His
            340                 345                 350

cgg caa ctc caa gcc agg atg ggg gac ctg aaa ggg gtg ctc gat gat     1104
Arg Gln Leu Gln Ala Arg Met Gly Asp Leu Lys Gly Val Leu Asp Asp
        355                 360                 365

ctc cag gac aat gag gtt ctt act gag aat gag aag gag ctg gtg gag     1152
Leu Gln Asp Asn Glu Val Leu Thr Glu Asn Glu Lys Glu Leu Val Glu
    370                 375                 380

cag gaa aag aca cgg cag agc aag aat gag gcc ttg ctg agc atg gtg     1200
Gln Glu Lys Thr Arg Gln Ser Lys Asn Glu Ala Leu Leu Ser Met Val
385                 390                 395                 400

gag aag aaa ggg gac ctg gcc ctg gac gtg ctc ttc aga agc att agt     1248
Glu Lys Lys Gly Asp Leu Ala Leu Asp Val Leu Phe Arg Ser Ile Ser
                405                 410                 415

gaa agg gac cct tac ctc gtg tcc tat ctt aga cag cag aat ttg         1293
Glu Arg Asp Pro Tyr Leu Val Ser Tyr Leu Arg Gln Gln Asn Leu
            420                 425                 430

taaaatgagt cagttaggta gtctggaaga gagaatccag cgttctcatt ggaaatggat   1353

aaacagaaat gtgatcattg atttcagtgt tcaagacaga agaagactgg gtaacatcta   1413

tcacacaggc tttcaggaca gacttgtaac ctggcatgta cctattgact gtatcctcat   1473

gcattttcct caag                                                     1487


<210> SEQ ID NO 2
<211> LENGTH: 431
<212> TYPE: PRT
<213> ORGANISM: Homo sapiens

<400> SEQUENCE: 2

Met Met Arg Gln Arg Gln Ser His Tyr Cys Ser Val Leu Phe Leu Ser
 1               5                  10                  15

Val Asn Tyr Leu Gly Gly Thr Phe Pro Gly Asp Ile Cys Ser Glu Glu
            20                  25                  30

Asn Gln Ile Val Ser Ser Tyr Ala Ser Lys Val Cys Phe Glu Ile Glu
        35                  40                  45

Glu Asp Tyr Lys Asn Arg Gln Phe Leu Gly Pro Glu Gly Asn Val Asp
    50                  55                  60

Val Glu Leu Ile Asp Lys Ser Thr Asn Arg Tyr Ser Val Trp Phe Pro
65                  70                  75                  80

Thr Ala Gly Trp Tyr Leu Trp Ser Ala Thr Gly Leu Gly Phe Leu Val
                85                  90                  95

Arg Asp Glu Val Thr Val Thr Ile Ala Phe Gly Ser Trp Ser Gln His
```

-continued

```
            100                 105                 110

Leu Ala Leu Asp Leu Gln His His Glu Gln Trp Leu Val Gly Gly Pro
        115                 120                 125

Leu Phe Asp Val Thr Ala Glu Pro Glu Glu Ala Val Ala Glu Ile His
    130                 135                 140

Leu Pro His Phe Ile Ser Leu Gln Gly Glu Val Asp Val Ser Trp Phe
145                 150                 155                 160

Leu Val Ala His Phe Lys Asn Glu Gly Met Val Leu Glu His Pro Ala
                165                 170                 175

Arg Val Glu Pro Phe Tyr Ala Val Leu Glu Ser Pro Ser Phe Ser Leu
            180                 185                 190

Met Gly Ile Leu Leu Arg Ile Ala Ser Gly Thr Arg Leu Ser Ile Pro
        195                 200                 205

Ile Thr Ser Asn Thr Leu Ile Tyr Tyr His Pro His Pro Glu Asp Ile
    210                 215                 220

Lys Phe His Leu Tyr Leu Val Pro Ser Asp Ala Leu Leu Thr Lys Ala
225                 230                 235                 240

Ile Asp Asp Glu Glu Asp Arg Phe His Gly Val Arg Leu Gln Thr Ser
                245                 250                 255

Pro Pro Met Glu Pro Leu Asn Phe Gly Ser Ser Tyr Ile Val Ser Asn
            260                 265                 270

Ser Ala Asn Leu Lys Val Met Pro Lys Glu Leu Lys Leu Ser Tyr Arg
        275                 280                 285

Ser Pro Gly Glu Ile Gln His Phe Ser Lys Phe Tyr Ala Gly Gln Met
    290                 295                 300

Lys Glu Pro Ile Gln Leu Glu Ile Thr Glu Lys Arg His Gly Thr Leu
305                 310                 315                 320

Val Trp Asp Thr Glu Val Lys Pro Val Asp Leu Gln Leu Val Ala Ala
                325                 330                 335

Ser Ala Pro Pro Pro Phe Ser Gly Ala Ala Phe Val Lys Glu Asn His
            340                 345                 350

Arg Gln Leu Gln Ala Arg Met Gly Asp Leu Lys Gly Val Leu Asp Asp
        355                 360                 365

Leu Gln Asp Asn Glu Val Leu Thr Glu Asn Glu Lys Glu Leu Val Glu
    370                 375                 380

Gln Glu Lys Thr Arg Gln Ser Lys Asn Glu Ala Leu Leu Ser Met Val
385                 390                 395                 400

Glu Lys Lys Gly Asp Leu Ala Leu Asp Val Leu Phe Arg Ser Ile Ser
                405                 410                 415

Glu Arg Asp Pro Tyr Leu Val Ser Tyr Leu Arg Gln Gln Asn Leu
            420                 425                 430


<210> SEQ ID NO 3
<211> LENGTH: 87
<212> TYPE: PRT
<213> ORGANISM: Homo sapiens

<400> SEQUENCE: 3

Ala Ala Phe Val Lys Glu Asn His Arg Gln Leu Gln Ala Arg Met Gly
 1               5                  10                  15

Asp Leu Lys Gly Val Leu Asp Asp Leu Gln Asp Asn Glu Val Leu Thr
            20                  25                  30

Glu Asn Glu Lys Glu Leu Val Glu Gln Glu Lys Thr Arg Gln Ser Lys
        35                  40                  45
```

-continued

```
Asn Glu Ala Leu Leu Ser Met Val Glu Lys Lys Gly Asp Leu Ala Leu
    50                  55                  60

Asp Val Leu Phe Arg Ser Ile Ser Glu Arg Asp Pro Tyr Leu Val Ser
65                  70                  75                  80

Tyr Leu Arg Gln Gln Asn Leu
                85


<210> SEQ ID NO 4
<211> LENGTH: 416
<212> TYPE: PRT
<213> ORGANISM: Homo sapiens

<400> SEQUENCE: 4

Met Asp Glu Ala Asp Arg Arg Leu Leu Arg Arg Cys Arg Leu Arg Leu
 1               5                  10                  15

Val Glu Glu Leu Gln Val Asp Gln Leu Trp Asp Ala Leu Leu Ser Ser
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Pro His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335
```

-continued

```
Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415


<210> SEQ ID NO 5
<211> LENGTH: 3164
<212> TYPE: DNA
<213> ORGANISM: Homo sapiens
<220> FEATURE:
<221> NAME/KEY: CDS
<222> LOCATION: (724)...(2538)

<400> SEQUENCE: 5

gaattcaaaa tgtcttcagt tgtaaatctt accattattt tacgtacctc taagaaataa      60

aagtgcttct aattaaaata tgatgtcatt aattatgaaa tacttcttga taacagaagt     120

ttaaaatagc catcttagaa tcagtgaaat atggtaatgt attattttcc tcctttgagt     180

taggtcttgt gctttttttt cctggccact aaatttcaca atttccaaaa agcaaaataa     240

acatattctg aatatttttg ctgtgaaaca cttgacagca gagctttcca ccatgaaaag     300

aagcttcatg agtcacacat tacatctttg ggttgattga atgccactga aacattctag     360

tagcctggag aagttgacct acctgtggag atgcctgcca ttaaatggca tcctgatggc     420

ttaatacaca tcactcttct gtgaagggtt ttaattttca acacagctta ctctgtagca     480

tcatgtttac attgtatgta taaagattat acaaaggtgc aattgtgtat ttcttcctta     540

aaatgtatca gtataggatt tagaatctcc atgttgaaac tctaaatgca tagaaataaa     600

aataataaaa aatttttcat tttggctttt cagcctagta ttaaaactga taaaagcaaa     660

gccatgcaca aaactacctc cctagagaaa ggctagtccc ttttcttccc cattcatttc     720

att atg aac ata gta gaa aac agc ata ttc tta tca aat ttg atg aaa      768
    Met Asn Ile Val Glu Asn Ser Ile Phe Leu Ser Asn Leu Met Lys
     1               5                  10                  15

agc gcc aac acg ttt gaa ctg aaa tac gac ttg tca tgt gaa ctg tac      816
Ser Ala Asn Thr Phe Glu Leu Lys Tyr Asp Leu Ser Cys Glu Leu Tyr
                20                  25                  30

cga atg tct acg tat tcc act ttt cct gct ggg gtc cct gtc tca gaa      864
Arg Met Ser Thr Tyr Ser Thr Phe Pro Ala Gly Val Pro Val Ser Glu
            35                  40                  45

agg agt ctt gct cgc gct ggt ttc tat tac act ggt gtg aat gac aag      912
Arg Ser Leu Ala Arg Ala Gly Phe Tyr Tyr Thr Gly Val Asn Asp Lys
        50                  55                  60

gtc aaa tgc ttc tgt tgt ggc ctg atg ctg gat aac tgg aaa aga gga      960
Val Lys Cys Phe Cys Cys Gly Leu Met Leu Asp Asn Trp Lys Arg Gly
     65                  70                  75

gac agt cct act gaa aag cat aaa aag ttg tat cct agc tgc aga ttc     1008
Asp Ser Pro Thr Glu Lys His Lys Lys Leu Tyr Pro Ser Cys Arg Phe
 80                  85                  90                  95

gtt cag agt cta aat tcc gtt aac aac ttg gaa gct acc tct cag cct     1056
Val Gln Ser Leu Asn Ser Val Asn Asn Leu Glu Ala Thr Ser Gln Pro
                100                 105                 110
```

-continued

```
act ttt cct tct tca gta aca aat tcc aca cac tca tta ctt ccg ggt      1104
Thr Phe Pro Ser Ser Val Thr Asn Ser Thr His Ser Leu Leu Pro Gly
            115                 120                 125

aca gaa aac agt gga tat ttc cgt ggc tct tat tca aac tct cca tca      1152
Thr Glu Asn Ser Gly Tyr Phe Arg Gly Ser Tyr Ser Asn Ser Pro Ser
        130                 135                 140

aat cct gta aac tcc aga gca aat caa gat ttt tct gcc ttg atg aga      1200
Asn Pro Val Asn Ser Arg Ala Asn Gln Asp Phe Ser Ala Leu Met Arg
    145                 150                 155

agt tcc tac cac tgt gca atg aat aac gaa aat gcc aga tta ctt act      1248
Ser Ser Tyr His Cys Ala Met Asn Asn Glu Asn Ala Arg Leu Leu Thr
160                 165                 170                 175

ttt cag aca tgg cca ttg act ttt ctg tcg cca aca gat ctg gca aaa      1296
Phe Gln Thr Trp Pro Leu Thr Phe Leu Ser Pro Thr Asp Leu Ala Lys
                180                 185                 190

gca ggc ttt tac tac ata gga cct gga gac aga gtg gct tgc ttt gcc      1344
Ala Gly Phe Tyr Tyr Ile Gly Pro Gly Asp Arg Val Ala Cys Phe Ala
            195                 200                 205

tgt ggt gga aaa ttg agc aat tgg gaa ccg aag gat aat gct atg tca      1392
Cys Gly Gly Lys Leu Ser Asn Trp Glu Pro Lys Asp Asn Ala Met Ser
        210                 215                 220

gaa cac ctg aga cat ttt ccc aaa tgc cca ttt ata gaa aat cag ctt      1440
Glu His Leu Arg His Phe Pro Lys Cys Pro Phe Ile Glu Asn Gln Leu
    225                 230                 235

caa gac act tca aga tac aca gtt tct aat ctg agc atg cag aca cat      1488
Gln Asp Thr Ser Arg Tyr Thr Val Ser Asn Leu Ser Met Gln Thr His
240                 245                 250                 255

gca gcc cgc ttt aaa aca ttc ttt aac tgg ccc tct agt gtt cta gtt      1536
Ala Ala Arg Phe Lys Thr Phe Phe Asn Trp Pro Ser Ser Val Leu Val
                260                 265                 270

aat cct gag cag ctt gca agt gcg ggt ttt tat tat gtg ggt aac agt      1584
Asn Pro Glu Gln Leu Ala Ser Ala Gly Phe Tyr Tyr Val Gly Asn Ser
            275                 280                 285

gat gat gtc aaa tgc ttt tgc tgt gat ggt gga ctc agg tgt tgg gaa      1632
Asp Asp Val Lys Cys Phe Cys Cys Asp Gly Gly Leu Arg Cys Trp Glu
        290                 295                 300

tct gga gat gat cca tgg gtt caa cat gcc aag tgg ttt cca agg tgt      1680
Ser Gly Asp Asp Pro Trp Val Gln His Ala Lys Trp Phe Pro Arg Cys
    305                 310                 315

gag tac ttg ata aga att aaa gga cag gag ttc atc cgt caa gtt caa      1728
Glu Tyr Leu Ile Arg Ile Lys Gly Gln Glu Phe Ile Arg Gln Val Gln
320                 325                 330                 335

gcc agt tac cct cat cta ctt gaa cag ctg cta tcc aca tca gac agc      1776
Ala Ser Tyr Pro His Leu Leu Glu Gln Leu Leu Ser Thr Ser Asp Ser
                340                 345                 350

cca gga gat gaa aat gca gag tca tca att atc cat ttt gaa cct gga      1824
Pro Gly Asp Glu Asn Ala Glu Ser Ser Ile Ile His Phe Glu Pro Gly
            355                 360                 365

gaa gac cat tca gaa gat gca atc atg atg aat act cct gtg att aat      1872
Glu Asp His Ser Glu Asp Ala Ile Met Met Asn Thr Pro Val Ile Asn
        370                 375                 380

gct gcc gtg gaa atg ggc ttt agt aga agc ctg gta aaa cag aca gtt      1920
Ala Ala Val Glu Met Gly Phe Ser Arg Ser Leu Val Lys Gln Thr Val
    385                 390                 395

cag aga aaa atc cta gca act gga gag aat tat aga cta gtc aat gat      1968
Gln Arg Lys Ile Leu Ala Thr Gly Glu Asn Tyr Arg Leu Val Asn Asp
400                 405                 410                 415

ctt gtg tta gac tta ctc aat gca gaa gat gaa ata agg gaa gag gag      2016
Leu Val Leu Asp Leu Leu Asn Ala Glu Asp Glu Ile Arg Glu Glu Glu
                420                 425                 430
```

-continued

```
aga gaa aga gca act gag gaa aaa gaa tca aat gat tta tta tta atc      2064
Arg Glu Arg Ala Thr Glu Glu Lys Glu Ser Asn Asp Leu Leu Leu Ile
            435                 440                 445

cgg aag aat aga atg gca ctt ttt caa cat ttg act tgt gta att cca      2112
Arg Lys Asn Arg Met Ala Leu Phe Gln His Leu Thr Cys Val Ile Pro
        450                 455                 460

atc ctg gat agt cta cta act gcc gga att att aat gaa caa gaa cat      2160
Ile Leu Asp Ser Leu Leu Thr Ala Gly Ile Ile Asn Glu Gln Glu His
    465                 470                 475

gat gtt att aaa cag aag aca cag acg tct tta caa gca aga gaa ctg      2208
Asp Val Ile Lys Gln Lys Thr Gln Thr Ser Leu Gln Ala Arg Glu Leu
480                 485                 490                 495

att gat acg att tta gta aaa gga aat att gca gcc act gta ttc aga      2256
Ile Asp Thr Ile Leu Val Lys Gly Asn Ile Ala Ala Thr Val Phe Arg
                500                 505                 510

aac tct ctg caa gaa gct gaa gct gtg tta tat gag cat tta ttt gtg      2304
Asn Ser Leu Gln Glu Ala Glu Ala Val Leu Tyr Glu His Leu Phe Val
            515                 520                 525

caa cag gac ata aaa tat att ccc aca gaa gat gtt tca gat cta cca      2352
Gln Gln Asp Ile Lys Tyr Ile Pro Thr Glu Asp Val Ser Asp Leu Pro
        530                 535                 540

gtg gaa gaa caa ttg cgg aga cta caa gaa gaa aga aca tgt aaa gtg      2400
Val Glu Glu Gln Leu Arg Arg Leu Gln Glu Glu Arg Thr Cys Lys Val
    545                 550                 555

tgt atg gac aaa gaa gtg tcc ata gtg ttt att cct tgt ggt cat cta      2448
Cys Met Asp Lys Glu Val Ser Ile Val Phe Ile Pro Cys Gly His Leu
560                 565                 570                 575

gta gta tgc aaa gat tgt gct cct tct tta aga aag tgt cct att tgt      2496
Val Val Cys Lys Asp Cys Ala Pro Ser Leu Arg Lys Cys Pro Ile Cys
                580                 585                 590

agg agt aca atc aag ggt aca gtt cgt aca ttt ctt tca tga              2538
Arg Ser Thr Ile Lys Gly Thr Val Arg Thr Phe Leu Ser  *
            595                 600

agaagaacca aaacatcatc taaactttag aattaattta ttaaatgtat tataacttta   2598

actttcatcc taatttggtt tccttaaaat ttttatttat ttacaactca acaaacattg   2658

ttttgtgtaa catatttaat atatgtatct aaaccatatg aacatatatt ttttagaaac   2718

taagagaatg ataggctttt gttcttatga acgaaaaaga ggtagcacta caaacacaat   2778

attcaatcaa aatttcagca ttattgaaat tgtaagtgaa gtaaaactta agatatttga   2838

gttaaccttt aagaatttta aatattttgg cattgtacta ataccgggaa catgaagcca   2898

ggtgtggtgg tatgtgcctg tagtcccagg ctgaggcaag agaattactt gagcccagga   2958

gtttgaatcc atcctgggca gcatactgag accctgcctt taaaaacaaa cagaacaaaa   3018

acaaaacacc agggacacat ttctctgtct tttttgatca gtgtcctata catcgaaggt   3078

gtgcatatat gttgaatgac attttaggga catggtgttt ttataaagaa ttctgtgaga   3138

aaaaatttaa taaaaccccc caaatt                                        3164


<210> SEQ ID NO 6
<211> LENGTH: 604
<212> TYPE: PRT
<213> ORGANISM: Homo sapiens

<400> SEQUENCE: 6

Met Asn Ile Val Glu Asn Ser Ile Phe Leu Ser Asn Leu Met Lys Ser
 1               5                  10                  15

Ala Asn Thr Phe Glu Leu Lys Tyr Asp Leu Ser Cys Glu Leu Tyr Arg
```

-continued

```
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
    290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Phe Glu Pro Gly Glu
        355                 360                 365

Asp His Ser Glu Asp Ala Ile Met Met Asn Thr Pro Val Ile Asn Ala
    370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
        435                 440                 445
```

-continued

```
Lys Asn Arg Met Ala Leu Phe Gln His Leu Thr Cys Val Ile Pro Ile
    450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
        515                 520                 525

Gln Asp Ile Lys Tyr Ile Pro Thr Glu Asp Val Ser Asp Leu Pro Val
    530                 535                 540

Glu Glu Gln Leu Arg Arg Leu Gln Glu Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
        595                 600


<210> SEQ ID NO 7
<211> LENGTH: 2585
<212> TYPE: DNA
<213> ORGANISM: Homo sapiens
<220> FEATURE:
<221> NAME/KEY: CDS
<222> LOCATION: (201)...(2546)

<400> SEQUENCE: 7

ggggcagcag cgttggcccg gccccgggag cggagagcga ggggaggcgg agacggagga      60

aggtctgagg agcagcttca gtccccgccg agccgccacc gcaggtcgag gacggtcgga     120

ctcccgcggc gggaggagcc tgttcccctg agggtatttg aagtatacca tacaactgtt     180

ttgaaaatcc agcgtggaca atg gct act caa gct gat ttg atg gag ttg gac     233
                      Met Ala Thr Gln Ala Asp Leu Met Glu Leu Asp
                      1               5                   10

atg gcc atg gaa cca gac aga aaa gcg gct gtt agt cac tgg cag caa       281
Met Ala Met Glu Pro Asp Arg Lys Ala Ala Val Ser His Trp Gln Gln
            15                  20                  25

cag tct tac ctg gac tct gga atc cat tct ggt gcc act acc aca gct       329
Gln Ser Tyr Leu Asp Ser Gly Ile His Ser Gly Ala Thr Thr Thr Ala
        30                  35                  40

cct tct ctg agt ggt aaa ggc aat cct gag gaa gag gat gtg gat acc       377
Pro Ser Leu Ser Gly Lys Gly Asn Pro Glu Glu Glu Asp Val Asp Thr
    45                  50                  55

tcc caa gtc ctg tat gag tgg gaa cag gga ttt tct cag tcc ttc act       425
Ser Gln Val Leu Tyr Glu Trp Glu Gln Gly Phe Ser Gln Ser Phe Thr
 60                  65                  70                  75

caa gaa caa gta gct gat att gat gga cag tat gca atg act cga gct       473
Gln Glu Gln Val Ala Asp Ile Asp Gly Gln Tyr Ala Met Thr Arg Ala
                 80                  85                  90

cag agg gta cga gct gct atg ttc cct gag aca tta gat gag ggc atg       521
Gln Arg Val Arg Ala Ala Met Phe Pro Glu Thr Leu Asp Glu Gly Met
            95                 100                 105

cag atc cca tct aca cag ttt gat gct gct cat ccc act aat gtc cag       569
Gln Ile Pro Ser Thr Gln Phe Asp Ala Ala His Pro Thr Asn Val Gln
        110                 115                 120
```

-continued

```
cgt ttg gct gaa cca tca cag atg ctg aaa cat gca gtt gta aac ttg      617
Arg Leu Ala Glu Pro Ser Gln Met Leu Lys His Ala Val Val Asn Leu
    125                 130                 135

att aac tat caa gat gat gca gaa ctt gcc aca cgt gca atc cct gaa      665
Ile Asn Tyr Gln Asp Asp Ala Glu Leu Ala Thr Arg Ala Ile Pro Glu
140                 145                 150                 155

ctg aca aaa ctg cta aat gac gag gac cag gtg gtg gtt aat aag gct      713
Leu Thr Lys Leu Leu Asn Asp Glu Asp Gln Val Val Val Asn Lys Ala
                160                 165                 170

gca gtt atg gtc cat cag ctt tct aaa aag gaa gct tcc aga cac gct      761
Ala Val Met Val His Gln Leu Ser Lys Lys Glu Ala Ser Arg His Ala
            175                 180                 185

atc atg cgt tct cct cag atg gtg tct gct att gta cgt acc atg cag      809
Ile Met Arg Ser Pro Gln Met Val Ser Ala Ile Val Arg Thr Met Gln
        190                 195                 200

aat aca aat gat gta gaa aca gct cgt tgt acc gct ggg acc ttg cat      857
Asn Thr Asn Asp Val Glu Thr Ala Arg Cys Thr Ala Gly Thr Leu His
    205                 210                 215

aac ctt tcc cat cat cgt gag ggc tta ctg gcc atc ttt aag tct gga      905
Asn Leu Ser His His Arg Glu Gly Leu Leu Ala Ile Phe Lys Ser Gly
220                 225                 230                 235

ggc att cct gcc ctg gtg aaa atg ctt ggt tca cca gtg gat tct gtg      953
Gly Ile Pro Ala Leu Val Lys Met Leu Gly Ser Pro Val Asp Ser Val
                240                 245                 250

ttg ttt tat gcc att aca act ctc cac aac ctt tta tta cat caa gaa     1001
Leu Phe Tyr Ala Ile Thr Thr Leu His Asn Leu Leu Leu His Gln Glu
            255                 260                 265

gga gct aaa atg gca gtg cgt tta gct ggt ggg ctg cag aaa atg gtt     1049
Gly Ala Lys Met Ala Val Arg Leu Ala Gly Gly Leu Gln Lys Met Val
        270                 275                 280

gcc ttg ctc aac aaa aca aat gtt aaa ttc ttg gct att acg aca gac     1097
Ala Leu Leu Asn Lys Thr Asn Val Lys Phe Leu Ala Ile Thr Thr Asp
    285                 290                 295

tgc ctt caa att tta gct tat ggc aac caa gaa agc aag ctc atc ata     1145
Cys Leu Gln Ile Leu Ala Tyr Gly Asn Gln Glu Ser Lys Leu Ile Ile
300                 305                 310                 315

ctg gct agt ggt gga ccc caa gct tta gta aat ata atg agg acc tat     1193
Leu Ala Ser Gly Gly Pro Gln Ala Leu Val Asn Ile Met Arg Thr Tyr
                320                 325                 330

act tac gaa aaa cta ctg tgg acc aca agc aga gtg ctg aag gtg cta     1241
Thr Tyr Glu Lys Leu Leu Trp Thr Thr Ser Arg Val Leu Lys Val Leu
            335                 340                 345

tct gtc tgc tct agt aat aag ccg gct att gta gaa gct ggt gga atg     1289
Ser Val Cys Ser Ser Asn Lys Pro Ala Ile Val Glu Ala Gly Gly Met
        350                 355                 360

caa gct tta gga ctt cac ctg aca gat cca agt caa cgt ctt gtt cag     1337
Gln Ala Leu Gly Leu His Leu Thr Asp Pro Ser Gln Arg Leu Val Gln
    365                 370                 375

aac tgt ctt tgg act ctc agg aat ctt tca gat gct gca act aaa cag     1385
Asn Cys Leu Trp Thr Leu Arg Asn Leu Ser Asp Ala Ala Thr Lys Gln
380                 385                 390                 395

gaa ggg atg gaa ggt ctc ctt ggg act ctt gtt cag ctt ctg ggt tca     1433
Glu Gly Met Glu Gly Leu Leu Gly Thr Leu Val Gln Leu Leu Gly Ser
                400                 405                 410

gat gat ata aat gtg gtc acc tgt gca gct gga att ctt tct aac ctc     1481
Asp Asp Ile Asn Val Val Thr Cys Ala Ala Gly Ile Leu Ser Asn Leu
            415                 420                 425

act tgc aat aat tat aag aac aag atg atg gtc tgc caa gtg ggt ggt     1529
Thr Cys Asn Asn Tyr Lys Asn Lys Met Met Val Cys Gln Val Gly Gly
```

-continued

```
        430                 435                 440

ata gag gct ctt gtg cgt act gtc ctt cgg gct ggt gac agg gaa gac     1577
Ile Glu Ala Leu Val Arg Thr Val Leu Arg Ala Gly Asp Arg Glu Asp
    445                 450                 455

atc act gag cct gcc atc tgt gct ctt cgt cat ctg acc agc cga cac     1625
Ile Thr Glu Pro Ala Ile Cys Ala Leu Arg His Leu Thr Ser Arg His
460                 465                 470                 475

caa gaa gca gag atg gcc cag aat gca gtt cgc ctt cac tat gga cta     1673
Gln Glu Ala Glu Met Ala Gln Asn Ala Val Arg Leu His Tyr Gly Leu
                480                 485                 490

cca gtt gtg gtt aag ctc tta cac cca cca tcc cac tgg cct ctg ata     1721
Pro Val Val Val Lys Leu Leu His Pro Pro Ser His Trp Pro Leu Ile
            495                 500                 505

aag gct act gtt gga ttg att cga aat ctt gcc ctt tgt ccc gca aat     1769
Lys Ala Thr Val Gly Leu Ile Arg Asn Leu Ala Leu Cys Pro Ala Asn
        510                 515                 520

cat gca cct ttg cgt gag cag ggt gcc att cca cga cta gtt cag ttg     1817
His Ala Pro Leu Arg Glu Gln Gly Ala Ile Pro Arg Leu Val Gln Leu
    525                 530                 535

ctt gtt cgt gca cat cag gat acc cag cgc cgt acg tcc atg ggt ggg     1865
Leu Val Arg Ala His Gln Asp Thr Gln Arg Arg Thr Ser Met Gly Gly
540                 545                 550                 555

aca cag cag caa ttt gtg gag ggg gtc cgc atg gaa gaa ata gtt gaa     1913
Thr Gln Gln Gln Phe Val Glu Gly Val Arg Met Glu Glu Ile Val Glu
                560                 565                 570

ggt tgt acc gga gcc ctt cac atc cta gct cgg gat gtt cac aac cga     1961
Gly Cys Thr Gly Ala Leu His Ile Leu Ala Arg Asp Val His Asn Arg
            575                 580                 585

att gtt atc aga gga cta aat acc att cca ttg ttt gtg cag ctg ctt     2009
Ile Val Ile Arg Gly Leu Asn Thr Ile Pro Leu Phe Val Gln Leu Leu
        590                 595                 600

tat tct ccc att gaa aac atc caa aga gta gct gca ggg gtc ctc tgt     2057
Tyr Ser Pro Ile Glu Asn Ile Gln Arg Val Ala Ala Gly Val Leu Cys
    605                 610                 615

gaa ctt gct cag gac aag gaa gct gca gaa gct att gaa gct gag gga     2105
Glu Leu Ala Gln Asp Lys Glu Ala Ala Glu Ala Ile Glu Ala Glu Gly
620                 625                 630                 635

gcc aca gct cct ctg aca gag tta ctt cac tct agg aat gaa ggt gtg     2153
Ala Thr Ala Pro Leu Thr Glu Leu Leu His Ser Arg Asn Glu Gly Val
                640                 645                 650

gcg aca tat gca gct gct gtt ttg ttc cga atg tct gag gac aag cca     2201
Ala Thr Tyr Ala Ala Ala Val Leu Phe Arg Met Ser Glu Asp Lys Pro
            655                 660                 665

caa gat tac aag aaa cgg ctt tca gtt gag ctg acc agc tct ctc ttc     2249
Gln Asp Tyr Lys Lys Arg Leu Ser Val Glu Leu Thr Ser Ser Leu Phe
        670                 675                 680

aga aca gag cca atg gct tgg aat gag act gct gat ctt gga ctt gat     2297
Arg Thr Glu Pro Met Ala Trp Asn Glu Thr Ala Asp Leu Gly Leu Asp
    685                 690                 695

att ggt gcc cag gga gaa ccc ctt gga tat cgc cag gat gat cct agc     2345
Ile Gly Ala Gln Gly Glu Pro Leu Gly Tyr Arg Gln Asp Asp Pro Ser
700                 705                 710                 715

tat cgt tct ttt cac tct ggt gga tat ggc cag gat gcc ttg ggt atg     2393
Tyr Arg Ser Phe His Ser Gly Gly Tyr Gly Gln Asp Ala Leu Gly Met
                720                 725                 730

gac ccc atg atg gaa cat gag atg ggt ggc cac cac cct ggt gct gac     2441
Asp Pro Met Met Glu His Glu Met Gly Gly His His Pro Gly Ala Asp
            735                 740                 745

tat cca gtt gat ggg ctg cca gat ctg ggg cat gcc cag gac ctc atg     2489
```

-continued

```
Tyr Pro Val Asp Gly Leu Pro Asp Leu Gly His Ala Gln Asp Leu Met
        750                 755                 760

gat ggg ctg cct cca ggt gac agc aat cag ctg gcc tgg ttt gat act     2537
Asp Gly Leu Pro Pro Gly Asp Ser Asn Gln Leu Ala Trp Phe Asp Thr
    765                 770                 775

gac ctg taa atcatccttt aggagtaaca atacaaatgg attttgccc              2585
Asp Leu  *
780
```

<210> SEQ ID NO 8
<211> LENGTH: 781
<212> TYPE: PRT
<213> ORGANISM: Homo sapiens

<400> SEQUENCE: 8

```
Met Ala Thr Gln Ala Asp Leu Met Glu Leu Asp Met Ala Met Glu Pro
 1               5                  10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320
```

-continued

```
Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
```

-continued

```
        740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780


<210> SEQ ID NO 9
<211> LENGTH: 7042
<212> TYPE: DNA
<213> ORGANISM: Homo sapiens
<220> FEATURE:
<221> NAME/KEY: CDS
<222> LOCATION: (578)...(4162)

<400> SEQUENCE: 9

aagaagaggt agcgagtgga cgtgactgct ctatcccggg caaaagggat agaaccagag     60

gtggggagtc tgggcagtcg gcgacccgcg aagacttgag gtgccgcagc ggcatccgga    120

gtagcgccgg gctccctccg gggtgcagcc gccgtcgggg gaagggcgcc acaggccggg    180

aagacctcct ccctttgtgt ccagtagtgg ggtccaccgg agggcggccc gtgggccggg    240

cctcaccgcg gcgctccggg actgtggggt caggctgcgt tgggtggacg cccacctcgc    300

caaccttcgg aggtccctgg gggtcttcgt gcgccccggg gctgcagaga tccaggggag    360

gcgcctgtga ggcccggacc tgccccgggg cgaagggtat gtggcgagac agagccctgc    420

acccctaatt cccggtggaa aactcctgtt gccgtttccc tccaccggcc tggagtctcc    480

cagtcttgtc ccggcagtgc cgccctcccc actaagacct aggcgcaaag gcttggctca    540

tggttgacag ctcagagaga gaaagatctg agggaag atg gat gca aaa gct cga     595
                                         Met Asp Ala Lys Ala Arg
                                          1               5

aat tgt ttg ctt caa cat aga gaa gct ctg gaa aag gac atc aag aca      643
Asn Cys Leu Leu Gln His Arg Glu Ala Leu Glu Lys Asp Ile Lys Thr
            10                  15                  20

tcc tac atc atg gat cac atg att agt gat gga ttt tta aca ata tca      691
Ser Tyr Ile Met Asp His Met Ile Ser Asp Gly Phe Leu Thr Ile Ser
        25                  30                  35

gaa gag gaa aaa gta aga aat gag ccc act caa cag caa aga gca gct      739
Glu Glu Glu Lys Val Arg Asn Glu Pro Thr Gln Gln Gln Arg Ala Ala
    40                  45                  50

atg ctg att aaa atg ata ctt aaa aaa gat aat gat tcc tac gta tca      787
Met Leu Ile Lys Met Ile Leu Lys Lys Asp Asn Asp Ser Tyr Val Ser
 55                  60                  65                  70

ttc tac aat gct cta cta cat gaa gga tat aaa gat ctt gct gcc ctt      835
Phe Tyr Asn Ala Leu Leu His Glu Gly Tyr Lys Asp Leu Ala Ala Leu
                75                  80                  85

ctc cat gat ggc att cct gtt gtc tct tct tcc agt gta agg aca gtc      883
Leu His Asp Gly Ile Pro Val Val Ser Ser Ser Ser Val Arg Thr Val
            90                  95                 100

ctg tgt gaa ggt gga gta cca cag agg cca gtt gtt ttt gtc aca agg      931
Leu Cys Glu Gly Gly Val Pro Gln Arg Pro Val Val Phe Val Thr Arg
        105                 110                 115

aag aag ctg gtg aat gca att cag cag aag ctc tcc aaa ttg aaa ggt      979
Lys Lys Leu Val Asn Ala Ile Gln Gln Lys Leu Ser Lys Leu Lys Gly
    120                 125                 130

gaa cca gga tgg gtc acc ata cat gga atg gca ggc tgt ggg aag tct     1027
Glu Pro Gly Trp Val Thr Ile His Gly Met Ala Gly Cys Gly Lys Ser
135                 140                 145                 150

gta tta gct gca gaa gct gtt aga gat cat tcc ctt tta gaa ggt tgt     1075
Val Leu Ala Ala Glu Ala Val Arg Asp His Ser Leu Leu Glu Gly Cys
```

-continued

```
                155                 160                 165

ttc cca ggg gga gtg cat tgg gtt tca gtt ggg aaa caa gac aaa tct     1123
Phe Pro Gly Gly Val His Trp Val Ser Val Gly Lys Gln Asp Lys Ser
            170                 175                 180

ggg ctt ctg atg aaa ctg cag aat ctt tgc aca cgg ttg gat cag gat     1171
Gly Leu Leu Met Lys Leu Gln Asn Leu Cys Thr Arg Leu Asp Gln Asp
        185                 190                 195

gag agt ttt tcc cag agg ctt cca ctt aat att gaa gag gct aaa gac     1219
Glu Ser Phe Ser Gln Arg Leu Pro Leu Asn Ile Glu Glu Ala Lys Asp
    200                 205                 210

cgt ctc cgc att ctg atg ctt cgc aaa cac cca agg tct ctc ttg atc     1267
Arg Leu Arg Ile Leu Met Leu Arg Lys His Pro Arg Ser Leu Leu Ile
215                 220                 225                 230

ttg gat gat gtt tgg gac tct tgg gtg ttg aaa gct ttt gac agt cag     1315
Leu Asp Asp Val Trp Asp Ser Trp Val Leu Lys Ala Phe Asp Ser Gln
                235                 240                 245

tgt cag att ctt ctt aca acc aga gac aag agt gtt aca gat tca gta     1363
Cys Gln Ile Leu Leu Thr Thr Arg Asp Lys Ser Val Thr Asp Ser Val
            250                 255                 260

atg ggt cct aaa tat gta gtc cct gtg gag agt tcc tta gga aag gaa     1411
Met Gly Pro Lys Tyr Val Val Pro Val Glu Ser Ser Leu Gly Lys Glu
        265                 270                 275

aaa gga ctt gaa att tta tcc ctt ttt gtt aat atg aag aag gca gat     1459
Lys Gly Leu Glu Ile Leu Ser Leu Phe Val Asn Met Lys Lys Ala Asp
    280                 285                 290

ttg cca gaa caa gct cat agt att ata aaa gaa tgt aaa ggc tct ccc     1507
Leu Pro Glu Gln Ala His Ser Ile Ile Lys Glu Cys Lys Gly Ser Pro
295                 300                 305                 310

ctt gta gta tct tta att ggt gca ctt tta cgt gat ttt ccc aat cgc     1555
Leu Val Val Ser Leu Ile Gly Ala Leu Leu Arg Asp Phe Pro Asn Arg
                315                 320                 325

tgg gag tac tac ctc aaa cag ctt cag aat aag cag ttt aag aga ata     1603
Trp Glu Tyr Tyr Leu Lys Gln Leu Gln Asn Lys Gln Phe Lys Arg Ile
            330                 335                 340

agg aaa tct tcg tct tat gat tat gag gct cta gat gaa gcc atg tct     1651
Arg Lys Ser Ser Ser Tyr Asp Tyr Glu Ala Leu Asp Glu Ala Met Ser
        345                 350                 355

ata agt gtt gaa atg ctc aga gaa gac atc aaa gat tat tac aca gat     1699
Ile Ser Val Glu Met Leu Arg Glu Asp Ile Lys Asp Tyr Tyr Thr Asp
    360                 365                 370

ctt tcc atc ctt cag aag gac gtt aag gtg cct aca aag gtg tta tgt     1747
Leu Ser Ile Leu Gln Lys Asp Val Lys Val Pro Thr Lys Val Leu Cys
375                 380                 385                 390

att ctc tgg gac atg gaa act gaa gaa gtt gaa gac ata ctg cag gag     1795
Ile Leu Trp Asp Met Glu Thr Glu Glu Val Glu Asp Ile Leu Gln Glu
                395                 400                 405

ttt gta aat aag tct ctt tta ttc tgt gat cgg aat gga aag tcg ttt     1843
Phe Val Asn Lys Ser Leu Leu Phe Cys Asp Arg Asn Gly Lys Ser Phe
            410                 415                 420

cgt tat tat tta cat gat ctt caa gta gat ttt ctt aca gag aag aat     1891
Arg Tyr Tyr Leu His Asp Leu Gln Val Asp Phe Leu Thr Glu Lys Asn
        425                 430                 435

tgc agc cag ctt cag gat cta cat aag aag ata atc act cag ttt cag     1939
Cys Ser Gln Leu Gln Asp Leu His Lys Lys Ile Ile Thr Gln Phe Gln
    440                 445                 450

aga tat cac cag ccg cat act ctt tca cca gat cag gaa gac tgt atg     1987
Arg Tyr His Gln Pro His Thr Leu Ser Pro Asp Gln Glu Asp Cys Met
455                 460                 465                 470

tat tgg tac aac ttt ctg gcc tat cac atg gcc agt gcc aag atg cac     2035
```

-continued

```
Tyr Trp Tyr Asn Phe Leu Ala Tyr His Met Ala Ser Ala Lys Met His
                475                 480                 485

aag gaa ctt tgt gct tta atg ttt tcc ctg gat tgg att aaa gca aaa      2083
Lys Glu Leu Cys Ala Leu Met Phe Ser Leu Asp Trp Ile Lys Ala Lys
            490                 495                 500

aca gaa ctt gta ggc cct gct cat ctg att cat gaa ttt gtg gaa tac      2131
Thr Glu Leu Val Gly Pro Ala His Leu Ile His Glu Phe Val Glu Tyr
        505                 510                 515

aga cat ata cta gat gaa aag gat tgt gca gtc agt gag aat ttt cag      2179
Arg His Ile Leu Asp Glu Lys Asp Cys Ala Val Ser Glu Asn Phe Gln
    520                 525                 530

gag ttt tta tct tta aat gga cac ctt ctt gga cga cag cca ttt cct      2227
Glu Phe Leu Ser Leu Asn Gly His Leu Leu Gly Arg Gln Pro Phe Pro
535                 540                 545                 550

aat att gta caa ctg ggt ctc tgt gag ccg gaa act tca gaa gtt tat      2275
Asn Ile Val Gln Leu Gly Leu Cys Glu Pro Glu Thr Ser Glu Val Tyr
                555                 560                 565

cag caa gct aag ctg cag gcc aag cag gag gtc gat aat gga atg ctt      2323
Gln Gln Ala Lys Leu Gln Ala Lys Gln Glu Val Asp Asn Gly Met Leu
            570                 575                 580

tac ctg gaa tgg ata aac aaa aaa aac atc acg aat ctt tcc cgc tta      2371
Tyr Leu Glu Trp Ile Asn Lys Lys Asn Ile Thr Asn Leu Ser Arg Leu
        585                 590                 595

gtt gtc cgc ccc cac aca gat gct gtt tac cat gcc tgc ttt tct gag      2419
Val Val Arg Pro His Thr Asp Ala Val Tyr His Ala Cys Phe Ser Glu
    600                 605                 610

gat ggt cag aga ata gct tct tgt gga gct gat aaa acc tta cag gtg      2467
Asp Gly Gln Arg Ile Ala Ser Cys Gly Ala Asp Lys Thr Leu Gln Val
615                 620                 625                 630

ttc aaa gct gaa aca gga gag aaa ctt cta gaa atc aag gct cat gag      2515
Phe Lys Ala Glu Thr Gly Glu Lys Leu Leu Glu Ile Lys Ala His Glu
                635                 640                 645

gat gaa gtg ctt tgt tgt gca ttc tct aca gat gac aga ttt ata gca      2563
Asp Glu Val Leu Cys Cys Ala Phe Ser Thr Asp Asp Arg Phe Ile Ala
            650                 655                 660

acc tgc tca gtg gat aaa aaa gtg aag att tgg aat tct atg act ggg      2611
Thr Cys Ser Val Asp Lys Lys Val Lys Ile Trp Asn Ser Met Thr Gly
        665                 670                 675

gaa cta gta cac acc tat gat gag cac tca gag caa gtc aat tgc tgc      2659
Glu Leu Val His Thr Tyr Asp Glu His Ser Glu Gln Val Asn Cys Cys
    680                 685                 690

cat ttc acc aac agt agt cat cat ctt ctc tta gcc act ggg tca agt      2707
His Phe Thr Asn Ser Ser His His Leu Leu Leu Ala Thr Gly Ser Ser
695                 700                 705                 710

gac tgc ttc ctc aaa ctt tgg gat ttg aat caa aaa gaa tgt cga aat      2755
Asp Cys Phe Leu Lys Leu Trp Asp Leu Asn Gln Lys Glu Cys Arg Asn
                715                 720                 725

acc atg ttt ggt cat aca aat tca gtc aat cac tgc aga ttt tca cca      2803
Thr Met Phe Gly His Thr Asn Ser Val Asn His Cys Arg Phe Ser Pro
            730                 735                 740

gat gat aag ctt ttg gct agt tgt tca gct gat gga acc tta aag ctt      2851
Asp Asp Lys Leu Leu Ala Ser Cys Ser Ala Asp Gly Thr Leu Lys Leu
        745                 750                 755

tgg gat gcg aca tca gca aat gag agg aaa agc att aat gtg aaa cag      2899
Trp Asp Ala Thr Ser Ala Asn Glu Arg Lys Ser Ile Asn Val Lys Gln
    760                 765                 770

ttc ttc cta aat ttg gag gac cct caa gag gat atg gaa gtg ata gtg      2947
Phe Phe Leu Asn Leu Glu Asp Pro Gln Glu Asp Met Glu Val Ile Val
775                 780                 785                 790
```

-continued

```
aag tgt tgt tcg tgg tct gct gat ggt gca agg ata atg gtg gca gca      2995
Lys Cys Cys Ser Trp Ser Ala Asp Gly Ala Arg Ile Met Val Ala Ala
            795                 800                 805

aaa aat aaa atc ttt ttg tgg aat aca gac tca cgt tca aag gtg gct      3043
Lys Asn Lys Ile Phe Leu Trp Asn Thr Asp Ser Arg Ser Lys Val Ala
        810                 815                 820

gat tgc aga gga cat tta agt tgg gtt cat ggt gtg atg ttt tct cct      3091
Asp Cys Arg Gly His Leu Ser Trp Val His Gly Val Met Phe Ser Pro
    825                 830                 835

gat gga tca tca ttt ttg aca tct tct gat gac cag aca atc agg ctc      3139
Asp Gly Ser Ser Phe Leu Thr Ser Ser Asp Asp Gln Thr Ile Arg Leu
840                 845                 850

tgg gag aca aag aaa gta tgt aag aac tct gct gta atg tta aag caa      3187
Trp Glu Thr Lys Lys Val Cys Lys Asn Ser Ala Val Met Leu Lys Gln
855                 860                 865                 870

gaa gta gat gtt gtg ttt caa gaa aat gaa gtg atg gtc ctt gca gtt      3235
Glu Val Asp Val Val Phe Gln Glu Asn Glu Val Met Val Leu Ala Val
                875                 880                 885

gac cat ata aga cgt ctg caa ctc att aat gga aga aca ggt cag att      3283
Asp His Ile Arg Arg Leu Gln Leu Ile Asn Gly Arg Thr Gly Gln Ile
            890                 895                 900

gat tat ctg act gaa gct caa gtt agc tgc tgt tgc tta agt cca cat      3331
Asp Tyr Leu Thr Glu Ala Gln Val Ser Cys Cys Cys Leu Ser Pro His
        905                 910                 915

ctt cag tac att gca ttt gga gat gaa aat gga gcc att gag att tta      3379
Leu Gln Tyr Ile Ala Phe Gly Asp Glu Asn Gly Ala Ile Glu Ile Leu
    920                 925                 930

gaa ctt gta aac aat aga atc ttc cag tcc agg ttt cag cac aag aaa      3427
Glu Leu Val Asn Asn Arg Ile Phe Gln Ser Arg Phe Gln His Lys Lys
935                 940                 945                 950

act gta tgg cac atc cag ttc aca gcc gat gag aag act ctt att tca      3475
Thr Val Trp His Ile Gln Phe Thr Ala Asp Glu Lys Thr Leu Ile Ser
                955                 960                 965

agt tct gat gat gct gaa att cag gta tgg aat tgg caa ttg gac aaa      3523
Ser Ser Asp Asp Ala Glu Ile Gln Val Trp Asn Trp Gln Leu Asp Lys
            970                 975                 980

tgt atc ttt cta cga ggc cat cag gaa aca gtg aaa gac ttt aga ctc      3571
Cys Ile Phe Leu Arg Gly His Gln Glu Thr Val Lys Asp Phe Arg Leu
        985                 990                 995

ttg aaa aat tca aga ctg ctt tct tgg tca ttt gat gga aca gtg aag      3619
Leu Lys Asn Ser Arg Leu Leu Ser Trp Ser Phe Asp Gly Thr Val Lys
    1000                1005                1010

gta tgg aat att att act gga aat aaa gaa aaa gac ttt gtc tgt cac      3667
Val Trp Asn Ile Ile Thr Gly Asn Lys Glu Lys Asp Phe Val Cys His
1015                1020                1025                1030

cag ggt aca gta ctt tct tgt gac att tct cac gat gct acc aag ttt      3715
Gln Gly Thr Val Leu Ser Cys Asp Ile Ser His Asp Ala Thr Lys Phe
                1035                1040                1045

tca tct acc tct gct gac aag act gca aag atc tgg agt ttt gat ctc      3763
Ser Ser Thr Ser Ala Asp Lys Thr Ala Lys Ile Trp Ser Phe Asp Leu
            1050                1055                1060

ctt ttg cca ctt cat gaa ttg agg ggc cac aac ggc tgt gtg cgc tgc      3811
Leu Leu Pro Leu His Glu Leu Arg Gly His Asn Gly Cys Val Arg Cys
        1065                1070                1075

tct gcc ttc tct gtg gac agt acc ctg ctg gca acg gga gat gac aat      3859
Ser Ala Phe Ser Val Asp Ser Thr Leu Leu Ala Thr Gly Asp Asp Asn
    1080                1085                1090

gga gaa atc agg ata tgg aat gtc tca aac ggt gag ctt ctt cat ttg      3907
Gly Glu Ile Arg Ile Trp Asn Val Ser Asn Gly Glu Leu Leu His Leu
1095                1100                1105                1110
```

-continued

```
tgt gct ccg ctt tca gaa gaa gga gct gct acc cat gga ggc tgg gtg     3955
Cys Ala Pro Leu Ser Glu Glu Gly Ala Ala Thr His Gly Gly Trp Val
                1115                1120                1125

act gac ctt tgc ttt tct cca gat ggc aaa atg ctt atc tct gct gga     4003
Thr Asp Leu Cys Phe Ser Pro Asp Gly Lys Met Leu Ile Ser Ala Gly
            1130                1135                1140

gga tat att aag tgg tgg aac gtt gtc act ggg gaa tcc tca cag acc     4051
Gly Tyr Ile Lys Trp Trp Asn Val Val Thr Gly Glu Ser Ser Gln Thr
        1145                1150                1155

ttc tac aca aat gga acc aat ctt aag aaa ata cac gtg tcc cct gac     4099
Phe Tyr Thr Asn Gly Thr Asn Leu Lys Lys Ile His Val Ser Pro Asp
    1160                1165                1170

ttc aaa aca tat gtg act gtg gat aat ctt ggt att tta tat att tta     4147
Phe Lys Thr Tyr Val Thr Val Asp Asn Leu Gly Ile Leu Tyr Ile Leu
1175                1180                1185                1190

cag act tta gaa taa aatagttaag cattaatgta gttgaacttt ttaaattttt     4202
Gln Thr Leu Glu  *

gaattggaaa aaaattctaa tgaaaccctg atatcaactt tttataaagc tcttaattgt   4262

tgtgcagtat tgcattcatt acaaaagtgt ttgtggttgg atgaataata ttaatgtagc   4322

tttttcccaa atgaacatac ctttaatctt gtttttcatg atcatcatta acagtttgtc   4382

cttaggatgc aaatgaaaat gtgaatacat accttgttgt actgttggta aaattctgtc   4442

ttgatgcatt caaaatggtt gacataatta atgagaagaa tttggaagaa attggtattt   4502

taatactgtc tgtatttatt actgttatgc aggctgtgcc tcagggtagc agtggcctgc   4562

tttttgaacc acacttaccc caaggggggtt ttgttctcct aaatacaatc ttagaggttt   4622

tttgcactct ttaaatttgc tttaaaaata ttgtgtctgt gtgcatagtc tgcagcattt   4682

cctttaattg actcaataag tgagtcttgg atttagcagg cccccccacc ttttttttt   4742

gtttttggag acagagtctt gctttgttgc caggctggag tgcagtggcg cgatctcggc   4802

tcaccacaat cgctgcctcc tgggttcaag caattctcct gcctcagcct cccgagtagc   4862

tgggactaca ggtgtgcgca catgccaggc taatttttgt atttttagta gagacggggt   4922

ttcaccatgt tggccgggat ggtctcgatc tcttgacctc atgatctacc cgccttggcc   4982

tcccaaagtg ctgagattac aggcgtgagc caccgtgcct ggccaggccc cttctctttt   5042

aatggagaca gggtcttgca ctatcaccca ggctggagtg cagtggcata atcatacctc   5102

attgcagcct cagactcctg ggttcaagca atcctcctgc ctcagcctcc caagtagctg   5162

agactgcagg cacgagccac cacacccagc taatttttaa gttttcttgt agagacaggg   5222

tctcactatg ttgtctaggc tggtcttgaa ctcttggcct caagtaatcc tcctgcctca   5282

gcctcccaaa gtgttgggat tgcagatatg agccactggc ctggccttca gcagttcttt   5342

ttgtgaagta aaacttgtat gttggaaaga gtagatttta ttggtctacc cttttctcac   5402

tgtagctgct ggcagccctg tgccatatct ggactctagt tgtcagtatc tgagttggac   5462

actattcctg ctccctcttg tttcttacat atcagacttc ttacttgaat gaaacctgat   5522

ctttcctaat cctcactttt ttctttttta aaaagcagtt tctccactgc taaatgttag   5582

tcattgaggt ggggccaatt ttaatcataa gccttaataa gatttttcta agaaatgtga   5642

aatagaacaa ttttcatcta attccattta cttttagatg aatggcattg tgaatgccat   5702

tcttttaatg aatttcaaga gaattctctg gttttctgtg taattccaga tgagtcactg   5762

taactctaga agattaacct tccagccaac ctattttcct ttcccttgtc tctctcatcc   5822

tcttttcctt ccttctttcc tttctcttct tttatctcca aggttaatca ggaaaaatag   5882
```

-continued

```
cttttgacag gggaaaaaac tcaataacta gctatttttg acctcctgat caggaacttt   5942
agttgaagcg taaatctaaa gaaacatttt ctctgaaata tattattaag ggcaatggag   6002
ataaattaat agtagatgtg gttcccagaa aatataatca aaattcaaag attttttttg   6062
tttctgtaac tggaactaaa tcaaatgatt actagtgtta atagtagata acttgttttt   6122
attgttggtg catattagta taactgtggg gtaggtcggg gagagggtaa gggaatagat   6182
cactcagatg tattttagat aagctattta gcctttgatg gaatcataaa tacagtgaat   6242
acaatccttt gcattgttaa ggaggttttt tgtttttaaa tggtgggtca aggagctagt   6302
ttacaggctt actgtgattt aagcaaatgt gaaaagtgaa accttaattt tatcaaaaga   6362
aatttctgta aatggtatgt ctccttagaa tacccaaatc ataattttat ttgtacacac   6422
tgttaggggc tcatctcatg taggcagagt ataaagtatt accttttgga attaaaagcc   6482
actgactgtt ataaagtata acaacacaca tcaggtttta aaaagccttg aatggccctt   6542
gtcttaaaaa gaaattagga gccaggtgcg gtggcacgtg cctgtagtcc cagctccttg   6602
ggaggctgag acaggaggat tccttgagcc ctggagtttg agtccagcct gggtgacata   6662
gcaagaccct gtcttaaaag aaaaatggga agaaagacaa ggtaacatga agaaagaaga   6722
gatacctagt atgatggagc tgcaaatttc atggcagttc atgcagtcgg tcaagaggag   6782
gattttgttt tgtagtttgc agatgagcat ttctaaagca ttttcccttg ctgtattttt   6842
ttgtattata aattacattg gacttcatat atataatttt tttttacatt atatgtctct   6902
tgtatgtttt gaaactcttg tatttatgat atagcttata tgattttttt gccttggtat   6962
acattttaaa atatgaattt aaaaaatttt tgtaaaaata aaattcacaa aattgttttg   7022
aaaaacaaaa aaaaaaaaaa                                               7042
```

<210> SEQ ID NO 10
<211> LENGTH: 1194
<212> TYPE: PRT
<213> ORGANISM: Homo sapiens

<400> SEQUENCE: 10

```
Met Asp Ala Lys Ala Arg Asn Cys Leu Leu Gln His Arg Glu Ala Leu
 1               5                  10                  15

Glu Lys Asp Ile Lys Thr Ser Tyr Ile Met Asp His Met Ile Ser Asp
            20                  25                  30

Gly Phe Leu Thr Ile Ser Glu Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Val Arg Thr Val Leu Cys Glu Gly Gly Val Pro Gln Arg Pro
            100                 105                 110

Val Val Phe Val Thr Arg Lys Lys Leu Val Asn Ala Ile Gln Gln Lys
        115                 120                 125

Leu Ser Lys Leu Lys Gly Glu Pro Gly Trp Val Thr Ile His Gly Met
    130                 135                 140

Ala Gly Cys Gly Lys Ser Val Leu Ala Ala Glu Ala Val Arg Asp His
145                 150                 155                 160
```

-continued

```
Ser Leu Leu Glu Gly Cys Phe Pro Gly Gly Val His Trp Val Ser Val
                165                 170                 175

Gly Lys Gln Asp Lys Ser Gly Leu Leu Met Lys Leu Gln Asn Leu Cys
            180                 185                 190

Thr Arg Leu Asp Gln Asp Glu Ser Phe Ser Gln Arg Leu Pro Leu Asn
        195                 200                 205

Ile Glu Glu Ala Lys Asp Arg Leu Arg Ile Leu Met Leu Arg Lys His
    210                 215                 220

Pro Arg Ser Leu Leu Ile Leu Asp Asp Val Trp Asp Ser Trp Val Leu
225                 230                 235                 240

Lys Ala Phe Asp Ser Gln Cys Gln Ile Leu Leu Thr Thr Arg Asp Lys
                245                 250                 255

Ser Val Thr Asp Ser Val Met Gly Pro Lys Tyr Val Val Pro Val Glu
            260                 265                 270

Ser Ser Leu Gly Lys Glu Lys Gly Leu Glu Ile Leu Ser Leu Phe Val
        275                 280                 285

Asn Met Lys Lys Ala Asp Leu Pro Glu Gln Ala His Ser Ile Ile Lys
    290                 295                 300

Glu Cys Lys Gly Ser Pro Leu Val Val Ser Leu Ile Gly Ala Leu Leu
305                 310                 315                 320

Arg Asp Phe Pro Asn Arg Trp Glu Tyr Tyr Leu Lys Gln Leu Gln Asn
                325                 330                 335

Lys Gln Phe Lys Arg Ile Arg Lys Ser Ser Ser Tyr Asp Tyr Glu Ala
            340                 345                 350

Leu Asp Glu Ala Met Ser Ile Ser Val Glu Met Leu Arg Glu Asp Ile
        355                 360                 365

Lys Asp Tyr Tyr Thr Asp Leu Ser Ile Leu Gln Lys Asp Val Lys Val
    370                 375                 380

Pro Thr Lys Val Leu Cys Ile Leu Trp Asp Met Glu Thr Glu Glu Val
385                 390                 395                 400

Glu Asp Ile Leu Gln Glu Phe Val Asn Lys Ser Leu Leu Phe Cys Asp
                405                 410                 415

Arg Asn Gly Lys Ser Phe Arg Tyr Tyr Leu His Asp Leu Gln Val Asp
            420                 425                 430

Phe Leu Thr Glu Lys Asn Cys Ser Gln Leu Gln Asp Leu His Lys Lys
        435                 440                 445

Ile Ile Thr Gln Phe Gln Arg Tyr His Gln Pro His Thr Leu Ser Pro
    450                 455                 460

Asp Gln Glu Asp Cys Met Tyr Trp Tyr Asn Phe Leu Ala Tyr His Met
465                 470                 475                 480

Ala Ser Ala Lys Met His Lys Glu Leu Cys Ala Leu Met Phe Ser Leu
                485                 490                 495

Asp Trp Ile Lys Ala Lys Thr Glu Leu Val Gly Pro Ala His Leu Ile
            500                 505                 510

His Glu Phe Val Glu Tyr Arg His Ile Leu Asp Glu Lys Asp Cys Ala
        515                 520                 525

Val Ser Glu Asn Phe Gln Glu Phe Leu Ser Leu Asn Gly His Leu Leu
    530                 535                 540

Gly Arg Gln Pro Phe Pro Asn Ile Val Gln Leu Gly Leu Cys Glu Pro
545                 550                 555                 560

Glu Thr Ser Glu Val Tyr Gln Gln Ala Lys Leu Gln Ala Lys Gln Glu
                565                 570                 575

Val Asp Asn Gly Met Leu Tyr Leu Glu Trp Ile Asn Lys Lys Asn Ile
```

-continued

```
            580                 585                 590

Thr Asn Leu Ser Arg Leu Val Val Arg Pro His Thr Asp Ala Val Tyr
        595                 600                 605

His Ala Cys Phe Ser Glu Asp Gly Gln Arg Ile Ala Ser Cys Gly Ala
    610                 615                 620

Asp Lys Thr Leu Gln Val Phe Lys Ala Glu Thr Gly Glu Lys Leu Leu
625                 630                 635                 640

Glu Ile Lys Ala His Glu Asp Glu Val Leu Cys Cys Ala Phe Ser Thr
                645                 650                 655

Asp Asp Arg Phe Ile Ala Thr Cys Ser Val Asp Lys Lys Val Lys Ile
            660                 665                 670

Trp Asn Ser Met Thr Gly Glu Leu Val His Thr Tyr Asp Glu His Ser
        675                 680                 685

Glu Gln Val Asn Cys Cys His Phe Thr Asn Ser Ser His His Leu Leu
    690                 695                 700

Leu Ala Thr Gly Ser Ser Asp Cys Phe Leu Lys Leu Trp Asp Leu Asn
705                 710                 715                 720

Gln Lys Glu Cys Arg Asn Thr Met Phe Gly His Thr Asn Ser Val Asn
                725                 730                 735

His Cys Arg Phe Ser Pro Asp Asp Lys Leu Leu Ala Ser Cys Ser Ala
            740                 745                 750

Asp Gly Thr Leu Lys Leu Trp Asp Ala Thr Ser Ala Asn Glu Arg Lys
        755                 760                 765

Ser Ile Asn Val Lys Gln Phe Phe Leu Asn Leu Glu Asp Pro Gln Glu
    770                 775                 780

Asp Met Glu Val Ile Val Lys Cys Cys Ser Trp Ser Ala Asp Gly Ala
785                 790                 795                 800

Arg Ile Met Val Ala Ala Lys Asn Lys Ile Phe Leu Trp Asn Thr Asp
                805                 810                 815

Ser Arg Ser Lys Val Ala Asp Cys Arg Gly His Leu Ser Trp Val His
            820                 825                 830

Gly Val Met Phe Ser Pro Asp Gly Ser Ser Phe Leu Thr Ser Ser Asp
        835                 840                 845

Asp Gln Thr Ile Arg Leu Trp Glu Thr Lys Lys Val Cys Lys Asn Ser
    850                 855                 860

Ala Val Met Leu Lys Gln Glu Val Asp Val Val Phe Gln Glu Asn Glu
865                 870                 875                 880

Val Met Val Leu Ala Val Asp His Ile Arg Arg Leu Gln Leu Ile Asn
                885                 890                 895

Gly Arg Thr Gly Gln Ile Asp Tyr Leu Thr Glu Ala Gln Val Ser Cys
            900                 905                 910

Cys Cys Leu Ser Pro His Leu Gln Tyr Ile Ala Phe Gly Asp Glu Asn
        915                 920                 925

Gly Ala Ile Glu Ile Leu Glu Leu Val Asn Asn Arg Ile Phe Gln Ser
    930                 935                 940

Arg Phe Gln His Lys Lys Thr Val Trp His Ile Gln Phe Thr Ala Asp
945                 950                 955                 960

Glu Lys Thr Leu Ile Ser Ser Ser Asp Asp Ala Glu Ile Gln Val Trp
                965                 970                 975

Asn Trp Gln Leu Asp Lys Cys Ile Phe Leu Arg Gly His Gln Glu Thr
            980                 985                 990

Val Lys Asp Phe Arg Leu Leu Lys Asn Ser Arg Leu Leu Ser Trp Ser
        995                 1000                1005
```

-continued

```
Phe Asp Gly Thr Val Lys Val Trp Asn Ile Ile Thr Gly Asn Lys Glu
    1010                1015                1020

Lys Asp Phe Val Cys His Gln Gly Thr Val Leu Ser Cys Asp Ile Ser
1025                1030                1035                1040

His Asp Ala Thr Lys Phe Ser Ser Thr Ser Ala Asp Lys Thr Ala Lys
                1045                1050                1055

Ile Trp Ser Phe Asp Leu Leu Leu Pro Leu His Glu Leu Arg Gly His
            1060                1065                1070

Asn Gly Cys Val Arg Cys Ser Ala Phe Ser Val Asp Ser Thr Leu Leu
        1075                1080                1085

Ala Thr Gly Asp Asp Asn Gly Glu Ile Arg Ile Trp Asn Val Ser Asn
    1090                1095                1100

Gly Glu Leu Leu His Leu Cys Ala Pro Leu Ser Glu Glu Gly Ala Ala
1105                1110                1115                1120

Thr His Gly Gly Trp Val Thr Asp Leu Cys Phe Ser Pro Asp Gly Lys
                1125                1130                1135

Met Leu Ile Ser Ala Gly Gly Tyr Ile Lys Trp Trp Asn Val Val Thr
            1140                1145                1150

Gly Glu Ser Ser Gln Thr Phe Tyr Thr Asn Gly Thr Asn Leu Lys Lys
        1155                1160                1165

Ile His Val Ser Pro Asp Phe Lys Thr Tyr Val Thr Val Asp Asn Leu
    1170                1175                1180

Gly Ile Leu Tyr Ile Leu Gln Thr Leu Glu
1185                1190
```

```
<210> SEQ ID NO 11
<211> LENGTH: 5086
<212> TYPE: DNA
<213> ORGANISM: Homo sapiens
<220> FEATURE:
<221> NAME/KEY: CDS
<222> LOCATION: (1459)...(2178)

<400> SEQUENCE: 11

gcgcccgccc ctccgcgccg cctgcccgcc cgcccgccgc gctcccgccc gccgctctcc     60

gtggccccgc cgcgctgccg ccgccgccgc tgccagcgaa ggtgccgggg ctccgggccc    120

tccctgccgg cggccgtcag cgctcggagc gaactgcgcg acgggaggtc cgggaggcga    180

ccgtagtcgc gccgccgcgc aggaccagga ggaggagaaa gggtgcgcag cccggaggcg    240

gggtgcgccg gtggggtgca gcggaagagg gggtccaggg gggagaactt cgtagcagtc    300

atccttttta ggaaaagagg gaaaaaataa aaccctcccc caccacctcc ttctccccac    360

ccctcgccgc accacacaca gcgcgggctt ctagcgctcg gcaccggcgg gccaggcgcg    420

tcctgccttc atttatccag cagcttttcg gaaaatgcat ttgctgttcg gagtttaatc    480

agaagacgat tcctgcctcc gtccccggct ccttcatcgt cccatctccc ctgtctctct    540

cctggggagg cgtgaagcgg tcccgtggat agagattcat gcctgtgtcc gcgcgtgtgt    600

gcgcgcgtat aaattgccga gaaggggaaa acatcacagg acttctgcga ataccggact    660

gaaaattgta attcatctgc cgccgccgct gccaaaaaaa aactcgagct cttgagatct    720

ccggttggga ttcctgcgga ttgacatttc tgtgaagcag aagtctggga atcgatctgg    780

aaatcctcct aatttttact ccctctcccc ccgactcctg attcattggg aagtttcaaa    840

tcagctataa ctggagagtg ctgaagattg atgggatcgt tgccttatgc atttgttttg    900

gttttacaaa aaggaaactt gacagaggat catgctgtac ttaaaaaata caagtaagtc    960
```

```
tcgcacagga aattggttta atgtaacttt caatggaaac ctttgagatt ttttacttaa    1020

agtgcattcg agtaaattta atttccaggc agcttaatac attgttttta gccgtgttac    1080

ttgtagtgtg tatgccctgc tttcactcag tgtgtacagg gaaacgcacc tgatttttta    1140

cttattagtt tgttttttct ttaacctttc agcatcacag aggaagtaga ctgatattaa    1200

caatacttac taataataac gtgcctcatg aaataaagat ccgaaaggaa ttggaataaa    1260

aatttcctgc gtctcatgcc aagagggaaa caccagaatc aagtgttccg cgtgattgaa    1320

gacaccccct cgtccaagaa tgcaaagcac atccaataaa atagctggat tataactcct    1380

cttctttctc tgggggccgt ggggtgggag ctggggcgag aggtgccgtt ggccccgtt     1440
```

| | | | | | | | | | | | |
|---|---|---|---|---|---|---|---|---|---|---|---|
| gcttttcctc tgggaagg atg gcg cac gct ggg aga acg ggg tac gac aac | | | | | | | | | | | 1491 |
| | Met | Ala | His | Ala | Gly | Arg | Thr | Gly | Tyr | Asp | Asn |
| | 1 | | | 5 | | | | | | 10 | |

```
cgg gag ata gtg atg aag tac atc cat tat aag ctg tcg cag agg ggc    1539
Arg Glu Ile Val Met Lys Tyr Ile His Tyr Lys Leu Ser Gln Arg Gly
            15                  20                  25

tac gag tgg gat gcg gga gat gtg ggc gcc gcg ccg ccg ggg gcc gcc    1587
Tyr Glu Trp Asp Ala Gly Asp Val Gly Ala Ala Pro Pro Gly Ala Ala
        30                  35                  40

ccc gca ccg ggc atc ttc tcc tcc cag ccc ggg cac acg ccc cat cca    1635
Pro Ala Pro Gly Ile Phe Ser Ser Gln Pro Gly His Thr Pro His Pro
    45                  50                  55

gcc gca tcc cgc gac ccg gtc gcc agg acc tcg ccg ctg cag acc ccg    1683
Ala Ala Ser Arg Asp Pro Val Ala Arg Thr Ser Pro Leu Gln Thr Pro
60                  65                  70                  75

gct gcc ccc ggc gcc gcc gcg ggg cct gcg ctc agc ccg gtg cca cct    1731
Ala Ala Pro Gly Ala Ala Ala Gly Pro Ala Leu Ser Pro Val Pro Pro
                80                  85                  90

gtg gtc cac ctg gcc ctc cgc caa gcc ggc gac gac ttc tcc cgc cgc    1779
Val Val His Leu Ala Leu Arg Gln Ala Gly Asp Asp Phe Ser Arg Arg
            95                  100                 105

tac cgc ggc gac ttc gcc gag atg tcc agc cag ctg cac ctg acg ccc    1827
Tyr Arg Gly Asp Phe Ala Glu Met Ser Ser Gln Leu His Leu Thr Pro
        110                 115                 120

ttc acc gcg cgg gga cgc ttt gcc acg gtg gtg gag gag ctc ttc agg    1875
Phe Thr Ala Arg Gly Arg Phe Ala Thr Val Val Glu Glu Leu Phe Arg
    125                 130                 135

gac ggg gtg aac tgg ggg agg att gtg gcc ttc ttt gag ttc ggt ggg    1923
Asp Gly Val Asn Trp Gly Arg Ile Val Ala Phe Phe Glu Phe Gly Gly
140                 145                 150                 155

gtc atg tgt gtg gag agc gtc aac cgg gag atg tcg ccc ctg gtg gac    1971
Val Met Cys Val Glu Ser Val Asn Arg Glu Met Ser Pro Leu Val Asp
                160                 165                 170

aac atc gcc ctg tgg atg act gag tac ctg aac cgg cac ctg cac acc    2019
Asn Ile Ala Leu Trp Met Thr Glu Tyr Leu Asn Arg His Leu His Thr
            175                 180                 185

tgg atc cag gat aac gga ggc tgg gat gcc ttt gtg gaa ctg tac ggc    2067
Trp Ile Gln Asp Asn Gly Gly Trp Asp Ala Phe Val Glu Leu Tyr Gly
        190                 195                 200

ccc agc atg cgg cct ctg ttt gat ttc tcc tgg ctg tct ctg aag act    2115
Pro Ser Met Arg Pro Leu Phe Asp Phe Ser Trp Leu Ser Leu Lys Thr
    205                 210                 215

ctg ctc agt ttg gcc ctg gtg gga gct tgc atc acc ctg ggt gcc tat    2163
Leu Leu Ser Leu Ala Leu Val Gly Ala Cys Ile Thr Leu Gly Ala Tyr
220                 225                 230                 235

ctg agc cac aag tga agtcaacatg cctgccccaa acaaatatgc aaaaggttca    2218
Leu Ser His Lys *
```

-continued

```
ctaaagcagt agaaataata tgcattgtca gtgatgtacc atgaaacaaa gctgcaggct   2278
gtttaagaaa aaataacaca catataaaca tcacacacac agacagacac acacacacac   2338
aacaattaac agtcttcagg caaaacgtcg aatcagctat ttactgccaa agggaaatat   2398
catttatttt ttacattatt aagaaaaaag atttatttat ttaagacagt cccatcaaaa   2458
ctccgtcttt ggaaatccga ccactaattg ccaaacaccg cttcgtgtgg ctccacctgg   2518
atgttctgtg cctgtaaaca tagattcgct ttccatgttg ttggccggat caccatctga   2578
agagcagacg gatggaaaaa ggacctgatc attggggaag ctggctttct ggctgctgga   2638
ggctggggag aaggtgttca ttcacttgca tttctttgcc ctgggggcgt gatattaaca   2698
gagggagggt tcccgtgggg ggaagtccat gcctccctgg cctgaagaag agactctttg   2758
catatgactc acatgatgca tacctggtgg gaggaaaaga gttgggaact tcagatggac   2818
ctagtaccca ctgagatttc cacgccgaag gacagcgatg ggaaaaatgc ccttaaatca   2878
taggaaagta ttttttaag ctaccaattg tgccgagaaa agcattttag caatttatac   2938
aatatcatcc agtaccttaa accctgattg tgtatattca tatattttgg atacgcaccc   2998
cccaactccc aatactggct ctgtctgagt aagaaacaga atcctctgga acttgaggaa   3058
gtgaacattt cggtgacttc cgatcaggaa ggctagagtt acccagagca tcaggccgcc   3118
acaagtgcct gcttttagga gaccgaagtc cgcagaacct acctgtgtcc cagcttggag   3178
gcctggtcct ggaactgagc cgggccctca ctggcctcct ccagggatga tcaacagggt   3238
agtgtggtct ccgaatgtct ggaagctgat ggatggagct cagaattcca ctgtcaagaa   3298
agagcagtag aggggtgtgg ctgggcctgt caccctgggg ccctccaggt aggcccgttt   3358
tcacgtggag cataggagcc acgacccttc ttaagacatg tatcactgta gagggaagga   3418
acagaggccc tgggccttcc tatcagaagg acatggtgaa ggctgggaac gtgaggagag   3478
gcaatggcca cggcccattt tggctgtagc acatggcacg ttggctgtgt ggccttggcc   3538
acctgtgagt ttaaagcaag gctttaaatg actttggaga gggtcacaaa tcctaaaaga   3598
agcattgaag tgaggtgtca tggattaatt gacccctgtc tatggaatta catgtaaaac   3658
attatcttgt cactgtagtt tggttttatt tgaaaacctg acaaaaaaaa agttccaggt   3718
gtggaatatg ggggttatct gtacatcctg gggcattaaa aaaaaatcaa tggtggggaa   3778
ctataaagaa gtaacaaaag aagtgacatc ttcagcaaat aaactaggaa attttttttt   3838
cttccagttt agaatcagcc ttgaaacatt gatggaataa ctctgtggca ttattgcatt   3898
atataccatt tatctgtatt aactttggaa tgtactctgt tcaatgttta atgctgtggt   3958
tgatatttcg aaagctgctt taaaaaaata catgcatctc agcgtttttt tgtttttaat   4018
tgtatttagt tatggcctat acactatttg tgagcaaagg tgatcgtttt ctgtttgaga   4078
tttttatctc ttgattcttc aaaagcattc tgagaaggtg agataagccc tgagtctcag   4138
ctacctaaga aaaacctgga tgtcactggc cactgaggag ctttgtttca accaagtcat   4198
gtgcatttcc acgtcaacag aattgtttat tgtgacagtt atatctgttg tccctttgac   4258
cttgtttctt gaaggtttcc tcgtccctgg gcaattccgc atttaattca tggtattcag   4318
gattacatgc atgtttggtt aaacccatga gattcattca gttaaaaatc cagatggcga   4378
atgaccagca gattcaaatc tatggtggtt tgacctttag agagttgctt tacgtggcct   4438
gtttcaacac agacccaccc agagccctcc tgccctcctt ccgcgggggc tttctcatgg   4498
ctgtccttca gggtcttcct gaaatgcagt ggtcgttacg ctccaccaag aaagcaggaa   4558
```

-continued

```
acctgtggta tgaagccaga cctccccggc gggcctcagg gaacagaatg atcagacctt   4618

tgaatgattc taatttttaa gcaaaatatt attttatgaa aggtttacat tgtcaaagtg   4678

atgaatatgg aatatccaat cctgtgctgc tatcctgcca aaatcatttt aatggagtca   4738

gtttgcagta tgctccacgt ggtaagatcc tccaagctgc tttagaagta acaatgaaga   4798

acgtggacgt ttttaatata aagcctgttt tgtcttttgt tgttgttcaa acgggattca   4858

cagagtattt gaaaaatgta tatatattaa gaggtcacgg gggctaattg ctagctggct   4918

gccttttgct gtggggtttt gttacctggt tttaataaca gtaaatgtgc ccagcctctt   4978

ggccccagaa ctgtacagta ttgtggctgc acttgctcta agagtagttg atgttgcatt   5038

ttccttattg ttaaaaacat gttagaagca atgaatgtat ataaaagc                5086


<210> SEQ ID NO 12
<211> LENGTH: 239
<212> TYPE: PRT
<213> ORGANISM: Homo  sapiens

<400> SEQUENCE: 12

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235


<210> SEQ ID NO 13
<211> LENGTH: 1358
<212> TYPE: DNA
<213> ORGANISM: Homo sapiens
<220> FEATURE:
<221> NAME/KEY: CDS
```

-continued

```
<222> LOCATION: (20)...(739)

<400> SEQUENCE: 13

ggcgtccgcg cgctgcaca atg gcg gct ctg aag agt tgg ctg tcg cgc agc      52
                     Met Ala Ala Leu Lys Ser Trp Leu Ser Arg Ser
                      1               5                  10

gta act tca ttc ttc agg tac aga cag tgt ttg tgt gtt cct gtt gtg      100
Val Thr Ser Phe Phe Arg Tyr Arg Gln Cys Leu Cys Val Pro Val Val
            15                  20                  25

gct aac ttt aag aag cgg tgt ttc tca gaa ttg ata aga cca tgg cac      148
Ala Asn Phe Lys Lys Arg Cys Phe Ser Glu Leu Ile Arg Pro Trp His
        30                  35                  40

aaa act gtg acg att ggc ttt gga gta acc ctg tgt gcg gtt cct att      196
Lys Thr Val Thr Ile Gly Phe Gly Val Thr Leu Cys Ala Val Pro Ile
    45                  50                  55

gca cag aaa tca gag cct cat tcc ctt agt agt gaa gca ttg atg agg      244
Ala Gln Lys Ser Glu Pro His Ser Leu Ser Ser Glu Ala Leu Met Arg
 60                  65                  70                  75

aga gca gtg tct ttg gta aca gat agc acc tct acc ttt ctc tct cag      292
Arg Ala Val Ser Leu Val Thr Asp Ser Thr Ser Thr Phe Leu Ser Gln
                80                  85                  90

acc aca tat gcg ttg att gaa gct att act gaa tat act aag gct gtt      340
Thr Thr Tyr Ala Leu Ile Glu Ala Ile Thr Glu Tyr Thr Lys Ala Val
            95                 100                 105

tat acc tta act tct ctt tac cga caa tat aca agt tta ctt ggg aaa      388
Tyr Thr Leu Thr Ser Leu Tyr Arg Gln Tyr Thr Ser Leu Leu Gly Lys
        110                 115                 120

atg aat tca gag gag gaa gat gaa gtg tgg cag gtg atc ata gga gcc      436
Met Asn Ser Glu Glu Glu Asp Glu Val Trp Gln Val Ile Ile Gly Ala
    125                 130                 135

aga gct gag atg act tca aaa cac caa gag tac ttg aag ctg gaa acc      484
Arg Ala Glu Met Thr Ser Lys His Gln Glu Tyr Leu Lys Leu Glu Thr
140                 145                 150                 155

act tgg atg act gca gtt ggt ctt tca gag atg gca gca gaa gct gca      532
Thr Trp Met Thr Ala Val Gly Leu Ser Glu Met Ala Ala Glu Ala Ala
                160                 165                 170

tat caa act ggc gca gat cag gcc tct ata acc gcc agg aat cac att      580
Tyr Gln Thr Gly Ala Asp Gln Ala Ser Ile Thr Ala Arg Asn His Ile
            175                 180                 185

cag ctg gtg aaa ctg cag gtg gaa gag gtg cac cag ctc tcc cgg aaa      628
Gln Leu Val Lys Leu Gln Val Glu Glu Val His Gln Leu Ser Arg Lys
        190                 195                 200

gca gaa acc aag ctg gca gaa gca cag ata gaa gag ctc cgt cag aaa      676
Ala Glu Thr Lys Leu Ala Glu Ala Gln Ile Glu Glu Leu Arg Gln Lys
    205                 210                 215

aca cag gag gaa ggg gag gag cgg gct gag tcg gag cag gag gcc tac      724
Thr Gln Glu Glu Gly Glu Glu Arg Ala Glu Ser Glu Gln Glu Ala Tyr
220                 225                 230                 235

ctg cgt gag gat tga gggcctgagc acactgccct gtctccccac tcagtgggga      779
Leu Arg Glu Asp  *

aagcaggggc agatgccacc ctgcccaggg ttggcatgac tgtctgtgca ccgagaagag    839

gcggcaggtc ctgccctggc caatcaggcg agacgccttt gtgagctgtg agtgcctcct    899

gtggtctcag gcttgcgctg gacctggttc ttagcccttg ggcactgcac cctgtttaac    959

atttcacccc actctgtaca gctgctctta cccatttttt ttacctcaca cccaaagcat   1019

tttgcctacc tgggtcagag agaggagtcc tttttgtcat gcccttaagt tcagcaactg   1079

tttaacctgt tttcagtctt atttacgtcg tcaaaaatga tttagtactt gttccctctg   1139
```

-continued

```
ttgggatgcc agttgtggca gggggagggg aacctgtcca gtttgtacga tttctttgta   1199

tgtatttctg atgtgttctc tgatctgccc ccactgtcct gtgaggacag ctgaggccaa   1259

ggagtgaaaa acctattact actaagagaa ggggtgcaga gtgtttacct ggtgctctca   1319

acaggactta acatcaacag gacttaacac agaaaaaaa                          1358
```

<210> SEQ ID NO 14
<211> LENGTH: 239
<212> TYPE: PRT
<213> ORGANISM: Homo sapiens

<400> SEQUENCE: 14

```
Met Ala Ala Leu Lys Ser Trp Leu Ser Arg Ser Val Thr Ser Phe Phe
 1               5                  10                  15

Arg Tyr Arg Gln Cys Leu Cys Val Pro Val Val Ala Asn Phe Lys Lys
            20                  25                  30

Arg Cys Phe Ser Glu Leu Ile Arg Pro Trp His Lys Thr Val Thr Ile
        35                  40                  45

Gly Phe Gly Val Thr Leu Cys Ala Val Pro Ile Ala Gln Lys Ser Glu
    50                  55                  60

Pro His Ser Leu Ser Ser Glu Ala Leu Met Arg Arg Ala Val Ser Leu
65                  70                  75                  80

Val Thr Asp Ser Thr Ser Thr Phe Leu Ser Gln Thr Thr Tyr Ala Leu
                85                  90                  95

Ile Glu Ala Ile Thr Glu Tyr Thr Lys Ala Val Tyr Thr Leu Thr Ser
            100                 105                 110

Leu Tyr Arg Gln Tyr Thr Ser Leu Leu Gly Lys Met Asn Ser Glu Glu
        115                 120                 125

Glu Asp Glu Val Trp Gln Val Ile Ile Gly Ala Arg Ala Glu Met Thr
    130                 135                 140

Ser Lys His Gln Glu Tyr Leu Lys Leu Glu Thr Thr Trp Met Thr Ala
145                 150                 155                 160

Val Gly Leu Ser Glu Met Ala Ala Glu Ala Ala Tyr Gln Thr Gly Ala
                165                 170                 175

Asp Gln Ala Ser Ile Thr Ala Arg Asn His Ile Gln Leu Val Lys Leu
            180                 185                 190

Gln Val Glu Glu Val His Gln Leu Ser Arg Lys Ala Glu Thr Lys Leu
        195                 200                 205

Ala Glu Ala Gln Ile Glu Glu Leu Arg Gln Lys Thr Gln Glu Glu Gly
    210                 215                 220

Glu Glu Arg Ala Glu Ser Glu Gln Glu Ala Tyr Leu Arg Glu Asp
225                 230                 235
```

<210> SEQ ID NO 15
<211> LENGTH: 20
<212> TYPE: PRT
<213> ORGANISM: Homo sapiens

<400> SEQUENCE: 15

```
Cys Gly Pro Lys Tyr Val Val Pro Val Glu Ser Ser Leu Gly Lys Glu
 1               5                  10                  15

Lys Gly Leu Glu
            20
```